United States Patent [19]

Hagen et al.

[11] Patent Number: 5,491,123
[45] Date of Patent: Feb. 13, 1996

[54] HERBICIDES CONTAINING 3-AMINOBENZO(B)THIOPHENES AS ANTIDOTES

[75] Inventors: Helmut Hagen, Frankenthal; Gerhard Nilz, Dannstadt-Schauernheim; Thomas Roetsch, Ludwigshafen; Helmut Walter, Obrigheim; Andreas Landes, Limburgerhof, all of Germany

[73] Assignee: BASF Aktiengesellschaft, Ludwigshafen, Germany

[21] Appl. No.: 193,073

[22] PCT Filed: Aug. 7, 1992

[86] PCT No.: PCT/EP92/01798

§ 371 Date: Feb. 4, 1994

§ 102(e) Date: Feb. 4, 1994

[87] PCT Pub. No.: WO93/04057

PCT Pub. Date: Mar. 4, 1993

[30] Foreign Application Priority Data

Aug. 16, 1991 [DE] Germany ............ 41 26 999.3

[51] Int. Cl.⁶ .................... A01N 25/32; A01N 43/12
[52] U.S. Cl. .................... 504/104; 504/105; 504/106; 504/108
[58] Field of Search .................... 504/104, 105, 504/106, 108, 288, 289

[56] References Cited

U.S. PATENT DOCUMENTS

| 2,634,201 | 4/1953 | Mowry | 504/289 |
|---|---|---|---|
| 2,930,800 | 3/1960 | Kloetzel | 504/289 |
| 3,836,542 | 9/1974 | Maravetz | 504/289 |
| 4,531,969 | 7/1985 | Nestler et al. | 504/244 |
| 4,703,053 | 10/1987 | Connor et al. | 514/382 |
| 5,041,157 | 8/1991 | Seiler et al. | 544/263 |
| 5,098,466 | 3/1992 | Anderson et al. | 504/289 |
| 5,228,896 | 7/1993 | Misslitz et al. | 504/289 |

FOREIGN PATENT DOCUMENTS

| 201165 | 11/1986 | European Pat. Off. . |
|---|---|---|
| 323590 | 7/1989 | European Pat. Off. . |
| 3212135 | 10/1983 | Germany . |
| 3429830 | 3/1985 | Germany . |
| 3827253 | 3/1989 | Germany . |
| 3740984 | 6/1989 | Germany . |
| WO92/10094 | 6/1992 | WIPO . |
| WO93/04057 | 3/1993 | WIPO . |

OTHER PUBLICATIONS

R. J. Beck, J. Org. Chem. 37(21) (1972), 3224–3226.
H. Schaefer et al., J. Prakt. Chem. 327(2) (1985), 328–332.
K. Gewald et al., Z. Chem. 21(5) (1981), 183–184.

*Primary Examiner*—Richard L. Raymond
*Assistant Examiner*—Brian Bembenick
*Attorney, Agent, or Firm*—Keil & Weinkauf

[57] ABSTRACT

Herbicides contain one or more antagonistic 3-aminobenzo[b]thiophenes I

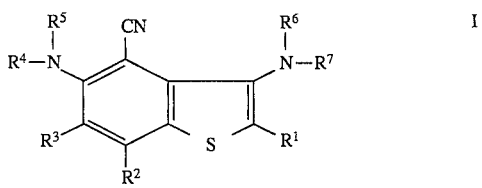

wherein the variables on the compound of formula I are defined in the specification.
A) the group consisting of the cyclohexenone derivatives or
B) the group consisting of the 4-hetaryloxyphenoxyacetic acid derivatives.

8 Claims, No Drawings

HERBICIDES CONTAINING 3-AMINOBENZO(B)THIOPHENES AS ANTIDOTES

The present invention relates to herbicides containing one or more antagonistic 3-aminobenzo[b]thiophenes of the general formula I

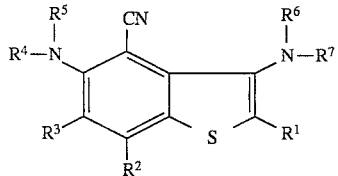

where
$R^1$ is —COX or —COOX,

X is hydrogen, halogen, amino which may be unsubstituted or may carry from one to three substituents selected from the group consisting of $C_1$–$C_4$-alkyl, hydroxy-$C_1$–$C_4$-alkyl, phenyl and benzyl substituents, $C_1$–$C_{10}$-alkyl, $C_2$–$C_8$-alkenyl, $C_3$–$C_{10}$-cycloalkyl or $C_3$–$C_{10}$-cycloalkenyl, where the four last-mentioned groups may be unsubstituted or partially or completely halogenated and the four last-mentioned groups may furthermore contain one or two further carboxyl or carbonyl groups, a 5-membered or 6-membered aromatic heterocyclic structure having one oxygen and one sulfur atom or having from 1 to 3 hetero atoms selected from the group consisting of from 1 to 3 nitrogen atoms and one oxygen or sulfur atom, and all three hetero atoms may not be adjacent to one another at the same time, phenyl or naphthyl, where these groups may carry from one to three substituents selected from the group consisting of halogen, —COY and —COOY, and these groups may additionally carry a number of halogen atoms corresponding to the number of substitutable carbon atoms present;

Y is $C_1$–$C_6$-alkyl, $C_3$–$C_6$-cycloalkyl or phenyl;

$R^2$ and $R^3$ are each hydrogen, cyano, nitro, halogen, mercapto, amino whose nitrogen atom may carry from one to three substituents selected from the group consisting of $C_1$–$C_4$-alkyl, hydroxy-$C_1$–$C_4$-alkyl, phenyl and benzyl substituents, $C_1$–$C_{10}$-alkyl, $C_1$–$C_6$-alkoxy, $C_2$–$C_8$-alkenyl, $C_3$–$C_{10}$-cycloalkyl or $C_3$–$C_{10}$-cycloalkenyl, where the four last-mentioned groups may be partially or completely halogenated, phenyl or naphthyl, a 5-membered or 6-membered aromatic heterocyclic structure having one oxygen and one sulfur atom or having from one to three hetero atoms selected from the group consisting of three nitrogen atoms and one oxygen or sulfur atom, where in the case of three hetero atoms all may not be adjacent to one another at the same time;

$R^4$ to $R^7$ are each hydrogen, phenyl, naphthyl or a 5-membered or 6-membered aromatic heterocyclic structure having one oxygen and one sulfur atom or having from one to three hetero atoms selected from the group consisting of three nitrogen atoms and one oxygen or sulfur atom, where in the case of three hetero atoms all may not be adjacent to one another at the same time and where the aromatic and heteroaromatic groups may furthermore carry from one to three substituents selected from the group consisting of halogen, —COY and —COOY, and these groups may additionally carry a number of halogen atoms corresponding to the number of substitutable carbon atoms present, $C_1$–$C_{10}$-alkyl, $C_2$–$C_6$-alkenyl, $C_3$–$C_{10}$-cycloalkyl or $C_3$–$C_{10}$-cycloalkenyl; or $R^4$ and $R^5$ and/or $R^6$ and $R^7$, together with the nitrogen atom to which they are bonded, form a 5-membered to 7-membered ring, and the basic salts of the compounds I which carry one or more carboxyl, hydroxythiocarbonyl or sulfo groups and the acidic salts of compound I which contain a basic nitrogen atom, and one or more herbicidal active ingredients selected from A) the group consisting of the cyclohexenone derivatives of the general formula II

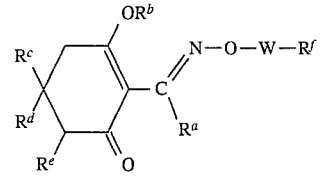

where $R^a$ is $C_1$–$C_6$-alkyl;

$R^b$ is hydrogen, one equivalent of an agriculturally useful cation, $C_2$–$C_8$-alkylcarbonyloxy, $C_1$–$C_{10}$-alkylsulfonyl, $C_1$–$C_{10}$-alkylphosphonyl or benzoyl, benzenesulfonyl or benzenephosphonyl, where the three last-mentioned groups may furthermore each carry from one to five halogen atoms;

$R^c$ is hydrogen, cyano, formyl, $C_1$–$C_6$-alkyl, $C_1$–$C_4$-alkoxy-$C_1$–$C_6$-alkyl or $C_1$–$C_4$-alkylthio-$C_1$–$C_6$-alkyl, phenoxy-$C_1$–$C_6$-alkyl, phenylthio-$C_1$–$C_6$-alkyl, pyridyloxy-$C_1$–$C_6$-alkyl or pyridylthio-$C_1$–$C_6$-alkyl, where the phenyl and pyridyl rings may each furthermore carry from one to three radicals selected from the group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^gR^h$, where $R^g$ is hydrogen, $C_1$–$C_4$-alkyl, $C_3$–$C_6$-alkenyl, $C_3$–$C_6$-alkynyl, $C_1$–$C_6$-acyl or benzoyl which may carry from one to three radicals selected from the group consisting of nitro, cyano, halogen, $C_1$–$C_4$-alkyl, partially or completely halogenated $C_1$–$C_4$-alkyl, $C_1$–$C_4$-alkoxy and $C_1$–$C_4$-alkylthio and $R^h$ is hydrogen, $C_1$–$C_4$-alkyl, $C_3$–$C_6$-alkenyl or $C_3$–$C_6$-alkynyl; $C_3$–$C_7$-cycloalkyl or $C_5$–$C_7$-cycloalkenyl, where these groups may furthermore carry from one to three radicals selected from the group consisting of hydroxyl, halogen, $C_1$–$C_4$-alkyl, partially or completely halogenated $C_1$–$C_4$-alkyl, $C_1$–$C_4$-alkoxy, $C_1$–$C_4$-alkylthio, benzylthio, $C_1$–$C_4$-alkylsulfonyl, $C_1$–$C_4$-alkylsulfenyl and $C_1$–$C_4$-alkylsulfinyl, a 5-membered saturated heterocyclic structure which contains one or two oxygen or sulfur atoms or one oxygen and one sulfur atom as hetero atoms and which may furthermore carry from one to three radicals selected from the group consisting of $C_1$–$C_4$-alkyl, partially or completely halogenated $C_1$–$C_4$-alkyl, $C_1$–$C_4$-alkoxy and $C_1$–$C_4$-alkylthio, a 6-membered or 7-membered saturated heterocyclic structure or mono- or diunsaturated heterocyclic structure which contains one or two oxygen or sulfur atoms or one oxygen and one sulfur atom as hetero atoms and which may furthermore carry from one to three radicals selected from the group consisting of hydroxyl, halogen, $C_1$–$C_4$-alkyl, partially or completely halogenated $C_1$–$C_4$-alkyl, $C_1$–$C_4$-alkoxy and $C_1$–$C_4$-alkylthio, a 5-membered heteroaromatic structure containing from one to three hetero atoms selected from the group consisting of one or two nitrogen atoms and one oxygen or sulfur atom, where the heteroaromatic structure may furthermore carry from one to three radicals selected from a group consisting of cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_2$–$C_6$-alkenyl, $C_2$–$C_6$-alkenyloxy, $C_3$–$C_6$-alkynyloxy and $C_1$–$C_4$-alkoxy-$C_1$–$C_4$-alkyl, phenyl or pyridyl, each of which may furthermore carry from one to three radicals selected from the group consisting of nitro, cyano, formyl, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^gR^h$, where $R^g$ and $R^h$ have the abovementioned meanings;

$R^d$ is hydrogen or hydroxyl or, when $R^c$ is $C_1$–$C_6$-alkyl, $R^d$ is $C_1$–$C_6$-alkyl;

$R^o$ is hydrogen, halogen, cyano, a $C_1$–$C_4$-alkoxycarbonyl or a $C_1$–$C_4$-alkylketoxime group;

W is a $C_1$–$C_6$-alkylene, $C_3$–$C_6$-alkenylene or $C_3$–$C_6$-alkynylene chain, each of which may furthermore carry from one to three radicals selected from the group consisting of three $C_1$–$C_3$-alkyl substituents, three halogen atoms and one methylene substituent; a $C_3$–$C_6$-alkylene or $C_4$–$C_6$-alkenylene chain, both of which may furthermore carry from one to three $C_1$–$C_3$-alkyl radicals, where in each case one methylene group of the chains may be replaced by an oxygen or sulfur atom, a sulfoxyl or sulfonyl group or a group —$N(R^i)$—, where $R^i$ is hydrogen, $C_1$–$C_4$-alkyl, $C_3$–$C_6$-alkenyl or $C_3$–$C_6$-alkynyl; $R^f$ is hydrogen; vinyl; a group —CH=CH—Z, where Z is cyano, halogen, $C_1$–$C_4$-alkyl, partially or completely halogenated $C_1$–$C_4$-alkyl, $C_3$–$C_6$-cycloalkyl, which, if desired, in turn may carry from one to three substituents selected from the group consisting of hydroxyl, halogen, $C_1$–$C_4$-alkyl, partially or completely halogenated $C_1$–$C_4$-alkyl and $C_1$–$C_4$-alkoxy; carboxyl, $C_1$–$C_8$-alkoxycarbonyl, benzyloxycarbonyl, phenyl, thienyl or pyridyl, where these three aromatic radicals may be unsubstituted or may carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio and $C_3$–$C_6$-cycloalkyl, where the cycloalkyl substituent may be unsubstituted or in turn may furthermore carry from one to three radicals selected from the group consisting of halogen, $C_1$–$C_4$-alkyl, partially or completely halogenated $C_1$–$C_4$-alkyl and $C_1$–$C_4$-alkoxy; ethynyl which may carry one of the following radicals: $C_1$–$C_4$-alkyl, $C_3$–$C_6$-cycloalkyl, which, if desired, may carry from one to three substituents selected from the group consisting of hydroxy, halogen, $C_1$–$C_4$-alkyl, partially or completely halogenated $C_1$–$C_4$-alkyl and $C_1$–$C_4$-alkoxy, or phenyl, thienyl or pyridyl, where these aromatic radicals may be unsubstituted or may each furthermore carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy and $C_1$–$C_4$-alkylthio; phenyl, halophenyl, dihalophenyl, a 5-membered heteroaromatic group having from one to three hetero atoms, selected from the group consisting of from one to three nitrogen atoms and one oxygen or sulfur atom, or a 6-membered heteroaromatic group having from one to four nitrogen atoms, all of which may not be adjacent to one another at the same time, where the phenyl and hetaryl groups may, if desired, furthermore carry from one to three radicals selected from the group consisting of nitro, $C_1$–$C_4$-alkoxy, $C_1$–$C_4$-alkylthio, partially or completely halogenated $C_1$–$C_4$-alkoxy, radicals Z and —$NR^kR^l$, where $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl which, if desired, may furthermore carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy and $C_1$–$C_4$-alkylthio, or B) the group consisting of the 2-(4-hetaryloxy)- or 2-(4-aryloxy)-phenoxyacetic acid derivatives of the formula III

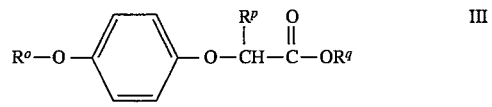

where $R^o$ is phenyl, pyridyl, benzoxazyl, benzothiazyl or benzopyrazinyl, where these aromatic ring systems may be unsubstituted or may carry one or two of the following radicals: halogen, nitro, $C_1$–$C_4$-alkyl, partially or completely halogenated $C_1$–$C_4$-alkyl and/or partially or completely halogenated $C_1$–$C_4$-alkoxy;

$R^p$ is hydrogen or methyl and $R^q$ is hydrogen, $C_1$–$C_4$-alkyl, $C_3$- or $C_4$-alkenyl, $C_3$- or $C_4$-alkynyl, $C_1$–$C_4$-alkoxy-$C_1$–$C_4$-alkyl, $C_3$- or $C_4$-alkylideneiminooxy-$C_2$- or -$C_3$-alkyl, tetrahydrofuranylmethyl, isoxazolidinyl or one equivalent of a plant-tolerated cation.

The present invention furthermore relates to a method for selectively controlling undesirable plant growth on cultivated areas with these herbicides, and novel 3-aminobenzo[b]thiophene derivatives I'.

3-Aminobenzo[b]thiophene derivatives of the type corresponding to compound I are disclosed in the following publications:

R. J. Beck, J. org. Chem. 37(21) (1972), 3224–3226;
H. Schaefer et al., J. Prakt. Chem. 327(2) (1985), 328–332;
K. Gewald et al., Z. Chem. 21(5) (1981), 183–184;
DE-A-37 40 984;
EP-A-323 590;
DE-A-38 27 253;
EP-A-201 165;
EP-A-187 487;
DE-A-34 29 830;
EP-A-378 508 and the prior application DE-A 40 39 734.

However, the compounds described in the stated publications differ from the 3-aminobenzo[b]thiophenes I in positions 4 (cyano group) and 5 (amino group). Furthermore, an antagonistic action of the known compounds in combination with herbicidal active ingredients is not evident from the stated literature.

According to EP-A-378 508, 3-aminothiophenes of the formula

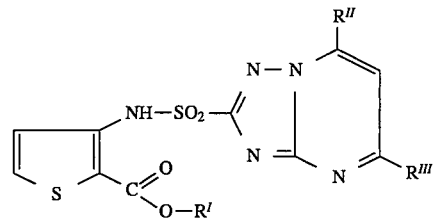

($R^I$=alkyl or cycloalkyl; $R^{II}$ and $R^{III}$=hydrogen, alkyl, trifluoromethyl or cyclopropyl) can be used as antagonistic compounds in herbicidal formulations. However, this publication does not state whether (fused) substituents are possible in the 4- and 5-positions of the thiophene ring.

Finally, DE-A 40 39 734 describes 2-aminothiophenes likewise having an antagonistic effect on herbicides.

Herbicidal mixtures which contain antagonists disclosed in EP-A 378 508 and DE-A 40 39 734 may, however, also have a yield-reducing side effect.

It is an object of the present invention to provide herbicides which ensure good control of undesirable plants without however significantly damaging crops or substantially reducing their yield.

We have found that this object is achieved by the herbicides defined at the outset.

We have also found methods for treating crops with the antagonistic compounds I and the herbicides II or the herbicides III, where the compound I and II or I and III are formulated and applied together or separately and the order in which application is effected in the case of separate application is immaterial.

The herbicides contain one or more antagonistic compounds I and one or more herbicides II or one or more herbicides III.

However, further antagonistic or herbicidal compounds may be present in the novel herbicides.

Derivatives I having acidic terminal groups or having basic nitrogen atoms may be present in the form of their agriculturally useful salts.

Suitable agriculturally useful salts are in general the salts of acids or bases which do not adversely affect the antagonistic action of I.

Examples of suitable acid addition salts are hydrochlorides, hydrobromides, sulfates, nitrates, phosphates, oxalates and dodecylbenzenesulfonates.

Examples of suitable basic salts are those of the alkali metals, in particular the sodium and potassium salts, those of the alkaline earth metals, in particular calcium, magnesium and barium salts, and those of the transition metals, in particular manganese, copper, zinc and iron salts, as well as the ammonium salts, which, if desired, may carry from one to three $C_1$–$C_4$-alkyl or hydroxy-$C_1$–$C_4$-alkyl substituents and/or one phenyl or benzyl substituent, in particular diisopropylammonium, tetramethylammonium, tetrabutylammonium, trimethylbenzylammonium and trimethyl-(2-hydroxyethyl)-ammonium salts, phosphonium salts, sulfonium salts, in particular tri-$C_1$–$C_4$-alkylsulfonium salts and the sulfoxonium salts, in particular tri-$C_1$–$C_4$-alkylsulfoxonium salts.

The substituents of the 3-aminobenzo[b]thiophenes I have the following specific meanings:

$R^1$ is —COX or —COOX, where X is hydrogen, halogen, such as fluorine, chlorine, bromine or iodine, in particular fluorine or chlorine, amino which, if desired, may carry from one to three substituents selected from the group consisting of $C_1$–$C_4$-alkyl substituents such as methyl, ethyl, n-propyl, 1-methylethyl, n-butyl, 1-methylpropyl, 2-methylpropyl and 1,1-dimethylethyl, preferably methyl or ethyl, hydroxy-$C_1$–$C_4$-alkyl substituents, such as hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 1-hydroxybut-3-yl, 2-hydroxybut-3-yl, 1-hydroxy-2--methylprop-3-yl, 2-hydroxy-2-methylprop-3-yl, 3-hydroxy-2-methylprop-3-yl or 2-hydroxymethylprop-2-yl, preferably 1-hydroxyeth-1-yl, phenyl and benzyl substituents, $C_1$–$C_{10}$-alkyl, in particular $C_1$–$C_6$-alkyl, such as methyl, ethyl, n-propyl, 1-methylethyl, n-butyl, 1-methylpropyl, 2-methylpropyl, 1,1-dimethylethyl, n-pentyl, 2-methylbutyl, 3-methylbutyl, 2,2-dimethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, isopropyl or tert-butyl, where each alkyl group may be unsubstituted or may carry one or two radicals selected from the group consisting of halogen as stated above, in particular fluorine and chlorine, carboxyl and carbonyl, and where each alkyl group may additionally carry a number of halogen atoms as stated above, in particular fluorine and chlorine, which corresponds to the number of substitutable H atoms present, $C_2$–$C_8$-alkenyl, in particular $C_2$–$C_6$-alkenyl, such as ethenyl, 1-propenyl, 2-propenyl, 1-methylethenyl, 1-butenyl, 2-butenyl, 3-butenyl 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, preferably ethenyl or prop-1-enyl, where each alkenyl group may be unsubstituted or may carry one or two radicals selected from the group consisting of halogen as stated above, in particular fluorine and chlorine, carboxyl and carbonyl, and where each alkenyl group may, if desired, additionally carry a number of halogen atoms as stated above, in particular fluorine or chlorine, which corresponds to the number of substitutable H atoms present, $C_3$–$C_{10}$-cycloalkyl or $C_3$–$C_{10}$-cycloalkenyl, in particular $C_3$–$C_8$-cycloalkyl or $C_5$–$C_8$-cycloalkenyl, such as cyclopropyl, cyclobutyl, cyclopentyl, cyclohexyl, cycloheptyl, cyclooctyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclooct-1-enyl, cyclooct-2-enyl, cyclooct-3-enyl or cyclooct-1-enyl, preferably cyclopentyl or cyclohexyl, where each carbocyclic radical may be unsubstituted or may carry one or two radicals selected from the group consisting of halogen as stated above, in particular fluorine and chlorine, carboxyl and carbonyl, and where each carbocyclic radical may, if desired, additionally carry a number of halogen atoms as stated above, in particular fluorine or chlorine, which corresponds to the number of substitutable H atoms present, a 5-membered or 6-membered aromatic heterocyclic structure having one oxygen and one sulfur atom or having from 1 to 3 hetero atoms selected from the group consisting of 3 nitrogen atoms and one oxygen or sulfur atom, where all three hetero atoms may not be adjacent to one another at the same time, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl, preferably pyrid-2-yl; phenyl or naphthyl, where these groups may be unsubstituted or may carry from one to three substituents selected from the group consisting of halogen as stated above, in particular fluorine and chlorine, —COY and —COOY, and where these groups may additionally carry a number of halogen atoms as stated above, in particular fluorine or chlorine, which corresponds to the number of substitutable H atoms present; and Y is $C_1$–$C_6$-alkyl as stated above, in particular methyl or ethyl, $C_3$–$C_6$-cycloalkyl as stated above, preferably cyclopentyl or cyclohexyl, or phenyl.

Very particularly preferably, $R^1$ is hydrogen, acyl, methoxycarbonyl, n-butoxycarbonyl, tert-butoxycarbonyl, 2-heptyloxycarbonyl, 1-propen-3-oxycarbonyl or benzyloxycarbonyl, carboxamido, an ethyl carboxyacetate group, ethyl oxalate group or benzoyl, $R^2$ and $R^3$ independently of one another are each hydrogen, cyano, nitro, mercapto, halogen, such as fluorine, chlorine, bromine or iodine, in particular fluorine or chlorine, amino which may be unsubstituted or may carry from one to three substituents selected from the group consisting of $C_1$–$C_4$-alkyl substituents as stated above, preferably methyl, hydroxy-$C_1$–$C_4$-alkyl substituents as stated above, phenyl and benzyl substituents, $C_1$–$C_{10}$-alkyl, in particular $C_1$–$C_6$-alkyl as stated above, preferably methyl or ethyl, where each alkyl group may be unsubstituted or may carry one or two radicals selected from the group consisting of halogen as stated above, in particular fluorine and chlorine, carboxyl and carbonyl, and where each alkyl group may, if desired, additionally carry a number of halogen atoms as stated above, in particular fluorine or chlorine, which corresponds to the number of substitutable H atoms present, $C_1$–$C_6$-alkoxy, such as methoxy, ethoxy, n-propoxy, 1-methylethoxy, n-butoxy, 1-methylpropoxy, 2-methylpropoxy, 1,1-dimethylethoxy, n-pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, preferably methoxy or ethoxy, $C_2$–$C_8$-alkenyl, in particular $C_2$–$C_6$-alkenyl as stated above, preferably ethenyl, where each alkenyl group may be unsubstituted or may carry one or two radicals selected from the group consisting of halogen as stated above, in particular fluorine and chlorine, carboxyl and carbonyl, and where each alkenyl group may, if desired, additionally carry a number of halogen atoms as stated above, in particular fluorine or chlorine, which corresponds to the number of substitutable H atoms present, $C_3$–$C_{10}$-cycloalkyl or $C_3$–$C_{10}$-cycloalkenyl, in particular $C_3$–$C_8$-cycloalkyl or $C_5$–$C_8$-cycloalkenyl as stated above, preferably cyclopentyl or cyclohexyl, where the carbocyclic radicals may be unsubstituted or may carry one or two radicals selected from the group consisting of halogen as stated above, in particular fluorine and chlorine, carboxyl and carbonyl, and where each carbocyclic radical may, if desired, additionally carry a number of halogen atoms as stated above, in particular fluorine or chlorine, which corresponds to the number of substitutable H atoms present, phenyl or naphthyl, each of which may be unsubstituted or may carry from one to three substituents selected from the group consisting of halogen as stated above, in particular fluorine and chlorine, —COY and —COOY as stated above, and where the phenyl and the naphthyl group may, if desired, additionally carry a number of halogen atoms corresponding to the number of substitutable H atoms present, or a 5-membered or 6-membered aromatic heterocyclic structure having one oxygen and one sulfur atom or having from 1 to 3 hetero atoms selected from the group consisting of from 1 to 3 nitrogen atoms and one oxygen or sulfur atom, where all three hetero atoms may not be adjacent to one another at the same time, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-tri-azol-3-yl, 1,3,4-oxadiazol-2-yl, 1,3,4-thiadiazol-2-yl, 1,3,4-triazol-2-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl, preferably pyrid-2-yl, pyrid-3-yl or pyrid-4-yl.

Very particularly preferably, $R^2$ and $R^3$ are each hydrogen and $R^4$ to $R^7$ independently of one another are each hydrogen, $C_1$–$C_{10}$-alkyl, in particular $C_1$–$C_6$-alkyl as stated above, preferably methyl or ethyl, where each alkyl group may be unsubstituted or may carry one or two radicals selected from the group consisting of halogen as stated above, in particular fluorine and chlorine, carboxyl and carbonyl, and where each alkyl group may, if desired, additionally carry a number of halogen atoms as stated above, in particular fluorine or chlorine, which corresponds to the number of substitutable H atoms present, $C_2$–$C_8$-alkenyl, in particular $C_2$–$C_6$-alkenyl as stated above, preferably ethenyl, where each alkenyl group may be unsubstituted or may carry one or two radicals selected from the group consisting of halogen as stated above, in particular fluorine and chlorine, carboxyl and carbonyl, and where each alkenyl group may, if desired, additionally carry a number of halogen atoms as stated above, in particular fluorine or chlorine, which corresponds to the number of substitutable H atoms present, $C_3$–$C_{10}$-cycloalkyl or $C_3$–$C_{10}$-cycloalkenyl, in particular $C_3$–$C_8$-cycloalkyl or $C_5$–$C_8$-cycloalkenyl as stated above, preferably cyclopentyl or cyclohexyl, where each carbocyclic radical may be unsubstituted or may carry one or two radicals selected from the group consisting of halogen as stated above, in particular fluorine and chlorine, carboxyl and carbonyl, and where each carbocyclic radical may, if desired, additionally carry a number of halogen atoms as stated above, in particular fluorine or chlorine, which corresponds to the number of substitutable H atoms present, phenyl or naphthyl, each of which may be unsubstituted or may carry from one to three substituents selected from the group consisting of halogen as stated above, in particular fluorine and chlorine, —COY and —COOY as stated above, and where the phenyl and the naphthyl group may, if desired, additionally carry a number of halogen atoms corresponding to the number of substitutable H atoms present, or a 5-membered or 6-membered aromatic heterocyclic structure having one oxygen and one sulfur atom or having from 1 to 3 hetero atoms selected from the group consisting of 3 nitrogen atoms and one oxygen or sulfur atom, where all three hetero atoms may not be adjacent to one another at the same time, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl, preferably pyrid-2-yl, pyrid-3-yl or pyrid-4-yl, where each heterocyclic structure may be unsubstituted or may carry one or two substituents selected from the group consisting of halogen as stated above, in particular fluorine and chlorine, —COY and —COOY as stated above, and where the heterocyclic structure may, if desired, additionally carry a number of halogen atoms corresponding to the number of substitutable H atoms present, or $R^4$ and $R^5$ or $R^6$ and $R^7$, together with the particular nitrogen atom to which they are bonded, from a 5-membered, 6-membered or 7-membered heterocyclic structure, such as pyrrolidinyl, piperidinyl, morpholinyl or azepinyl;

$R^4$ to $R^7$ are each very particularly preferably hydrogen.

3-Aminobenzo[b]thiophenes of the formula I'

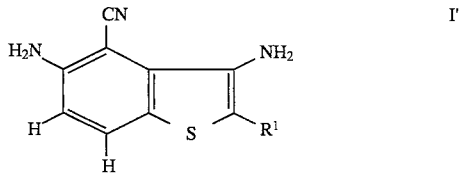

are novel.

The 3-aminobenzo[b]thiophenes of the formulae I and I' are obtainable by various methods, preferably by one of the following processes:

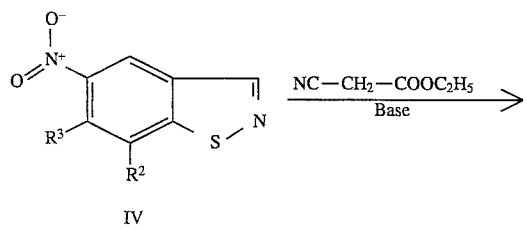

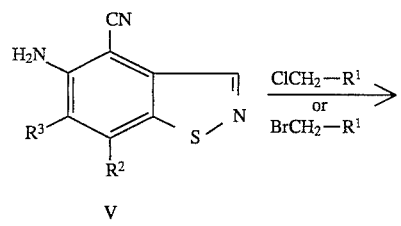

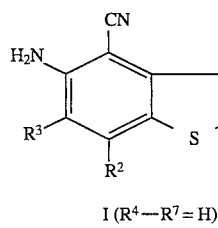

The introduction of the cyano group into the nitrobenzothiazole IV with simultaneous reduction of the nitro group is advantageously carried out by means of ethyl cyanoacetate in the presence of a base by a method known from the literature [cf. Chem. Pharm. Bull. 30 (1982), 851].

Examples of suitable bases are alkali metal hydroxides, such as sodium hydroxide and potassium hydroxide, alkaline earth metal alcoholates, such as sodium methylate and potassium tert-butylate, potassium tert-butylate being particularly preferred.

The reaction is preferably carried out in an insert solvent, in particular in a polar aprotic solvent, such as dimethylformamide or N-methylpyrrolidone.

The amount of solvent is not critical; as a rule, it is chosen so that the reaction mixture remains readily stirrable; it is preferably from 3 to 6 times the molar amount, based on the amount of IV.

The reaction is generally carried out using an excess of ethyl cyanoacetate, for example from 2 to 6, preferably 3, times the molar amount, based on the amount of nitrobenzothiazole IV.

The amount of base is not critical. For a high conversion, it is advisable to use from half to twice the molar amount, based on the amount of ethyl cyanoacetate, of base.

The base and the cyanoacetic ester are preferably used in about a stoichiometric ratio.

Reaction temperatures of from about 0° to 100° C. in particular from 20° to 80° C., preferably from 40° to 60° C., are usually sufficient.

In general, the reaction is carried out at from 0.5 to 5, in particular from 0.8 to 3, bar, preferably at atmospheric pressure.

The cyanobenzothiazole V is converted into the compounds I, for example with chloro- or bromoacetic acid derivatives, advantageously in a polar solvent, such as sulfolane or methoxypropanal.

This reaction is advantageously carried out in the presence of a strong base, for example an alkali metal hydroxide, such as sodium hydroxide or potassium hydroxide.

All reactants are preferably used in stoichiometric amounts, but an excess of one or other component, up to about 5 mol %, may be advantageous.

The reaction temperature is usually from 20° to 200° C., preferably from 80° to 200° C., in particular from 160° C. to the boiling point of the particular diluent.

Regarding the pressure, the statements made above for the conversion of the nitrobenzothiazoles IV into the cyanobenzothiazole V are applicable.

The reaction mixtures are worked up in a conventional manner, for example by mixing with water, separating the phases and, if required, purifying the crude products by chromatography. Some of the intermediates and end products are obtained in the form of colorless or slightly brownish, viscous oils, which are freed from volatile constituents or are purified under reduced pressure and at moderately elevated temperatures. If the intermediates and end products are obtained as solids, purification may also be effected by recrystallization or digestion.

The cyanobenzothiazoles V are novel.

Further 3-aminobenzo[b]thiophenes I in which one or more of the substituents $R^4$ to $R^7$ are not hydrogen can be prepared in a conventional manner, for example by reacting the amino groups with Hal-$R^4$, Hal-$R^5$, Hal-$R^6$ or Hal-$R^7$, Hal being halogen, such as chlorine or bromine.

As a rule, the reaction is carried out in the presence of a base, for example alkali metal hydroxides, such as sodium hydroxide and potassium hydroxide, alkaline earth metal hydroxides, such as calcium hydroxide, alkali metal alcoholates, such as sodium methylate, sodium ethylate, potassium ethylate and potassium tert-butylate, alkaline earth metal alcoholates, such as calcium alcoholate, alkali metal hydrides, such as sodium hydride and potassium hydride, alkaline earth metal hydrides, such as calcium hydride, aliphatic amines, such as dimethylamine, triethylamine, diisopropylamine, dimethylaniline, dimethylbenzylamine and piperidine, and heteroaromatic amines, such as pyridine and 4-dimethylaminopyridine, being suitable.

Examples of inert solvents or diluents are aliphatic hydrocarbons, such as n-hexane, gasoline and petroleum ether, aromatic hydrocarbons, such as benzene, toluene and xylene, chlorinated hydrocarbons, such as dichloromethane, chloroform, tetrachloromethane, 1,2-dichloroethane and chlorobenzene, nitrogen-containing heteroaromatics, such as pyridine and quinoline, cyclic ethers, such as tetrahydrofuran and dioxane, nitriles, such as acetonitrile and propionitrile, and dimethylformamide, dimethyl sulfoxide and N-methylpyrrolidone or a mixture of the stated solvents. When a phase transfer catalyst, such as trioctylpropylammonium chloride or cetyltrimethylammonium chloride, is present, the reaction can also be carried out in a 2-phase system comprising water and a hydrocarbon, eg. carbon tetrachloride.

Advantageously, all reactants are used in stoichiometric amounts, but an excess of up to about 10 mol % of one or other component may also be used.

In general, the reaction temperature is from 0° to 200° C., preferably from 20° to 140° C., in particular at the boiling point of the particular solvent.

Further synthesis methods for the preparation of the 3-aminobenzo[b]thiophenes I are described in the following literature:
R. J. Back, J. Org. Chem. 37(21) (1972), 3224–3226;
H. Schaefer et al., J Prakt. Chem. 327(2) (1985), 328–332;
E. Gewald et al., Z. Chem. 21(5) (1981), 183–184;
DE-A-37 40 984;
EP-A-323 590;
DE-A-38 27 253;
EP-A-201 165;
EP-A-187 487;
DE-A-34 29 830;
EP-A-378 508 and the prior application DE-A 40 39 734.

The 3-aminobenzo[b]thiophenes I or I' are suitable as antidotes for making herbicidal active ingredients more compatible with crops such as millet, rice, corn, cereal species (wheat, rye, barley and oats), cotton, sugar beet, sugar cane and soybean. They have an antagonistic effect on herbicides from a very wide range of classes, such as triazines, phenylurea derivatives, carbamates, thiocarbamates, haloacetanilides, benzoic acid derivatives and in particular halophenoxyacetic esters, substituted phenoxyphenoxyacetic esters, phenoxyphenoxypropionic esters and in particular cyclohexenone derivatives.

Herbicidal cyclohexenone derivatives II are disclosed in, for example, EP-A 228 598, EP-A 230 235, EP-A 238 021, EP=A 368 227, U.S. Pat. No. 4,432,786, DE-A 24 39 104 and DE-A 38 38 309. They are used predominantly for controlling undesirable grasses in dicotyledon crops and in grasses which do not belong to the Gramineae family. Depending on the substituents and on the dose of the compounds of type II during their application, these cyclohexenones can also be used for selectively controlling undesirable grasses in gramineous crops, such as wheat and rice.

Further cyclohexenone derivatives II can be prepared in a conventional manner by synthesis methods known from the literature (cf. for example EP-A 169 521), for example by reacting triketones VI (disclosed in, for example, EP-A 80 301, EP-A 125 094, EP-A 142, 741, U.S. Pat. No. 4,249,937, EP-A 137 174 and EP-A 177 913) with hydroxylamines VII (disclosed in, for example, Houben-Weyl, Methoden der Organischen Chemie, Volume 10/1, page 1181 et seq.);

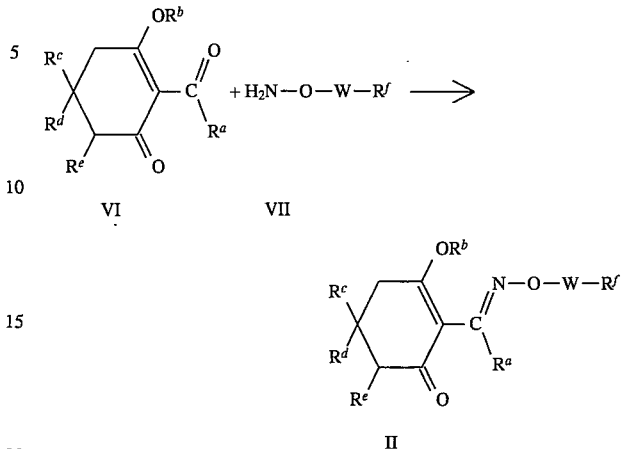

The reaction is advantageously carried out in the heterogeneous phase in a solvent, preferably in the presence of a base, the hydroxylamine preferably being used in the form of the ammonium salt.

Examples of suitable bases are the carbonates, bicarbonates, acetates, alcoholates and oxides of alkali metals and alkaline earth metals, such as sodium hydroxide, potassium hydroxide, magnesium oxide and calcium oxide, as well as organic bases, such as pyridine and tertiary amines, eg. triethylamine.

The triketone and the hydroxylamine are preferably used in about stoichiometric amounts. The amount of base is not critical but is usually from about 0.5 to 2 mol equivalent, based on the amount of VI.

The reaction temperature is in general from 0° to 80° C.

Examples of suitable solvents are dimethyl sulfoxide, alcohols, such as methanol, ethanol and isopropanol, hydrocarbons, such as hexane and cyclohexane, aromatic hydrocarbons, such as benzene and toluene, esters, such as ethyl acetate, and ethers, such as diethyl ether, dioxane and tetrahydrofuran. The reaction is preferably carried out in methanol using sodium bicarbonate as the base.

The reaction is complete after a few hours. The product II can be isolated, for example, by evaporating down the mixture, partitioning the residue between methylene chloride and water and distilling off the solvent under reduced pressure.

However, it is also possible to use the free hydroxylamine base, for example in the form of an aqueous solution, directly for this reaction; depending on the solvent used for the hydroxylamine VII, a one-phase or two-phase reaction mixture is obtained.

Suitable solvents for this variant are, for example, alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile and cyclic ethers, such as dioxane and tetrahydrofuran.

No special conditions are required with regard to the pressure; the reaction is therefore usually carried out at atmospheric pressure.

Alkali metal salts of the compounds II can be obtained by treating the 3-hydroxy compounds with sodium hydroxide, potassium hydroxide or a sodium or potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts by means of ammonia or phosphonium, sulfonium or sulfoxonium hydroxides.

The compound of type VI can be prepared, for example, from the corresponding cyclohexane-1,3-diones of the formula VIII

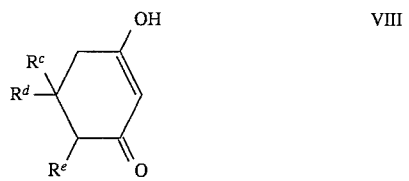

by known methods (Tetrahedron Lett. (1975), 2491).

It is also possible to prepare the compounds of the formula VI via the enol ester intermediates, which are obtained in the reaction of compounds of the formula VIII with acyl chlorides in the presence of a base and are then subjected to a rearrangement reaction with certain imidazole or pyridine derivatives (Japanese Preliminary Published Application 79.063 052).

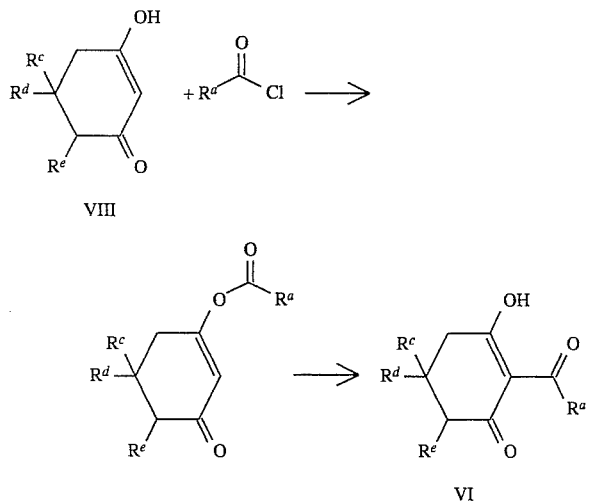

The hydroxylamines of the formula VII are obtained, as a rule, via a number of known process steps, starting from known intermediates:

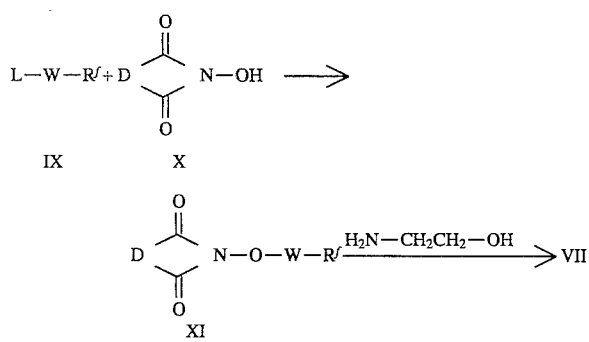

L=the hydroxyl group or a leaving group, for example halogen, such as chlorine, bromine or iodine, or $CH_3SO_2$—O—.

The alkylating agents required for the synthesis of the hydroxylamines VII are known from the literature or can be prepared by known methods.

Syntheses of derivatives in which W is an aliphatic or olefinic chain which may be interrupted by hetero atoms are described in the following publications: DE-A 34 37 919; Tetrahedron Lett. 28 (1979), 2639; Org. Synth. Coll. Vol. 1 (1944), 436; DE-A 26 54 646; DE-A 27 14 561; J. Org. Chem. 52 (1987(, 3587; DE-A 948 871; DE-A 948 872; J. Med. Chem. 26 (1983), 1570; Synthesis (1983), 675; J. Org. Chem. 48 (1983), 497; Org. Synth. Coll. Vol. V. 249; EP-A 48 911; EP-A 143 952; U.S. Pat. No. 4,686,735.

For the preparation of compounds II in which W is an aliphatic or olefinic chain and $R^f$ is a heterocyclic structure, reference may be made to the following literature:

J. Heterocycl. Chem. 14 (1976), 525; JP 55 051 004; JP 55 047 601; Houben-Weyl; Methoden der organischen Chemie, 4th Edition 1971, Volume 4/3, page 424 et seq.; DE-A-28 21 409; Chem. Ber. 114 (1981), 3667 and 3674.

Preparation methods starting from suitable carbinols IX (L=OH) are disclosed, for example, in: Tetrahedron 35 (1979), 329; Chem. Lett. (1977), 423; Houben-Weyl: Methoden der organischem Chemie, 4th Edition 1984, Volume 13/9B, page 964 et seq.; ibid., 4th Edition 1962, Volume 5/3, pages 862 and 899 et seq.; ibid., 4th Edition 1960, Volume 5/4, page 361 et seq.

The preparation of alkylating agents in which W is substituted or unsubstituted $C_3$–$C_6$-alkynyl can be carried out by classical methods [cf. J. Med. Chem. 29 (1986), 1389; ibid. 24 (1981), 678; EP-A 131 302; J. Chem. Ecol. 10 (1982), 1201) or by coupling 1-alkynyl derivatives with aryl or hetaryl halides in the presence of palladium catalysts [cf. for example Tetrahedron Lett. 50 (1975), 4467].

IX is coupled with a cyclic hydroximide X, and the resulting protected hydroxylamine derivative XI is cleaved, preferably with 2-aminoethanol, to give the free hydroxylamine VII.

When HO-W-$R^f$ is used, it is advisable to employ the Mitsunobu method [cf. Synthesis (1981), 1 and J. Med. Chem. 33 (1990), 187].

In the cyclic hydroximides X, D is, for example, $C_2$- or $C_3$-alkylene, $C_2$-alkenylene or a 5-membered or 6-membered ring which contains not more than 3 double bonds and may contain a nitrogen atom, for example phenylene, pyridylene, cyclopentylene, cyclohexylene or cyclohexenylene. For example, the following substances are suitable:

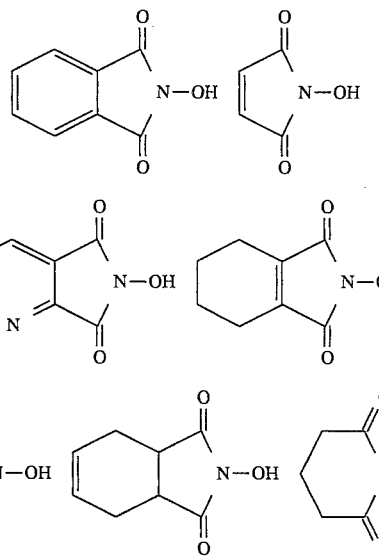

The reaction of the compounds IX with the hydroximides X is advantageously carried out in the presence of a base. All bases capable of deprotonating the hydroximides X without attacking the imide system are in principle suitable. These are in particular the non-nucleophilic bases. Examples are mineral bases, such as alkali metal and alkaline earth metal carbonates and alkali metal and alkaline earth metal bicarbonates, and organic bases, such as aliphatic, cyclohaliphatic and aromatic tertiary amines. It is also possible to use mixtures of these bases.

Examples of individual compounds are the following bases: sodium carbonate potassium carbonate, magnesium carbonate, calcium carbonate, barium carbonate, bicarbonates of these metals, trimethylamine, triethylamine, tributylamine, ethyldiisopropylamine, N,N-dimethylaniline, 4-N,N-dimethylaminopyridine, diazabicyclooctane, diazabicycloundecane, N-methylpiperidine, 1,4-dimethylpiperidine, pyridine, quinoline, bipyridine and phenanthroline. The economical bases sodium carbonate and potassium carbonate are preferred.

The base is added in general in equivalent amounts up to an excess of 5 equivalents, based on the hydroximide. A larger excess is possible but has no additional advantages. It is also possible to use a smaller amount of base. Preferably, however, the base is used in an amount of from 1 to 3, in particular from 1 to 2, equivalents, based on the hydroximide X.

The use of nucleophilic bases, for example alkali metal and alkaline earth metal hydroxides, in particular sodium hydroxide and potassium hydroxide, is also possible. In this case, it is advantageous to use the base in equivalent amounts, based on the hydroximide X, in order to avoid a nucleophilic attack by the hydroxyl ions on the carbonyl function of the imido group.

The starting compounds IX are advantageously reacted with the hydroximides X in a solvent which is inert under the reaction conditions. Examples of advantageous solvents are polar aprotic solvents, such as dimethylformamide, N-methylpyrrolidone, dimethyl sulfoxide, sulfolane and cyclic ureas. The amount of solvent is in general not critical.

The reaction of the starting compounds IX with the hydroximides X can also be carried out using phase transfer catalysis. In this case, solvents which form two phases with water are used, these solvents preferably being chlorohydrocarbons. Suitable phase transfer catalysts are the quaternary ammonium and phosphonium salts, polyethylene glycols, polyethylene glycol ethers and crown ethers usually used for such purposes, as described in, for example, Dehmlow et al., Phase Transfer Catalysis, pages 37–45 and pages 86–93, Verlag Chemie, Weinheim 1980. The phase transfer catalyst are advantageously used in amounts of from 1 to 10, preferably from 3 to 5, % by volume ,based on the volume of the reaction mixture.

The reaction of the starting compounds IX with the hydroximides X is carried out in general at from 0° to 140° C., preferably from 20° to 100° C., in particular from 40° to 80° C. In an advantageous procedure, the hydroximide X is initially taken together with the base in a solvent, and the starting material IX is metered into this solution. It may prove advantageous if the hydroximide is added at a lower temperature, for example at from 0° to 50° C., and the reaction mixture is heated to the actual reaction temperature only after this addition.

As a rule, the reaction is carried out at atmospheric pressure or under the autogenous pressure of the solvent.

After the end of the reaction, water is advantageously added to the cooled reaction mixture, the resulting hydroxylamine derivatives XI separating out as crystalline solids or as oils. The hydroxylamine derivatives obtained in this manner can, if desired, be further purified by recrystallization or by extraction.

The hydroxylamine derivatives XI can be temporarily stored or can be converted immediately into the hydroxylamine derivatives VII having a free amino group. This conversion can be carried out by conventional methods, as described in, for example, DE-A 36 15 973 and the publications cited therein. The process according to DE-A 36 15 973 is preferably used, according to which the hydroxylamine derivatives VII are liberated by means of ethanolamine. The liberation of the hydroxylamine derivatives VII with the aid of other bases, such as aqueous mineral bases, amines, hydrazines or hydroxylamines, or by means of aqueous acids, is also possible.

The hydroxylamine derivatives VII can be isolated from the reaction mixtures obtained in these processes by conventional working up methods, for example by extraction or by crystallization. To increase the tendency of these hydroxylamine derivatives to crystallize, it may often be beneficial to convert them into their salts with mineral acids or organic acids. For this purpose, dilute solutions of these acids are generally reacted with the hydroxylamine derivatives VII, advantageously in equivalent amounts. As in the case of the hydroxylamine derivatives VII having a free amino group, the resulting hydroxylammonium salts can be further converted directly into the herbicides of the formula II or, if desired, can be stored.

The cyclohexenone derivatives II may be obtained as isomer mixtures in the preparation, and both E/Z isomer mixtures and enantiomer or diastereoisomer mixtures are possible. The isomer mixtures can, if desired, be separated by the conventional methods, for example by chromatography or by crystallization.

The cyclohexenone derivatives II may occur in a plurality of tautomeric forms, and the invention relates to all of them.

Preparation Examples (cyclohexanone derivatives)

EXAMPLE 1

2-[1-(3-(4-Bromophenyl)-prop-2-enyloximino)-propyl]-3-hydroxy-5-(3-tetrahydrothiopyranyl)-cyclohex-2-en-1-one

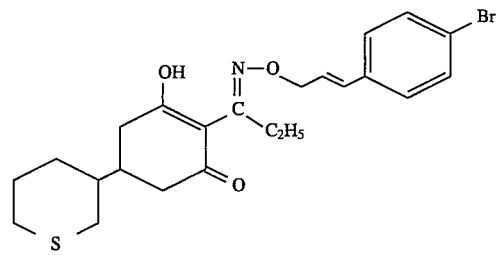

3.0 g (0.011 mol) of 2-propionyl-5-( 3-tetrahydrothiopyranyl)-cyclohexane-1,3-dione and 3.0 g (0.013 mol) of 3-(4-bromophenyl)-prop-2-enyloxyamine in 100 ml of methanol were stirred at 20° C. for 16 hours. The precipitated reaction product was separated off at 0° C., washed with ice-cold methanol and petroleum ether and dried. Yield: 68.4% mp.: 97°–99° C.

Intermediate 1.1

N-[3-(4-Bromophenyl)-prop-2-enyloxy]-phthalimide 18.5 g (0.11 mol) of N-hydroxyphthalimide and 31.4 g (0.11 mol) of 1-bromo-[3-(4-bromophenyl)]-prop- 2-ene were added in succession to 350 ml of dry N-methylpyrrolidone, after which 12.1 g (0.12 mol) of triethylamine were added dropwise at room temperature. The reaction mixture was stirred for four days at 20° C. and then poured onto 1.5 l of ice water, and the product was filtered off and washed with water and isopropanol. Yield: 86.8%; mp.: 161°–162° C.

Intermediate 1.2

3-(4-Bromophenyl)-prop-2-enyloxyamine 33.4 g (0.093 mol) of N-[3-(4-bromophenyl)-prop-2-enyloxy]-phthalimide were introduced a little at a time into 50 ml of ethanolamine and the temperature increased to 30° C. during this procedure. The mixture was stirred for two hours at 60° C. and then allowed to cool, and 200 ml of dichloromethane were added. The mixture was extracted by shaking with ice water. After drying was evaporating down the organic phase, the residue was recrystallized from petroleum ether. Yield: 95.3%; mp.: 35°–38° C.

EXAMPLE 2

2-[1-(4-(4-Fluorophenyl)-but-3-ynyloximino]-butyl-3-hydroxy-5-tetrahydropyran-4-ylcyclohex-2-enone

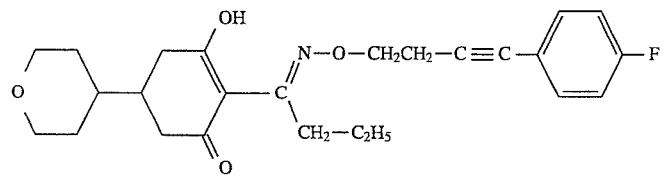

2.7 g (15 mmol) of 4-(4-fluorophenyl)-but-3-ynoxyamine were added to a solution of 4 g (15 mmol) of 2-butyryl-3-hydroxy-5-tetrahydropyran-4-ylcyclohex-2-enone in 60 ml of dry methanol. The mixture was stirred for 16 hours at room temperature, after which the methanol was removed under reduced pressure from a water pump. The crude product was purified by chromatography over silica gel (mobile phase: methylene chloride). Yield: 81.2%.

Intermediate 2.1

4-(4-Fluorophenyl)-3-butynol 1 g of bis-(triphenylphosphine)-palladium(II) chloride, 3.8 g of copper(I) iodide and 8.7 g of triphenylphosphine were added in succession to a solution of 100 g of 4-bromofluorobenzene in 350 ml of triethylamine. The mixture was heated to reflux temperature, after which 43.4 g of 3-butynol were added dropwise in the course of 20 minutes at this temperature (about 100° C.). Stirring was carried out for a further 5 hours at this temperature. After the mixture had cooled, the triethylamine was distilled off. The residue was taken up in methyl tert-butyl ether and water. The aqueous phase was extracted twice more with methyl tert-butyl ether, and the combined organic extracts were washed in succession with 1 N hydrochloric acid and with 10% strength by weight sodium bicarbonate solution and dried over sodium sulfate. After removal of the solvent, the crude product was distilled under greatly reduced pressure. Yield: 86%.

Intermediate 2.2

N-(5-(4-Fluorophenyl)-4-pentynyloxy)-phthalimide 33.4 g (0.205 mol) of N-hydroxyphthalimide and 53.8 g (0.205 mol) of triphenylphosphine were added to a solution of 33.1 g (0.186 mol) of 5-hydroxy-1-(4-fluorophenyl)-1-pentyne in 430 ml of dry tetrahydrofuran. 35.7 g (0.205 mol) of diethyl azodicarboxylate were then added dropwise in the course of 2.5 hours under temperature control (not more than 40° C.). Stirring was carried out overnight at room temperature, the mixture was evaporated down under reduced pressure and the residue was taken up with 300 ml of dichloromethane. The solution was washed twice with sodium carbonate solution and once with saturated sodium chloride solution. After the solution had been dried and evaporated down, the crude product was purified by chromatography over silica gel. The eluent used was initially dichloromethane/n-hexane and then pure dichloromethane. Yield: 82%; mp.: 85°–88° C.

250 MHz-$^1$H-NMR (in DMSO-$d_6$):

δ [ppm]=1.9–2.1 (m, 2H); 2.68 (t, 2H); 4.342 (t, 2H); 7.18 (t, 2H); 7.5–7.6 (m, 2H); 7.85 (s, 4H).

Intermediate 2.3

5-Aminooxy-1-(4-fluorophenyl)-1-pentyne 47.7 g (0.148 mol) of the phthalimidoether prepared above were added a little at a time to a mixture of 68 ml of ethanolamine and 40 ml of dichloromethane. After stirring for 2 hours at room temperature, a clear solution had formed. This was added to 300 ml of ice-cold, saturated sodium chloride solution. The mixture was extracted three times with 100 ml of dichloromethane, and the combined organic phases were washed once with sodium chloride solution, dried and evaporated down, Yield: 95% (oil).

250 MHz-$^1$H-NMR (in CDCl$_3$):

δ [ppm =1.8–2.0 (m, 2H); 2.47 (6, 2H); 3.8 (t, 2H); 5.4 (broad s, 2H); 6.9–7.1 (m, 2H); 7.35–7.45 (m, 2H).

EXAMPLE 3

2-[1-[[(E)-4-(2-Thienyl)-3-butenyloxy]-imino]-butyl]-3-hydroxy-5-(2H-tetrahydropyran-4-yl)-cyclohex-2-en-1-one

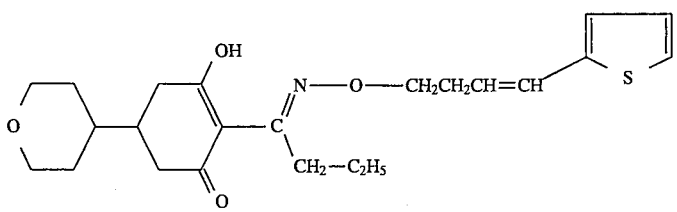

A mixture of 35 g (0.13 mol) of 2-butyryl-3-hydroxy-5-(2H-tetrahydropyran-4-yl)-2-cyclohexene-1-one and 24 g (0.14 mol) of O-[(E)-4-(2-thienyl)-3-butenyl]-hydroxylamine in 300 ml of methanol was stirred for 16 hours. It was evaporated down under reduced pressure and the residue was taken up in 1,000 ml of 10% strength by weight sodium hydroxide solution. The solution was extracted with three times 200 ml of methylene chloride, and the aqueous phase was brought to pH 1 with concentrated hydrochloric acid while cooling with ice. The aqueous phase was then extracted with three times 200 ml of ether, and the organic phase was dried over magnesium sulfate and evaporated down under reduced pressure. The crude product was purified by chromatography (100 g of silica gel; 30×15 cm column; mobile phase: ethyl acetate). Yield: 85%.

200 MHz-$^1$H-NMR (in $CDCl_3$): δ [ppm]=0.95 (t, 3H); 1.17– 1.96 (m, 9H); 2.13 (m, 1H); 2.36 (m, 1H); 2.43–2.70 (m, 3H); 2.88 (m, 2H), 3.36 (t, 2H), 4.02 (d, 2H), 4.15 (t, 2H), 6.00 (dt, 1H), 6.60 (d, 1H), 6.80–7.20 (m, 3H), 14.75 (s, 1H).

Intermediate 3.1

(E)-4-Bromo-1-(2-thienyl)-1-butene 225 g (1.46 mol) of cyclopropyl-2-thienylcarbinol were added dropwise to 972 ml of 48% strength hydrobromic acid at from 5° to 10° C. in the course of 1 hour. After 2 hours at room temperature, the organic phase was separated off and the aqueous solution was extracted with three times 300 ml of dichloromethane. The combined organic phases were washed neutral with dilute sodium hydroxide solution and water, dried over magnesium sulfate and evaporated down under reduced pressure. 322 g (94% corrected) of crude bromide (GC: 92%) were obtained. 250 MHz-$^1$H-NMR (in $CDCl_3$): δ [ppm]=2.65–2.80 (m, 2H), 3.46 (t, 2H), 5.90–6.10 (m, 1H), 6.61 (d, 1H), 6.80–7.00 (m, 2H), 7.14 (d, 1H).

Intermediate 3.2

N-[(E)-4-(2-Thienyl)-3-butenyloxy]-phthalimide 190 ml (1.37 mol) of triethylamine were added dropwise, at from 20° to 25° C. in the course of 2.5 hours, to a mixture of 283 g (1.30 mol) of the bromide prepared above, 1300 ml of N-methyl-2-pyrrolidinone, 10 g of potassium iodide and 212 g (1.30 mol) of N-hydroxyphthalide. After 4 hours at from 20° C. to 25° C., the mixture was poured into 4,000 ml of ice water, and 5,000 ml of 10% strength by weight sodium hydroxide solution were added a little at a time. Extraction was then carried out with four times 500 ml of ethyl acetate. The combined ethyl acetate phases were washed neutral with dilute sodium hydroxide solution and water, dried over magnesium sulfate and evaporated down under reduced pressure. The crude product was purified by chromatography (1,000 g of silica gel; 30×15 cm column; mobile phase: 7:3 n-hexane/dichloromethane). Yield: 29%; mp.: 69°–71° C. (isopropanol).

250 MHz-$^1$H-NMR (in $d_6DM50$): δ [ppm]=2.55–2.70 (m, 2H), 4.28 (t, 2H), 6.00–6.20 (m, 1H), 6.77 (d, 1H), 7.00 (m, 2H), 7.35 (m, 1H), 7.87 (s, 4H).

Intermediate 3.3

O-[(E)-4-(2-Thienyl)-3-butenyl]-hydroxylamine

A mixture of 90.2 g (0.30 mol) of the phthalimidoether prepared above and 136 ml of ethanolamine was stirred for 3 hours at 60° C. The cold reaction mixture was poured into 200 ml of ice water. 200 ml of saturated sodium chloride solution were added, and the hydrolysis product was extracted with three times 300 ml of dichloromethane. The combined organic phases were then washed with three times 100 ml of saturated sodium chloride solution, dried over magnesium sulfate and evaporated down under reduced pressure. Yield: 89%.

250 MHz-$^1$H-NMR (in $CDCl_3$): δ [ppm]=2.40–2.55 (m, 2H), 3.78 (t, 2H), 5.40 (bs, 2H), 5.95–6.20 (m, 1H), 6.57 (d, 1H), 6.80–7.15 (m, 3H).

EXAMPLE 4

2-[1-[[2-(2-Fluorobenzoyloxy)-ethoxy]-imino]-butyl-2-hydroxy-5-(2H-tetrahydropyran-4-yl)-2-cyclohexen-1-one

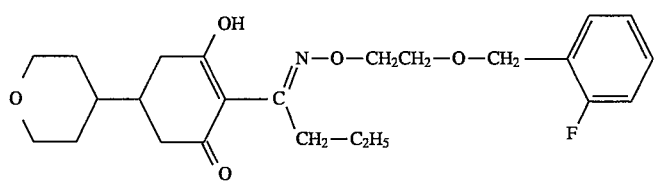

A mixture of 4.0 g (10 mmol) of 2-butyryl-3-hydroxy-5-(2H-tetrahydropyran-4-yl)-2-cyclohexen-1-one and 2.6 g (14 mmol) of O-[2-(2-fluorobenzyloxy)-ethyl]-hydroxylamine in 100 ml of methanol was stirred for 24 hours. The reaction mixture was evaporated down under reduced pressure and the crude product was chromatographed over 100 g of silica gel (column 30×4 cm; mobile phase: ether). Yield: 54%.

300 MHz-$^1$H-NMR (in $CDCl_3$): δ [ppm]=0.93 (t, 3H), 1.20– 1.77 (m, 7H), 1.90 (m, 1H), 2.23 (m, 2H), 2.58 (m, 2H), 2.92 (m, 2H), 3.38 (t, 2H), 3.80 (m, 2H), 4.03 (m, 2H), 4.25 (m, 2H), 4.68 (s, 2H), 6.93–7.50 (m, 4H), 14.30 (s, 1H).

Intermediate 4.1

N-[2-(2-Fluorobenzyloxy)-ethoxy]-phthalimide 108 ml of triethylamine were added dropwise, at from 20° to 25° C. in the course of 1 hour, to a mixture of 165 g (0.71 mol) of 1-bromo-2-(2-fluorobenzyloxy)-ethane, 116 g (0.7 mol) of N-hydroxyphthalimide and 710 ml of N-methyl-2-pyrrolidinone. After 5 hours at 60° C., the cold reaction mixture was poured into 200 ml of ice water, and the precipitate was filtered off under suction, washed with water and isopropanol and dried under reduced pressure over phosphorus pentoxide. Yield: 82%.

Mp.: 62°–64° C.

250 MHz-$^1$H-NMR (in $d_6$-DMSO): δ [ppm]=3.85 (m, 2H), 4.35 (m, 1H), 4.54 (s, 2H), 7.10–7.40 (m, 4H), 7.88 (s, 4H). Intermediate 4.2
O-[2-(2-Fluorobenzyloxy)-ethyl]-hydroxylamine 184 g (0.58 mol) of the phthalimidoether prepared above were introduced a little at a time into 270 ml of ethanolamine. After 3 hours at 60° C., the cold reaction mixture was poured into 1,000 ml of ice water. The hydrolysis product was extracted with three times 800 ml of dichloromethane. The combined organic phases were washed with 200 ml of saturated sodium chloride solution, dried over magnesium sulfate and evaporated down under reduced pressure. Yield: 91%.

$^1$H-NMR (250 MHz, CDCl$_3$): δ [pm]=3.70 (dd, 2H), 3.85 (dd, 2H), 4.54 (s, 2H), 5.50 (bs, 2H), 7.00–7.50 (m, 4H).

In view of the intended use of the novel herbicides, cyclohexenone derivatives of the formula II are suitable, their substituents having the following specific meanings:
$R^a$ is straight-chain or branched $C_1$–$C_6$-alkyl, such as methyl, ethyl, n-propyl, isopropyl, n-butyl, sec-butyl, isobutyl, tert-butyl, n-pentyl or n-hexyl, in particular ethyl or propyl;
$R^b$ is hydrogen;
one equivalent of an agriculturally useful cation, for example an alkali metal cation, such as sodium or potassium, one equivalent of an alkaline earth metal cation, such as calcium, magnesium or barium, a manganese, copper, zinc or iron cation, ammonium cations having, if desired, from one to three substituents selected from the group consisting of from one to three $C_1$–$C_4$-alkyl radicals, from one to three hydroxy-$C_1$–$C_4$-alkyl radicals and one phenyl or benzyl radical, eg. tetraalkyl- or benzyltrialkylammonium cations, phosphonium cations, sulfonium cations, such as trialkylsulfonium cations, or sulfonium cations;
$C_3$–$C_8$alkylcarbonyloxy, such as methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy, 1,2-dimethylpropylcarbonyloxy, 2,2-dimethylpropylcarbonyloxy, 1-ethylpropylcarbonyloxy, n-hexylcarbonyloxy, 1-methylpentylcarbonyloxy, 2-methylpentylcarbonyloxy, 3-methylpentylcarbonyloxy, 4-methylpentylcarbonyloxy, 1,1-dimethylbutylcarbonyloxy, 1,2-dimethylbutylcarbonyloxy, 1,3-dimethylbutylcarbonyloxy, 2,2-dimethylbutylcarbonyloxy, 2,3-dimethylbutylcarbonyloxy, 3,3-dimethylbutylcarbonyloxy, 1-ethylbutylcarbonyloxy, 2-ethylbutylcarbonyloxy, 1,1,2-trimethylpropylcarbonyloxy, 1,2,2-trimethylpropylcarbonyloxy, 1-ethyl-1-methylpropylcarbonyloxy or 1-ethyl-2-methylpropylcarbonyloxy;
the benzoyl group or a derivative substituted in the phenyl nucleus by one to five halogen atoms;
straight-chain or branched $C_1$–$C_{10}$-alkylsulfonyl, in particular $C_1$–$C_6$-alkylsulfonyl, such as methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;
the benzenesulfonyl group or a derivative substituted in the phenyl nucleus by one to five halogen atoms;
straight-chain or branched $C_1$–$C_{10}$alkylphosphonyl, in particular $C_1$–$C_6$-alkylphosphonyl, such as methylphosphonyl, ethylphosphonyl, n-propylphosphonyl, 1-methylethylphosphonyl, n-butylphosphonyl, 1-methylpropylphosphonyl, 2-methylpropylphosphonyl, 1,1-dimethylethylphosphonyl, n-pentylphosphonyl, 1-methylbutylphosphonyl, 2-methylbutylphosphonyl, 3-methylbutylphosphonyl, 1,1-dimethylpropylphosphonyl, 1,2-dimethylpropylphosphonyl, 2,2-dimethylpropylphosphonyl, 1-ethylpropylphosphonyl, hexylphosphonyl, 1-methylpentylphosphonyl, 2-methylpentylphosphonyl, 3-methylpentylphosphonyl, 4-methylpentylphosphonyl, 1,1-dimethylbutylphosphonyl, 1,2-dimethylbutylphosphonyl, 1,3-dimethylbutylphosphonyl, 2,2-dimethylbutylphosphonyl, 2,3-dimethylbutylphosphonyl, 3,3-dimethylbutylphosphonyl, 1-ethylbutylphosphonyl, 2-ethylbutylphosphonyl, 1,1,2-trimethylpropylphosphonyl, 1,2,2-trimethylpropylphosphonyl, 1-ethyl-1-methylpropylphosphonyl or 1-ethyl-2-methylpropylphosphonyl;
the benzenephosphonyl group or a derivative substituted in the phenyl nucleus by one to five halogen atoms;
$R^c$ is hydrogen; cyano, formyl;
straight-chain or branched $C_1$–$C_6$-alkyl as stated above, in particular ethyl, n-propyl or isopropyl;
$C_1$–$C_4$-alkoxy-$C_1$–$C_4$-alkyl, such as methoxymethyl, ethoxymethyl, n-propoxymethyl, 1-methoxyethyl, 2-methoxyethyl, 1-ethoxyethyl, 2-ethoxyethyl, 2-propoxyethyl, 1-methoxypropyl, 2-methoxypropyl, 3-methoxypropyl, 1-ethoxypropyl, 2-ethoxypropyl, 3-ethoxypropyl, 1-methoxybutyl, 2-methoxybutyl, 3-methoxybutyl, 4-methoxybutyl, 1-ethoxybutyl, 2-ethoxybutyl, 3-ethoxybutyl, 4-ethoxybutyl, 1,3-dimethoxypropyl, preferably methoxymethyl or 2-ethoxyethyl;
$C_1$–$C_4$-alkylthio-$C_1$–$C_4$-alkyl, such as methylthiomethyl, ethylthiomethyl, 1-methylthioethyl, 2-methylthioethyl, 1-ethylthioethyl, 2-ethylthioethyl, 1-methylthiopropyl, 2-methylthiopropyl, 3-methylthiopropyl, 1-ethylthiopropyl, 2-ethylthiopropyl, 3-ethylthiopropyl, 1-methylthiobutyl, 2-methylthiobutyl, 3-methylthiobutyl, 4-methylthiobutyl, 1-ethylthiobutyl, 2-ethylthiobutyl, 3-ethylthiobutyl, 4-ethylthiobutyl, preferably 2-ethylthiopropyl;
phenoxy-$C_1$–$C_6$-alkyl, phenylthio-$C_1$–$C_6$-alkyl, pyridyloxy-$C_1$–$C_6$-alkyl or pyridylthio-$C_1$–$C_6$-alkyl, where the phenyl and pyridyl rings may be unsubstituted or may carry from one to three radicals selected from the group consisting of nitro, cyano, halogen, such as fluorine, chlorine, bromine and iodine, in particular fluorine and chlorine, straight-chain or branched $C_1$–$C_4$-alkyl, such as methyl, ethyl, n-propyl, isopropyl, n-butyl or tert-butyl, partially or completely halogenated $C_1$–$C_4$-alkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trifluoromethyl, $C_1$–$C_4$-alkoxy, such as methoxy, ethoxy, n-propoxy, isopropoxy, n-butoxy or tert-butoxy, preferably methoxy or ethoxy, partially or completely halogenated $C_1$–$C_4$-alkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy, $C_1$–$C_4$-alkylthio, such as methylthio, ethylthio, n-propylthio, isopropylthio, n-butylthio or tert-butylthio, preferably methylthio or ethylthio, $C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, preferably prop-2-enyl or but-3-enyl, $C_3$–$C_6$-alkenyloxy, such as prop-2-en-1-yloxy, n-buten-4-yloxy, n-buten-3-yloxy, 1-methylprop-2-en-1-yloxy, 2-methylprop-2-en-1-yloxy, n-penten-3-yloxy, n-penten-4-yloxy, n-penten-5-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethyl-2-en-1-yloxy, 1-ethylprop-2-en-1-yloxy, n-hex-2-en-1-yloxy, n-hex-3-en-1-yloxy, n-hex-4-en-1-yloxy, n-hex-5-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-2-en-1-yloxy, 1,2-dimethylbut-3-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-2-en-1-yloxy, 2,3-dimethylbut-3-en-1-yloxy, 3,3-dimethylbut-2-en-1-yloxy, 1-ethylbut-2-en-1-yloxy, 1-ethylbut-3-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy and 1-ethyl-2-methylprop-2-en-1-yloxy, preferably prop-2-en-1-yloxy and but-2-en-1-yloxy, $C_3$–$C_6$-alkynyl, such as prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pentyn-5-yl, pent-2-yn-1-yl, pent-2-yn-4-yl, pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-ynyl, $C_3$–$C_6$-alkynyloxy, such as prop-2-yn-3-yloxy, n-but-1-yn-4-yloxy, n-but-2-yn-1-yloxy, n-pent-1-yn-3-yloxy, n-pent-1-yn-4-yloxy, n-pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-3-yloxy, 3-methylpent-1-yn-4-yloxy, 3-methylpent-1-yn-5-yloxy, 4-methylpent-2-yn-4-yloxy and 4-methylpent-2-yn-5-yloxy, preferably prop-2-ynyloxy, or a group $NR^gR^h$, where $R^h$ is hydrogen, straight-chain or branched $C_1$–$C_4$-alkyl as stated above, $C_3$–$C_6$-alkenyl as stated above or $C_3$–$C_6$-alkynyl as stated above, preferably hydrogen, and $R^g$ is hydrogen, straight-chain or branched $C_1$–$C_4$-alkyl as stated above, $C_3$–$C_6$-alkenyl as stated above, $C_3$–$C_6$-alkynyl as stated above, $C_1$–$C_6$-acyl, such as methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular methylcarbonyl or 1,1-dimethylethylcarbonyl, or benzoyl which may be unsubstituted or may carry from one to three substituents selected from the group consisting of nitro, cyano, halogen as stated above, in particular fluorine and chlorine, and straight-chain or branched $C_1$–$C_4$-alkyl as stated above, partially or completely halogenated $C_1$–$C_4$-alkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably trifluoromethyl, $C_1$–$C_4$-alkoxy as stated above and $C_1$–$C_4$-alkylthio as stated above;

particularly preferred phenoxy-$C_1$–$C_6$-alkyl, phenylthio-$C_1$–$C_6$-alkyl, pyridyloxy-$C_1$–$C_6$-alkyl or pyridylthio- $C_1$–$C_6$-alkyl groups are phenoxymethyl, phenoxyethyl, phenoxypropyl, phenoxybutyl, 4-fluorophenoxyethyl, 2-(4-fluorophenoxy)-propyl, 4-trifluoromethylphenoxyethyl, 2-(4-trifluoromethylphenoxy)-propyl, phenylthiomethyl, phenylthioethyl, phenylthiopropyl, phenylthiobutyl, 4-fluorophenylthioethyl, 2-(4-fluorophenylthio)-propyl, 4-trifluoromethylphenylthioethyl and 2-(4-trifluoromethylphenylthio)-propyl, in particular 4-fluorophenylthioethyl and 4-trifluoromethylphenylthioethyl;

$C_3$–$C_7$-cycloalkyl or $C_5$–$C_7$-cycloalkenyl, such as cyclopropyl, cyclobutyl, cyclopentyl, cyclohexyl, cycloheptyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl or cyclohept-4-enyl, where the carbocyclic radicals may each be unsubstituted or may carry from one to three radicals selected from the group consisting of hydroxyl, halogen as stated above, in particular fluorine or chlorine, straight-chain or branched $C_1$–$C_4$-alkyl as stated above, in particular methyl or ethyl, partially or completely halogenated $C_1$–$C_4$-alkyl as stated above, in particular trifluoromethyl, $C_1$–$C_4$-alkoxy as stated above, in particular methoxy, $C_1$–$C_4$-alkylthio as stated above, in particular methylthio and ethylthio, benzylthio, $C_1$–$C_4$-alkylsulfonyl, such as methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, preferably methylsulfonyl, and $C_1$–$C_4$-alkylsulfinyl, such as methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl, preferably methylsulfinyl;

among the substituted $C_3$–$C_7$-cycloalkyl and $C_5$–$C_7$-cycloalkenyl groups, 1-methylthiocyclohexyl, 1-ethylthiocyclopropyl, 4-methylcyclohexyl, 4-methylcyclohex-3-enyl, 3-ethylthio-4-hydroxy-4-methylcyclohexyl and 3,4-dihydroxycyclohexyl are particularly preferred, especially 1-methylthiocyclopropyl, 1-ethylthiocyclopropyl and 3,4-dihydroxycyclohexyl;

5-membered heterocycloalkyl, such as tetrahydrofuran-2-yl, tetrahydrofuran-3-yl, tetrahydrothien-2-yl, tetrahydrothien-3-yl, pyrrolidin-2-yl, pyrrolidin-3-yl, isoxazolidin-3-yl, isoxazolidin-4-yl, isoxazolidin-5-yl, isothiazolidin-3-yl, isothiazolidin-4-yl, isothiazolidin-5-yl, pyrazolidin-3-yl, pyrazolidin-4-yl, pyrazolidin-5-yl, oxazolidin-2-yl, oxazolidin-4-yl, oxazolidin-5-yl, thiazolidin-2-yl, thiazolidin-4-yl, thiazolidin-5-yl, imidazolidin-2-yl, imidazolidin-4-yl, 1,2,4-oxadiazolidin-2-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, dioxolanyl or dithiolanyl, in particular tetrahydrofuran-2-yl, tetrahydrofuran-3-yl and dioxolanyl, where the heterocyclic radicals may each be un substituted or may carry from one to three radicals selected from the group consisting of straight-chain or branched $C_1$–$C_4$-alkyl as stated above, in particular methyl and ethyl, partially or completely halogenated $C_1$–$C_4$-alkyl as stated above, in particular trifluoromethyl, $C_1$–$C_4$-alkoxy as stated above, in particular methoxy, and $C_1$–$C_4$-alkylthio as stated above, in particular methylthio;

a 6-membered or 7-membered heterocyclic structure, such as tetrahydrothiopyran-2-yl, tetrahydrothiopyran-3-yl, tetrahydrothiopyran-4-yl, tetrahydropyran-2-yl, tetrahydropyran-3-yl, tetrahydropyran-4-yl, 5,6-dihydro-2H-thiopyran-2-yl, 5,6-dihydro-2H-thiopyran-3-yl, 5,6-dihydro-2H-pyran-4-yl, 5,6-dihydro-2H-thiopyran-5-yl, 5,6-dihydro-2H-thiopyran-6-yl, 5,6-dihydro-2H-pyran-2-yl, 5,6-dihydro-2H-pyran-3-yl, 5,6-dihydro-2H-pyran-4-yl, 5,6-dihydro-2H-pyran-5-yl, 5,6-dihydro-2H-pyran-6-yl or dioxepan-5-yl, in particular tetrahydrothiopyran-3-yl, tetrahydropyran-3-yl or tetrahydropyran-4-yl, where the heterocyclic structures may each be unsubstituted or may carry from one to three radicals selected from the group consisting of hydroxyl, halogen as stated above, in particular chlorine and bromine, straight-chain or branched $C_1$–$C_4$-alkyl as stated above, in particular methyl or ethyl, partially or completely halogenated $C_1$–$C_4$-alkyl as stated above, in particular trifluoromethyl, $C_1$–$C_4$-alkoxy as stated above, in particular methoxy, and $C_1$–$C_4$-alkylthio as stated above, in particular methylthio and ethylthio;

a 5-membered heteroaromatic radical containing from one to three hetero atoms selected from the group consisting of one or two nitrogen atoms and one oxygen or sulfur atom, for example 2-furyl, 3-furyl, 2-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl or 1,3,4-triazol-2-yl, in particular isoxazolyl or pyrazolyl, where the heteroaromatic radical may be unsubstituted or may carry from one to three radicals selected from the group consisting of cyano, halogen as stated above, in particular fluorine or chlorine, straight-chain or branched $C_1$–$C_4$-alkyl as stated above, in particular methyl, ethyl and isopropyl, partially or completely halogenated $C_1$–$C_4$-alkyl as stated above, in particular trifluoromethyl, $C_1$–$C_4$-alkoxy as stated above, in particular methoxy, partially or completely halogenated $C_1$–$C_4$-alkoxy as stated above, in particular trifluoromethoxy, $C_1$–$C_4$-alkylthio, in particular methylthio, $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular 1-methylethenyl, $C_2$–$C_6$-alkenyloxy, such as ethenyloxy, prop-2-en-1-yloxy, n-buten-4-yloxy, n-buten-3-yloxy, 1-methylprop-2-en-1-yloxy, 2-methylprop-2-en-1-yloxy, n-penten-3-yloxy, n-penten-4-yloxy, n-penten-5-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1- yloxy, 3-methylbut-3-en-1-yloxy, 1,1-dimethylprop-2-en-1-yloxy, 1,2-dimethylprop-2-en-1-yloxy, 1-ethylprop-2-en-1-yloxy, n-hex-2-en-1-yloxy, n-hex-3-en-1-yloxy, n-hex-4-en-1-yloxy, n-hex-5-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-2-en-1-yloxy, 1,2-dimethylbut-3-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-2-en-1-yloxy, 2,3-dimethylbut-3-en-1-yloxy, 3,3-dimethylbut-2-en-1-yloxy, 1-ethylbut-2-en-1-yloxy, 1-ethylbut-3-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy and 1-ethyl-2-methylprop-2-en-1-yloxy, preferably prop-2-en-1-yloxy, $C_3$–$C_6$-alkynyloxy, such as prop-2-yn-3-yloxy, n-but-2-yn-4-yloxy, n-but-2-yn-1-yloxy, n-pent-1-yn-3-yloxy, n-pent-1-yn-4-yloxy, n-pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-3-yloxy, 3-methylpent-1-yn-4-yloxy, 3-methylpent-1-yn-5-yloxy, 4-methylpent-2-yn-4-yloxy and 4-methylpent-2-yn-5-yloxy, preferably prop-2-ynyloxy, and $C_1$–$C_4$-alkoxy-$C_1$–$C_4$-alkyl, such as methoxymethyl, ethoxymethyl, n-propoxymethyl, (1-methylethoxy)-methyl, n-butoxymethyl, (1-methylpropoxy)-methyl, (2-methylpropoxy)-methyl, (1,1-dimethylethoxy)-methyl, methoxyethyl, ethoxyethyl, n-propoxyethyl, (1-methylethoxy)-ethyl, n-butoxyethyl, (1-methylpropoxy)-ethyl, (2-methylpropoxy)-ethyl, (1,1-dimethylethoxy)-ethyl, 3-methoxypropyl, 2-methoxypropyl or 2-ethoxypropyl, preferably methoxymethyl or ethoxyethyl, phenyl or pyridyl, both of which may be un substituted or may carry from one to three radicals selected from the group consisting of nitro, cyano, formyl, halogen as stated above, in particular fluorine and chlorine, straight-chain or branched $C_1$–$C_4$-alkyl as stated above, in particular methyl and ethyl, partially or completely halogenated $C_1$–$C_4$-alkyl as stated above, in particular trifluoromethyl, $C_1$–$C_4$-alkoxy as stated above, in particular methoxy, partially or completely halogenated $C_1$–$C_4$-alkoxy as stated above, in particular trifluoromethoxy, $C_1$–$C_4$-alkylthio as stated above, in particular methylthio, $C_3$–$C_6$-alkenyl as stated above, in particular $C_3$- or $C_4$-alkenyl, preferably prop-2-enyl, $C_3$–$C_6$-alkenyloxy as stated above, in particular $C_3$- or $C_4$-alkenyloxy, preferably prop-2-enyloxy, $C_3$–$C_6$-alkynyl as stated above, in particular $C_3$- or $C_4$-alkynyl, preferably prop-2-ynyl, $C_3$–$C_6$-alkynyloxy as stated above, in particular $C_3$- or $C_4$-alkynyloxy, preferably prop-2-ynyloxy, and $NR^gR^h$, where $R^g$ and $R^h$ have the abovementioned meanings, preferably hydrogen, acetyl or benzoyl;

particularly preferred phenyl and pyridyl groups are phenyl, 4-ethylphenyl, 4-propargyloxyphenyl, 2,4,6-trimethylphenyl, 4-benzoylamino-3-fluorophenyl, 4-formylphenyl and pyridyl;

W is a $C_1$–$C_6$-alkylene, a $C_3$–$C_6$-alkenylene or a $C_3$–$C_6$-alkynylene chain, such as methylene, ethylene, propylene, butylene, pentylene, hexylene, propenylene, prop-2-enylene, butenylene, but-2-enylene, but-3-enylene, pentenylene, pent-2-enylene, pent-3-enylene, pent-4-enylene, hex-1-enylene, hex-2-enylene, hex-3-enylene, hex-4-enylene, hex-5-enylene, prop-2-ynylene, but-2-ynylene, but-3-ynylene, pent-2-ynylene, pent-3-ynylene, pent-4-ynylene, hex-2-ynylene, hex-3-ynylene, hex-4-ynylene or hex-5-ynylene, where these chains may, if desired, furthermore carry from one to three radicals selected from the group consisting of from one to three halogen atoms as stated above, in particular fluorine or chlorine, from one to three $C_1$–$C_3$-alkyl substituents, such as methyl, ethyl, n-propyl and isopropyl, in particular methyl and ethyl, and one methylene substituent; in the case of the unsaturated chains, both the cis and the trans form may occur; propylene, butylene, prop-2-enylene, but-2-enylene, but-3-enylene and but-3-ynylene are particularly preferred;

$C_3$–$C_6$-alkylene or $C_4$–$C_6$-alkenylene, both of which may be unsubstituted or may carry from one to three $C_1$–$C_4$-alkyl radicals, in each case a methylene group being replaceable with an oxygen or sulfur atom, a sulfoxyl or sulfonyl group or a group —N($R^i$)—, where $R^i$ is hydrogen, straight-chain or branched $C_1$–$C_4$-alkyl as stated above, in particular methyl or ethyl, $C_3$–$C_6$-alkenyl as stated above, in particular prop-2-enyl or but-2-enyl, or $C_3$–$C_6$-alkynyl as stated above, in particular prop-2-ynyl or but-2-ynyl, for example 3-oxapropylene, 3-azapropylene, 3-thiapropylene, 3-oxo-3-thiapropylene, 3,3-dioxo-3-thiapropylene, 3-oxabutylene, 3-azabutylene, 3-thiabutylene, 3-oxo-3-thiabutylene, 3,3-dioxo-3-thiabutylene, 4-oxabutylene, 4-azabutylene, 4-thiabutylene, 4-oxo-4-thiabutylene, 4,4-dioxo-4-thiabutylene, 4-oxabut-2-enylene, 4-azabut-2-enylene, 4-thiabut-2-enylene, 3-oxapentylene, 3-azapentylene, 3-thiapentylene, 3-oxo-3-thiapentylene, 3,3-dioxo-3-thiapentylene, 4-oxapentylene, 4-azapentylene, 4-thiapentylene, 4-oxo-4-thiapentylene, 4,4-dioxo-4-thiapentylene, 5-oxapentylene, 5-azapentylene, 5-thiapentylene, 5-oxo-5-thiapentylene, 5,5-dioxo-5-thiapentylene, 5-oxapent-3-enylene, 5-azapent-3-enylene, 5-thiapent-3-enylene, 3-oxahexylene, 3-azahexylene, 3-thiahexylene, 3-oxo-3-thiahexylene, 3,3-dioxo-3-thiahexylene, 4-oxahexylene, 4-azahexylene, 4-thiahexylene, 4-oxo-4-thiahexylene, 4,4-dioxo-4-thiahexylene, 5-oxahexylene, 5-azahexylene, 5-thiahexylene, 5-oxo-5-thiahexylene, 5,5-dioxo-5-thiahexylene, 6-oxahexylene, 6-azahexylene, 6-thiahexylene, 6-oxo-6-thiahexylene, 6,6-dioxo-6-thiahexylene, 6-oxahex-4-enylene, 6-azahex-4-enylene or 6-thiahex-4-enylene; in the case of the unsaturated chains, the double bonds may have either a cis or a trans configuration;

3-oxapropylene, 2-methyl-3-oxapropylene, 3-oxabutylene and 4-oxabutylene are particularly preferred;

$R^f$ is hydrogen; vinyl;

a group —CH═CH—Z, where Z is cyano;

halogen as stated above, in particular fluorine or chlorine;

straight-chain or branched $C_1$–$C_4$-alkyl as stated above, in particular methyl or 1,1-dimethylethyl;

partially or completely halogenated $C_1$–$C_4$-alkyl as stated above, in particular difluoromethyl, trifluoromethyl, 2,2,2-trifluoroethyl or pentafluoroethyl;

$C_3$–$C_6$-cycloalkyl, such as cyclopropyl, cyclobutyl, cyclopentyl or cyclohexyl, which may be unsubstituted or may carry from one to three substituents selected from the group consisting of hydroxyl, halogen as stated above, in particular fluorine and chlorine, straight-chain or branched $C_1$–$C_4$-alkyl as stated above, in particular methyl and isopropyl, partially or completely halogenated $C_1$–$C_4$-alkyl as stated above, in particular trifluoromethyl, and $C_1$–$C_4$-alkoxy as stated above, in particular methoxy; carboxyl;

$C_1$–$C_8$-alkoxycarbonyl, such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, 1,1-dimethylethoxycarbonyl, n-pentyloxycarbonyl, 1-methylbutoxycarbonyl, 2-methylbutoxycarbonyl, 3-ethylbutoxycarbonyl, 2,2-dimethylpropoxycarbonyl, 1-ethylpropoxycarbonyl, n-hexyloxycarbonyl, 1,1-dimethylpropoxycarbonyl, 1,2-dimethylpropoxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular methoxycarbonyl;

benzyloxycarbonyl;

phenyl, thienyl or pyridyl, where each of these radicals may be unsubstituted or may carry from one to three substituents selected from the group consisting of nitro, cyano, halogen as stated above, in particular fluorine and chlorine, straight-chain or branched $C_1$–$C_4$-alkyl as stated above, in particular methyl, ethyl and 1-methylethyl, partially or completely halogenated $C_1$–$C_4$-alkyl as stated above, in particular trifluoromethyl, $C_1$–$C_4$-alkoxy as stated above, in particular methoxy and ethoxy, partially or completely halogenated $C_1$–$C_4$-alkoxy as stated above, in particular difluoromethoxy and trifluoromethoxy, $C_1$–$C_4$-alkylthio as stated above, in particular methylthio, and $C_3$–$C_6$-cycloalkyl as stated above, where the cycloalkyl substituent may be unsubstituted or in turn may carry from one to three radicals selected from the group consisting of halogen as stated above, in particular fluorine and chlorine, straight-chain or branched $C_1$–$C_4$-alkyl as stated above, in particular methyl, partially or completely halogenated $C_1$–$C_4$-alkyl as stated above, in particular trifluoromethyl, and $C_1$–$C_4$-alkoxy as stated above, in particular methoxy; ethynyl which may carry one of the following radicals: straight-chain or branched $C_1$–$C_4$-alkyl as stated above, in particular methyl or ethyl, $C_3$–$C_6$-cycloalkyl, such as cyclopropyl, cyclobutyl, cyclopentyl or cyclohexyl, where the cycloalkyl radical may be unsubstituted or in turn may carry from one to three substituents selected from the group consisting of hydroxyl, halogen as stated above, in particular fluorine and chlorine, straight-chain or branched $C_1$–$C_4$-alkyl as stated above, in particular methyl and ethyl, partially or completely halogenated $C_1$–$C_4$-alkyl as stated above, in particular trifluoromethyl, and $C_1$–$C_4$-alkoxy as stated above, in particular methoxy, phenyl, thienyl or pyridyl, where each of these three aromatic radicals may be unsubstituted or may carry from one to three substituents selected from the group consisting of nitro, cyano, halogen as stated above, in particular fluorine and chlorine, straight-chain or branched $C_1$–$C_4$-alkyl as stated above, in particular methyl and ethyl, partially or completely halogenated $C_1$–$C_4$-alkyl as stated above, in particular trifluoromethyl, $C_1$–$C_4$-alkoxy as stated above, in particular methoxy, partially or completely halogenated $C_1$–$C_4$-alkoxy as stated above, in particular trifluoromethoxy and $C_1$–$C_4$-alkylthio as stated above, in particular methylthio;

and phenyl; halophenyl; dihalophenyl;

a 5-membered heteroaromatic group having from one to three hetero atoms selected from the group consisting of from one to three nitrogen atoms and one oxygen or sulfur atom, such as furanyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl, 1,3,4-oxadiazolyl, 1,3,4-thiadiazolyl or 1,3,4-triazolyl, in particular furanyl or thienyl;

a 6-membered heteroaromatic group having from one to four nitrogen atoms as hetero atoms, such as pyridyl, pyrimidyl, pyrazyl, pyridazinyl, triazyl or tetrazyl, in particular pyridyl or pyrimidyl, where the phenyl or hetaryl groups may be unsubstituted or may carry from one to three of the following radicals, but in the case of the hetaryl radicals no more than the number of substitutable carbon atoms present:

nitro;

$C_1$–$C_4$-alkoxy as stated above, in particular methoxy;

$C_1$–$C_4$-alkylthio as stated above, in particular methylthio;

partially or completely halogenated $C_1$–$C_4$-alkoxy, in particular $C_1$- or $C_2$-haloalkoxy as stated above, preferably trifluoromethoxy;

radicals Z and a radical —NR$^k$R$^l$, where

R$^k$ is hydrogen, straight-chain or branched $C_1$–$C_4$-alkyl as stated above, in particular methyl or ethyl, $C_3$–$C_6$-alkenyl as stated above, in particular prop-2-en-1-yl, or $C_3$–$C_6$-alkynyl as stated above, in particular prop-2-yn-1-yl, and R$^l$ is hydrogen, straight-chain or branched $C_1$–$C_4$-alkyl as stated above, in particular methyl or ethyl, $C_3$–$C_6$-alkenyl as stated above, in particular prop-2-en-1-yl, $C_3$–$C_6$-alkynyl as stated above, in particular prop-2-yn-1-yl, straight-chain or branched $C_1$–$C_6$-acyl, such as acetyl, propionyl or butyryl, or benzoyl which, if desired, in turn may furthermore carry from one to three substituents selected from the group consisting of nitro, cyano, halogen as stated above, in particular fluorine and chlorine, straight-chain or branched $C_1$–$C_4$-alkyl as stated above, in particular methyl, partially or completely halogenated $C_1$–$C_4$-alkyl as stated above, in particular trifluoromethyl, $C_1$–$C_4$-alkoxy as stated above, in particular methoxy and ethoxy, and $C_1$–$C_4$-alkylthio as stated above, in particular methylthio;

in the case of a plurality of radicals Z, the substituents may be identical or different.

Very particularly preferred cyclohexenone derivatives of the formula II whose toleration by crops can be improved by substituted 3-aminobenzo[b]thiophenes I are shown in Tables 1 to 8 below:

TABLE 1

II  ($R^b$, $R^d$, $R^e$ = H)

| No. | $R^a$ | $R^c$ | W | $R^f$ | Reference |
|---|---|---|---|---|---|
| A.001 | n-$C_3H_7$ | 2-(Ethylthio)propyl | —$CH_2CH_2$— | H | DE-A 2 822 304 |
| A.002 | $C_2H_5$ | 2-(Ethylthio)propyl | —$CH_2CH$=CCl— | H | US-A 4 440 566 |
| A.003 | n-$C_3H_7$ | 2-(Ethylthio)propyl | —$CH_2CH$=CCl— | H | US-A 4 440 566 |
| A.004 | n-$C_3H_7$ | Tetrahydrothiopyran-3-yl | —$CH_2CH_2$— | H | US-A 71 707 |
| A.005 | $C_2H_5$ | Tetrahydrothiopyran-3-yl | —$CH_2CH_2$— | H | EP-A 71 707 |
| A.006 | $CH_3$ | Tetrahydrothiopyran-3-yl | —$CH_2CH$=$CCH_3$— | H | EP-A 71 707 |
| A.007 | n-$C_3H_7$ | Tetrahydropyran-3-yl | —$CH_2CH_2$— | H | EP-A 71 707 |
| A.008 | $C_2H_5$ | Tetrahydropyran-4-yl | —$CH_2CH$=CCl— | H | EP-A 142 741 |
| A.009 | n-$C_3H_7$ | Pyridin-3-yl | —$CH_2CH_2$— | H | EP-A 66 195 |
| A.010 | $C_2H_5$ | 4-$CH_3$-phenyl | —$CH_2CH_2$— | H | DE-A 24 39 104 |
| A.011 | $C_2H_5$ | 4-$C_2H_5$-phenyl | —$CH_2CH$=$CCH_3$— | H | DE-A 38 08 072 |
| A.012 | $C_2H_5$ | 2,4,6-$(CH_3)_3$-phenyl | —$CH_2CH_2$— | H | EP-A 88 301 |
| A.013 | n-$C_3H_7$ | 4-$CH_3$-cyclohexyl | —$CH_2CH$=CCl— | H | EP-A 88 299 |
| A.014 | n-$C_3H_7$ | 4-$CH_3$-cyclohexyl | —$CH_2CH$=$CCH_3$— | H | EP-A 88 299 |
| A.015 | $C_2H_5$ | 3-Isopropyl-isoxazol-5-yl | —$CH_2CH$=$CCH_3$— | H | EP-A 238 021 |
| A.016 | n-$C_3H_7$ | 3-Isopropyl-isoxazol-5-yl | —$CH_2CH$=$CCH_3$— | H | EP-A 238 021 |
| A.017 | $C_2H_5$ | 4-(HC≡C—$CH_2$O)-phenyl | —$CH_2CH$=CCl— | H | EP-A 137 174 |
| A.018 | n-$C_3H_7$ | 4-$C_2H_5OCH_2$-phenyl | —$CH_2CH_2$— | H | EP-A 2 137 200 |
| A.019 | n-$C_3H_7$ | 3,4-$Br_2$-tetrahydropyran-3-yl | —$CH_2CH_2$— | H | EP-A 230 235 |
| A.020 | n-$C_3H_7$ | 3,4-$Br_2$-tetrahydropyran-3-yl | —$CH_2CH$=CCl— | H | EP-A 230 235 |
| A.021 | n-$C_3H_7$ | 2,6,6-$(CH_3)_3$-cyclohex-1-enyl | —$CH_2CH$=CCl— | H | EP-A 46 860 |
| A.022 | n-$C_3H_7$ | Cyclohexyl | —$CH_2CH_2$— | H | JP-A 540 191 945 |
| A.023 | n-$C_3H_7$ | Cyclohex-1-enyl | —$CH_2CH_2$— | H | EP-A 46 860 |
| A.024 | $CH_3$ | 4-$CH_3$-cyclohexyl | —$CH_2CH$=CCl— | H | EP-A 88 299 |
| A.025 | n-$C_3H_7$ | 4-$CF_3$-phenyl | —$CH_2CH_2$— | H | EP-A 137 174 |
| A.026 | $C_2H_5$ | 2,6,6-$(CH_3)_3$-cyclohex-1-enyl | —$CH_2CH$=CCl— | H | EP-A 46 860 |
| A.027 | n-$C_3H_7$ | 2-$CH_3$-thiazol-4-yl | —$CH_2CH$=$CCH_3$— | H | EP-A 125 094 |
| A.028 | n-$C_3H_7$ | 2-$CH_3$-thiazol-4-yl | —$CH_2CH$=CCl— | H | EP-A 125 094 |
| A.029 | n-$C_3H_7$ | 2,4,6-$(CH_3)_3$-cyclohexyl | —$CH_2CH_2$— | H | EP-A 88 299 |
| A.030 | n-$C_3H_7$ | 3-$C_2H_5$S-4-OH-4-$CH_3$-cyclohexyl | —$CH_2CH$=CH— | H | EP-A 228 598 |
| A.031 | $C_2H_5$ | 3,4-$(OH)_2$-cyclohexyl | —$CH_2CH_2$— | H | EP-A 228 598 |
| A.032 | n-$C_3H_7$ | 1-$CH_3$-pyrazol-3-yl | —$CH_2CH_2$— | H | EP-A 66 195 |
| A.033 | n-$C_3H_7$ | 1-$CH_3$-pyrrol-3-yl | —$CH_2CH$=CCl— | H | EP-A 66 195 |
| A.034 | n-$C_3H_7$ | 2-$CH_3$-thiazol-4-yl | —$CH_2CH$=CH— | H | EP-A 125 094 |
| A.035 | n-$C_3H_7$ | $(CH_3CH_2S)_2$-methyl | —$CH_2CH_2CH_2$— | H | EP-A 230 260 |
| A.036 | n-$C_3H_7$ | 1-Oxo-tetrahydrothiopyran-3-yl | —$CH_2CH_2$— | H | EP-A 115 808 |
| A.037 | n-$C_3H_7$ | 1,1-Dioxo-tetrahydrothiopyran-3-yl | $CH_2CH_2$— | H | EP-A 115 808 |
| A.038 | n-$C_3H_7$ | 1,1-Dioxo-tetrahydrothiopyran-3-yl | —$CH_2CH$=CH— | H | Proceedings Brit. Crop-Protection Conference-weeds 1985 Vol. 1 S. 93–98 |
| A.039 | $CH_3$ | 4-F-phenyl-thioethyl | —$CH_2CH_2$— | H | EP 254 514 |
| A.040 | $C_2H_5$ | 4-F-phenyl-thioethyl | —$CH_2CH_2$— | H | EP 254 514 |
| A.041 | $C_2H_5$ | 4-F-phenyl-thioethyl | —$CH_2CH$=CH— | H | EP 254 514 |
| A.042 | $C_2H_5$ | 4-F-phenyl-thioethyl | —$CH_2CH$=$CHCH_2$— | H | EP 254 514 |
| A.043 | n-$C_3H_7$ | 4-F-phenyl-thioethyl | —$CH_2CH$=CH— | H | EP 254 514 |
| A.044 | n-$C_3H_7$ | Formyl | —$CH_2CH_2$— | H | EP 319 835 |
| A.045 | n-$C_3H_7$ | 1-$CH_3$S-cyclopropyl | —$CH_2CH_2$— | H | EP 243 313 |
| A.046 | n-$C_3H_7$ | 1-$CH_3$S-cyclopropyl | —$CH_2C$(H)=C(Cl)— | H | EP 243 313 |
| A.047 | $C_2H_5$ | 1-$CH_3$S-cyclopropyl | —$CH_2C$(H)=C(Cl)— | H | EP 243 313 |
| A.048 | $C_2H_5$ | 1-$CH_3$S-cyclopropyl | —$CH_2C$(H)=C(Cl)— | H | EP 243 313 |
| A.049 | $C_2H_5$ | 1-$C_2H_5$S-cyclopropyl | —$CH_2C$(H)=C(Cl)— | H | EP 243 313 |

TABLE 1-continued

II ($R^b$, $R^d$, $R^e$ = H)

| No. | $R^a$ | $R^c$ | W | $R^f$ | Reference |
|---|---|---|---|---|---|
| A.050 | n-$C_3H_7$ | 1-$C_2H_5$S-cyclopropyl | $-CH_2C=C-$ (with H, Cl substituents) | H | EP 243 313 |
| A.051 | $C_2H_5$ | Tetrahydrothiopyran-3-yl | $-CH_2CH=CHCH_2-$ | 4-Cl-phenyl | EP-A 89 120 558 |
| A.052 | $C_2H_5$ | Tetrahydrothiopyran-3-yl | $-CH_2CH_2CH=CH-$ | 4-Cl-phenyl | EP-A 89 120 558 |
| A.053 | $C_2H_5$ | Tetrahydrothiopyran-3-yl | $-CH_2CH_2CH=CH-$ | 4-F-phenyl | EP-A 89 120 558 |
| A.054 | n-$C_3H_7$ | Tetrahydrothiopyran-3-yl | $-CH_2CH_2CH=CH-$ | 4-F-phenyl | EP-A 89 120 558 |
| A.055 | $C_2H_5$ | Tetrahydrothiopyran-3-yl | $-CH_2CH=CHCH_2-$ | Phenyl | EP-A 89 120 558 |
| A.056 | n-$C_3H_7$ | Tetrahydrothiopyran-3-yl | $-CH_2-$ | 5-Cl-thien-2 | EP-A 177 913 |
| A.057 | $C_2H_5$ | Tetrahydrothiopyran-3-yl | $-CH_2-$ | 5-Cl-thien-2 | EP-A 177 913 |
| A.058 | $C_2H_5$ | Tetrahydropyran-3-yl | $-CH_2-$ | 5-Cl-thien-2-yl | EP-A 177 913 |
| A.059 | n-$C_3H_7$ | Tetrahydropyran-4-yl | $-CH_2-$ | 5-Cl-thien-2-yl | EP-A 177 913 |
| A.060 | n-$C_3H_7$ | Tetrahydrothiopyran-3-yl | $-CH_2-$ | Thien-2-yl | EP-A 177 913 |
| A.061 | $CH_3$ | Tetrahydropyran-3-yl | $-CH_2-$ | Thien-2-yl | EP-A 177 913 |
| A.062 | $C_2H_5$ | Tetrahydropyran-4-yl | $-CH_2-$ | Thien-2-yl | EP-A 177 913 |
| A.063 | $C_2H_5$ | Tetrahydrothiopyran-3-yl | $-(CH_2)_4-$ | 4-F-phenyl | DE-A 38 38 309 |
| A.064 | n-$C_3H_7$ | Tetrahydrothiopyran-3-yl | $-(CH_2)_4-$ | 4-F-phenyl | DE-A 38 38 309 |
| A.065 | $C_2H_5$ | Tetrahydrothiopyran-3-yl | $-(CH_2)_4-$ | 4-F-phenyl | DE-A 38 38 309 |
| A.066 | n-$C_3H_7$ | Tetrahydrothiopyran-3-yl | $-(CH_2)_4-$ | 4-F-phenyl | DE-A 38 38 309 |
| A.067 | $C_2H_5$ | Tetrahydropyran-3-yl | $-(CH_2)_4-$ | 4-F-phenyl | DE-A 38 38 309 |
| A.068 | n-$C_3H_7$ | Tetrahydropyran-3-yl | $-(CH_2)_4-$ | 4-F-phenyl | DE-A 38 38 309 |
| A.069 | $C_2H_5$ | Tetrahydropyran-3-yl | $-(CH_2)_4-$ | 4-Cl-phenyl | DE-A 38 38 309 |
| A.070 | n-$C_3H_7$ | Tetrahydropyran-3-yl | $-(CH_2)_4-$ | 4-Cl-phenyl | DE-A 38 38 309 |
| A.071 | $C_2H_5$ | Tetrahydropyran-4-yl | $-(CH_2)_4-$ | 4-Cl-phenyl | |
| A.072 | n-$C_3H_7$ | Tetrahydropyran-4-yl | $-(CH_2)_4-$ | 4-Cl-phenyl | |
| A.073 | $C_2H_5$ | Tetrahydrothiopyran-3-yl | $-(CH_2)_4-$ | 4-Cl-phenyl | DE-A 38 38 309 |
| A.074 | n-$C_3H_7$ | Tetrahydrothiopyran-3-yl | $-(CH_2)_4-$ | 4-Cl-phenyl | DE-A 38 38 309 |

TABLE 2

($R^b$, $R^d$, $R^e$ = H)
($R^c$ = Tetrahydrothiopyran-3-yl)

| Example | $R^a$ | W | $R^f$ | Phys. data (NMR data in ppm) Mp. in °C. |
|---|---|---|---|---|
| A.075 | $C_2H_5$ | $-CH_2-CH=CH-$ | Phenyl | 103–104 |
| A.076 | n-$C_3H_7$ | $-CH_2-CH=CH-$ | Phenyl | 4.7(d, 2H), 6.3(dt, 1H), 6.7(d, 1H), 7.2–7.5(m, 5H) |
| A.077 | $C_2H_5$ | $-CH_2-CH=CH-$ | 4-Cl-phenyl | 106–107 |
| A.078 | n-$C_3H_7$ | $-CH_2-CH=CH-$ | 4-Cl-phenyl | 4.7(d, 2H), 6.3(dt, 1H), 6.65(d, 1H), 7.2–7.5(m, 4H) |
| A.079 | $C_2H_5$ | $-CH_2-CH=CH-$ | 4-F-phenyl | 90–91 |
| A.080 | n-$C_3H_7$ | $-CH_2-CH=CH-$ | 4-F-phenyl | 4.6(d, 2H), 6.2(dt, 1H), 6.6(d, 1H), 7.0(m, 2H), 7.4 (m, 2H) |
| A.081 | $C_2H_5$ | $-CH_2-CH=CH-$ | 2,4-$Cl_2$-phenyl | 123–124 |
| A.082 | n-$C_3H_7$ | $-CH_2-CH=CH-$ | 2,4-$Cl_2$-phenyl | 80–82 |
| A.083 | $C_2H_5$ | $-(CH_2)_3CH=CH-$ | Phenyl | 80–82 |
| A.084 | n-$C_3H_7$ | $-(CH_2)_3CH=CH-$ | Phenyl | 4.1(t, 2H), 6.2(dt, 1H), 6.4(d, 1H), 7.2–7.4(m, 5H) |
| A.085 | $C_2H_5$ | $-(CH_2)_3CH=CH-$ | 4-Cl-phenyl | 108–110 |
| A.086 | n-$C_3H_7$ | $-(CH_2)_3CH=CH-$ | 4-Cl-phenyl | 4.1(t, 2H), 6.2(dt, 1H), 6.4(d, 1H), 7.3(s, 4H) |
| A.087 | $C_2H_5$ | $-(CH_2)_3-$ | Phenyl | 4.0(t, 2H), 7.0–7.4(m, 5H) |
| A.088 | n-$C_3H_7$ | $-(CH_2)_3-$ | Phenyl | 4.0(t, 2H), 7.0–7.4(m, 5H) |
| A.089 | $C_2H_5$ | $-CH_2C(=CH_2)-CH_2-$ | Phenyl | 3.3(s, 2H), 4.4(s, 2H), 5.1 and 5.2(2s, 2H), 7.1–7.4 (m, 5H) |
| A.090 | n-$C_3H_7$ | $-CH_2C(=CH_2)-CH_2-$ | Phenyl | 3.35(s, 2H), 4.4(s, 2H), 5.0 and 5.1(2s, 2H), 7.0–7.4 (m, 5H) |

TABLE 2-continued ($R^b$, $R^d$, $R^e$ = H)
($R^c$ = Tetrahydrothiopyran-3-yl)

| Example | $R^a$ | W | $R^f$ | Phys. data (NMR data in ppm) Mp. in °C. |
|---|---|---|---|---|
| A.091 | $C_2H_5$ | $-CH_2CH=CH-$ | 4-Br-phenyl | 89–91 |
| A.092 | n-$C_3H_7$ | $-CH_2CH=CH-$ | 4-Br-phenyl | 97–99 |
| A.093 | $C_2H_5$ | $-CH_2CH=CH-$ | 4-$CH_3$-phenyl | 103–105 |
| A.094 | n-$C_3H_7$ | $-CH_2CH=CH-$ | 4-$CH_3$-phenyl | 88–90 |
| A.095 | $C_2H_5$ | $-CH_2CH=CH-$ | 4-$CF_3$-phenyl | 97–98 |
| A.096 | n-$C_3H_7$ | $-CH_2CH=CH-$ | 4-$CF_3$-phenyl | 4.75(d, 2H), 6.45(dt, 1H), 6.75(d, 1H), 7.4–7.8(m, 4H) |
| A.097 | $C_2H_5$ | $-CH_2CH=CH-$ | 4-$C_6H_5$O-phenyl | 4.65(d, 2H), 6.25(dt, 1H), 6.65(d, 1H), 6.9–7.6(3m, 9H) |
| A.098 | n-$C_3H_7$ | $-CH_2CH=CH-$ | 4-$C_6H_5$O-phenyl | 4.65(d, 2H), 6.25(dt, 1H), 6.65(d, 1H), 6.9–7.5 (3m, 9H) |
| A.099 | $C_2H_5$ | $-CH_2CH=C(CH_3)-$ | Phenyl | 77–78 |
| A.100 | n-$C_3H_7$ | $-CH_2CH=C(CH_3)-$ | Phenyl | 2.15(s, 3H), 4.75(d, 2H), 5.95(t, 1H), 7.2–7.6(m, 5H) |
| A.101 | $C_2H_5$ | $-CH_2CH=CH-$ | 2-Cl-phenyl | 97–98 |
| A.102 | n-$C_3H_7$ | $-CH_2CH=CH-$ | 2-Cl-phenyl | 87–89 |
| A.103 | $C_2H_5$ | $-(CH_2)_3-$ | 4-F-phenyl | 4.05(t, 2H), 6.9–7.2(m, 4H) |
| A.104 | n-$C_3H_7$ | $-(CH_2)_3-$ | 4-F-phenyl | 4.05(t, 2H), 6.9–7.2(m, 4H) |
| A.105 | $C_2H_5$ | $-(CH_2)_3-$ | 2,4-$Cl_2$-phenyl | 63–65 |
| A.106 | n-$C_3H_7$ | $-(CH_2)_3-$ | 2,4-$Cl_2$-phenyl | 4.05(t, 2H), 7.05–7.4(2m, 3H) |
| A.107 | $C_2H_5$ | $-(CH_2)_3-$ | 4-Br-phenyl | 4.05(t, 2H), 7.05 and 7.45(2m, 4H) |
| A.108 | n-$C_3H_7$ | $-(CH_2)_3-$ | 4-Br-phenyl | 4.05(t, 2H), 7.05 and 7.45(2m, 4H) |
| A.109 | $C_2H_5$ | $-(CH_2)_3-$ | 2-Cl-phenyl | 4.1(t, 2H), 7.05–7.4(m, 4H) |
| A.110 | n-$C_3H_7$ | $-(CH_2)_3-$ | 2-Cl-phenyl | 4.1(t, 2H), 7.05–7.4(m, 4H) |
| A.111 | $C_2H_5$ | $-(CH_2)_3-$ | 4-Cl-phenyl | 4.05(t, 2H), 7.0–7.4(m, 4H) |
| A.112 | n-$C_3H_7$ | $-(CH_2)_3-$ | 4-Cl-phenyl | 4.05(t, 2H), 7.0–7.4(m, 4H) |
| A.113 | $C_2H_5$ | $-CH_2CH=CH-$ | 3,5-$Cl_2$-phenyl | 75–77 |
| A.114 | n-$C_3H_7$ | $-CH_2CH=CH-$ | 3,5-$Cl_2$-phenyl | 70–73 |
| A.115 | $C_2H_5$ | $-CH_2CH_2CH(CH_3)-$ | Phenyl | 1.25(d, 3H), 3.95(m, 2H), 7.05–7.4(m, 5H) |
| A.116 | n-$C_3H_7$ | $-CH_2CH_2CH(CH_3)-$ | Phenyl | 1.25(d, 3H), 3.95(m, 2H), 7.05–7.4(m, 5H) |
| A.117 | $C_2H_5$ | $-(CH_2)_3-$ | 3,5-$Cl_2$-phenyl | 82–84 |
| A.118 | n-$C_3H_7$ | $-(CH_2)_3-$ | 3,5-$Cl_2$-phenyl | 4.05(t, 2H), 7.0–7.25(m, 3H) |
| A.119 | $C_2H_5$ | $-CH_2CH_2C(=CH_2)-$ | Phenyl | 4.15(t, 2H), 5.15(s, 1H), 5.25(s, 1H), 7.2–7.6(m, 5H) |
| A.120 | n-$C_3H_7$ | $-CH_2CH_2C(=CH_2)-$ | Phenyl | 4.15(t, 2H), 5.15(s, 1H), 5.25(s, 1H), 7.2–7.6(m, 5H) |
| A.121 | $CH_3$ | $-CH_2CH=CH-$ | 2,4-$Cl_2$-phenyl | 107–108 |
| A.122 | $CH_3$ | $-CH_2CH=CH-$ | 4-Cl-phenyl | 104–106 |
| A.123 | $C_2H_5$ | $-(CH_2)5-$ | 4-Cl-phenyl | 4.05(t, 2H), 7.0–7.4(2m, 4H) |
| A.124 | n-$C_3H_7$ | $-(CH_2)5-$ | 4-Cl-phenyl | 64–66 |
| A.125 | $C_2H_5$ | $-CH_2CH=CH-$ | 3,4-$Cl_2$-phenyl | 4.7(d, 2H), 6.3(dt, 1H), 6.55(d, 1H), 7.2–7.6(m, 3H) |
| A.126 | n-$C_3H_7$ | $-CH_2CH=CH-$ | 3,4-$Cl_2$-phenyl | 4.7(d, 2H), 6.3(dt, 1H), 6.55(d, 1H), 7.2–7.6(m, 3H) |
| A.127 | $C_2H_5$ | $-CH_2CH(CH_3)CH_2-$ | Phenyl | 0.95(d, 3H), 3.9(m, 2H), 7.0–7.5(m, 5H) |
| A.128 | n-$C_3H_7$ | $-CH_2CH(CH_3)CH_2-$ | Phenyl | 0.95(d, 3H), 3.9(m, 2H), 7.0–7.5(m, 5H) |
| A.129 | $C_2H_5$ | $-(CH_2)_3-$ | 3,4-$Cl_2$-phenyl | 4.05(t, 2H), 7.0–7.1 and 7.2–7.4(2m, 3H) |
| A.130 | n-$C_3H_7$ | $-(CH_2)_3-$ | 3,4-$Cl_2$-phenyl | 4.05(t, 2H), 6.95–7.1 and 7.2–7.45(2m, 3H) |
| A.131 | $C_2H_5$ | $-CH_2CH(CH_3)CH_2-$ | 4-F-phenyl | 0.95(d, 3H), 3.9(dd, 2H), 6.8–7.2(m, 4H) |
| A.132 | n-$C_3H_7$ | $-CH_2CH(CH_3)CH_2-$ | 4-F-phenyl | 0.95(d, 3H), 3.9(dd, 2H), 6.8–7.2(m, 4H) |
| A.133 | $C_2H_5$ | $-CH_2CH(CH_3)CH_2-$ | 4-Cl-phenyl | 0.9(d, 3H), 3.9(m, 2H), 7.0–7.4(2m, 4H) |
| A.134 | n-$C_3H_7$ | $-CH_2CH(CH))CH_2-$ | 4-Cl-phenyl | 0.9(d, 3H), 3.9(m, 2H), 7.0–7.4(2m, 4H) |
| A.135 | $C_2H_5$ | $-CH_2CH_2C(CH_3)_2-$ | 4-F-phenyl | 1.35(s, 6H), 3.85(t, 2H), 7.0 and 7.3(2m, 4H) |
| A.136 | n-$C_3H_7$ | $-CH_2CH_2C(CH_3)_2-$ | 4-F-phenyl | 1.35(s, 6H), 3.85(t, 2H), 7.0 and 7.3(2m, 4H) |
| A.137 | $C_2H_5$ | $-CH_2CH_2C(CH_3)_2-$ | 4-Cl-phenyl | 1.35(s, 6H), 3.85(t, 2H), 7.25(s, 4H) |
| A.138 | n-$C_3H_7$ | $-CH_2CH_2C(CH_3)_2-$ | 4-Cl-phenyl | 1.35(s, 6H), 3.85(t, 2H), 7.25(s, 4H) |
| A.139 | $C_2H_5$ | $-(CH_2)_6-$ | 4-Cl-phenyl | 1.15(t, 3H), 4.05(t, 2H), 7.1(d, 2H), 7.25(d, 2H) |
| A.140 | n-$C_3H_7$ | $-(CH_2)_6-$ | 4-Cl-phenyl | 0.95(t, 3H), 4.05(t, 2H), 7.1(d, 2H), 7.25(d, 2H) |
| A.141 | $C_2H_5$ | $-(CH_2)_6-$ | 4-F-phenyl | 1.1(t, 3H), 4.0(t, 2H) |
| A.142 | n-$C_3H_7$ | $-(CH_2)_6-$ | 4-F-phenyl | 0.95(t, 3H), 4.0(t, 2H) |
| A.143 | $C_2H_5$ | $-(CH_2)_5-$ | 4-F-phenyl | 1.1(t, 3H), 4.05(t, 2H), 6.95 and 7.1(2m, 4H) |
| A.144 | n-$C_3H_7$ | $-(CH_2)_5-$ | 4-F-phenyl | 0.9(t, 3H), 4.05(t, 2H), 6.95 and 7.1(2m, 4H) |
| A.145 | $C_2H_5$ | $-CH_2CH(CH_3)-(CH_2)_3-$ | 2-$CH_3$-phenyl | 2.3(s, 3H), 3.95(t, 1H), 7.1(m, 4H) |
| A.146 | n-$C_3H_7$ | $-CH_2CH(CH_3)-(CH_2)_3-$ | 2-$CH_3$-phenyl | 2.3(s, 3H), 3.9(t, 1H), 7.05(m, 4H) |
| A.147 | $C_2H_5$ | $-CH_2CH=CH-$ | 3-Br-phenyl | 96–98 |
| A.148 | n-$C_3H_7$ | $-CH_2CH=CH-$ | 3-Br-phenyl | 0.95(t, 3H), 4.65(d, 2H), 6.3(dt, 1H), 6.6(d, 1H), 7.1–7.6(m, 4H) |
| A.149 | $C_2H_5$ | $-CH_2CH=CH-$ | 3-Cl-phenyl | 98–100 |
| A.150 | n-$C_3H_7$ | $-CH_2CH=CH-$ | 3-Cl-phenyl | 1.0(t, 3H), 4.7(d, 2H), 6.35(dt, 1H), 6.65(d, 1H), 7.2–7.5(m, 4H) |
| A.151 | $C_2H_5$ | $-CH_2CH=CH-$ | 3-F-phenyl | 77–78 |
| A.152 | n-$C_3H_7$ | $-CH_2CH=CH-$ | 3-F-phenyl | 0.95(t, 3H)4.65(d, 2H), 6.3(dt, 1H), 6.6(d, 1H), |

TABLE 2-continued (R$^b$, R$^d$, R$^e$ = H)
(R$^c$ = Tetrahydrothiopyran-3-yl)

| Example | R$^a$ | W | R$^f$ | Phys. data (NMR data in ppm) Mp. in °C. |
|---|---|---|---|---|
| | | | | 6.9–7.3(m, 4H) |

TABLE 3

(R$^b$, R$^d$, R$^e$ = H)
(R$^c$ = Tetrahydropyran-3-yl)

| Example | R$^a$ | W | R$^f$ | Phys. data (NMR data in ppm) Mp. in °C. |
|---|---|---|---|---|
| A.153 | C$_2$H$_5$ | —CH$_2$—CH=CH— | Phenyl | |
| A.154 | n-C$_3$H$_7$ | —CH$_2$—CH=CH— | Phenyl | 4.7(d, 2H), 6.3(dt, 1H), 6.7(d, 1H), 7.2–7.5 (2m, 5H) |
| A.155 | C$_2$H$_5$ | —CH$_2$—CH=CH— | 4-Cl-phenyl | 106–108 |
| A.156 | n-C$_3$H$_7$ | —CH$_2$—CH=CH— | 4-Cl-phenyl | 4.7(d, 2H), 6.3(dt, 1H), 6.65(d, 1H), 7.2–7.5 (m, 4H) |
| A.157 | C$_2$H$_5$ | —CH$_2$—CH=CH— | 4-F-phenyl | |
| A.158 | n-C$_3$H$_7$ | —CH$_2$—CH=CH— | 4-F-phenyl | 4.65(d, 2H), 6.2(dt, 1H), 6.7(d, 1H), 7.0(m, 2H), 7.4(m, 2H) |
| A.159 | C$_2$H$_5$ | —CH$_2$—CH=CH— | 2,4-Cl$_2$-phenyl | 135–137 |
| A.160 | n-C$_3$H$_7$ | —CH$_2$—CH=CH— | 2,4-Cl$_2$-phenyl | 4.75(d, 2H), 6.3(dt, 1H), 7.0(d, 1H), 7.05–7.5 (2m, 3H) |
| A.161 | C$_2$H$_5$ | —(CH$_2$)$_3$CH=CH— | Phenyl | 4.1(t, 2H), 6.2(dt, 1H), 6.4(d, 1H), 7.2–7.4 (m, 5H) |
| A.162 | n-C$_3$H$_7$ | —(CH$_2$)$_3$CH=CH— | Phenyl | 4.1(t, 2H), 6.2(dt, 1H), 6.4(d, 1H), 7.1–7.4 (m, 5H) |
| A.163 | C$_2$H$_5$ | —(CH$_2$)$_3$CH=CH— | 4-Cl-phenyl | 92–95 |
| A.164 | n-C$_3$H$_7$ | —(CH$_2$)$_3$CH=CH— | 4-Cl-phenyl | 4.1(t, 2H), 6.2(dt, 1H), 6.35(d, 1H), 7.3(s, 4H) |
| A.165 | C$_2$H$_5$ | —(CH$_2$)$_3$— | Phenyl | 4.05(t, 2H), 7.1–7.4(m, 5H) |
| A.166 | n-C$_3$H$_7$ | —(CH$_2$)$_3$— | Phenyl | 4.05(t, 2H), 7.1–7.4(m, 5H) |
| A.167 | C$_2$H$_5$ | —CH$_2$C(=CH$_2$)—CH$_2$— | Phenyl | 3.35(s, 2H), 4.4(s, 2H), 5.0 and 5.2(2s, 2H), 7.1–7.4(m, 5H) |
| A.168 | n-C$_3$H$_7$ | —CH$_2$C(=CH$_2$)—CH$_2$— | Phenyl | 3.35(s, 2H), 4.4(s, 2H), 5.0 and 5.2(2s, 2H), 7.1–7.4(m, 5H) |
| A.169 | C$_2$H$_5$ | —CH$_2$CH=CH— | 4-Br-phenyl | 114–116° C. |
| A.170 | n-C$_3$H$_7$ | —CH$_2$CH=CH— | 4-Br-phenyl | 99–100° C. |
| A.171 | C$_2$H$_5$ | —CH$_2$CH=CH— | 4-CH$_3$-phenyl | 123–125 |
| A.172 | n-C$_3$H$_7$ | —CH$_2$CH=CH— | 4-CH$_3$-phenyl | 70–72 |
| A.173 | C$_2$H$_5$ | —CH$_2$CH=CH— | 4-CF$_3$-phenyl | 104–106 |
| A.174 | n-C$_3$H$_7$ | —CH$_2$CH=CH— | 4-CF$_3$-phenyl | 4.75(d, 2H), 6.4(dt, 1H), 6.75(d, 1H), 7.4–7.8 (m, 4H) |
| A.175 | C$_2$H$_5$ | —CH$_2$CH=CH— | 4-C$_6$H$_5$O-phenyl | 89–91 |
| A.176 | n-C$_3$H$_7$ | —CH$_2$CH=CH— | 4-C$_6$H$_5$O-phenyl | 4.65(d, 2H), 6.25(dt, 1H), 6.65(d, 1H), 6.9–7.5 (3m, 9H) |
| A.177 | C$_2$H$_5$ | —CH$_2$CH=C(CH$_3$)— | Phenyl | 2.15(s, 3H), 4.75(d, 2H), 5.95(t, 1H), 7.2–7.6 (m, 5H) |
| A.178 | n-C$_3$H$_7$ | —CH$_2$CHC(CH$_3$)— | Phenyl | 2.15(s, 3H), 4.75(d, 2H), 5.95(t, 1H), 7.2–7.6 (m, 5H) |
| A.179 | C$_2$H$_5$ | —CH$_2$CH=CH— | 2-Cl-phenyl | 113–118 |
| A.180 | n-C$_3$H$_7$ | —CH$_2$CH=CH— | 2-Cl-phenyl | 4.75(d, 2H), 6.3(dt, 1H), 7.05(d, 1H), 7.05–7.6 (m, 4H) |
| A.181 | C$_2$H$_5$ | —(CH$_2$)$_3$— | 4-F-phenyl | 4.1(t, 2H), 6.9–7.2(2m, 4H) |
| A.182 | n-C$_3$H$_7$ | —(CH$_2$)$_3$— | 4-F-phenyl | 4.1(t, 2H), 6.8–7.15(2m, 4H) |
| A.183 | C$_2$H$_5$ | —(CH$_2$)$_3$— | 2,4-Cl$_2$-phenyl | 75–77 |
| A.184 | n-C$_3$H$_7$ | —(CH$_2$)$_3$— | 2,4-Cl$_2$-phenyl | 4.05(t, 2H), 7.05–7.5(2m, 3H) |

TABLE 3-continued $R^c$, $R^d$, $R^e$ = H
($R^c$ = Tetrahydropyran-3-yl)

| Example | $R^a$ | W | $R^f$ | Phys. data (NMR data in ppm) Mp. in °C. |
|---|---|---|---|---|
| A.185 | $C_2H_5$ | $-(CH_2)_3-$ | 2-Cl-phenyl | 4.1(t, 2H), 7.0–7.4(m, 4H) |
| A.186 | n-$C_3H_7$ | $-(CH_2)_3-$ | 2-Cl-phenyl | 4.1(t, 2H), 7.0–7.4(m, 4H) |
| A.187 | $C_2H_5$ | $-(CH_2)_3-$ | 4-Cl-phenyl | 62–64 |
| A.188 | n-$C_3H_7$ | $-(CH_2)_3-$ | 4-Cl-phenyl | 4.05(t, 2H), 7.05–7.3(2m, 4H) |
| A.189 | $C_2H_5$ | $-CH_2CH=CH_2-$ | 3,5-$Cl_2$-phenyl | 126–127 |
| A.190 | n-$C_3H_7$ | $-CH_2CH=CH_2-$ | 3,5-$Cl_2$-phenyl | 4.7(d, 2H), 6.3(dt, 1H), 6.55(d, 1H), 7.1(m, 3H) |
| A.191 | $C_2H_5$ | $-(CH_2)_3-$ | 3,5-$Cl_2$-phenyl | 79–80 |
| A.192 | n-$C_3H_7$ | $-(CH_2)_3-$ | 3,5-$Cl_2$-phenyl | 4.05(t, 2H), 7.0–7.25(m, 3H) |
| A.193 | $C_2H_5$ | $-CH_2CH_2C(=CH_2)-$ | Phenyl | 4.15(t, 2H), 5.15(s, 1H), 5.3(s, 1H), 7.2–7.5 (m, 5H) |
| A.194 | n-$C_3H_7$ | $-CH_2CH_2C(=CH_2)-$ | Phenyl | 4.15(t, 2H), 5.15(s, 1H), 5.3(s, 1H), 7.2–7.5 (m, 5H) |
| A.195 | $CH_3$ | $-CH_2CH=CH_2-$ | 4-Br-phenyl | 135–137 |
| A.196 | $C_2H_5$ | $-(CH_2)_5-$ | 4-Cl-phenyl | 66–67 |
| A.197 | n-$C_3H_7$ | $-(CH_2)_5-$ | 4-Cl-phenyl | 60–62 |
| A.198 | $C_2H_5$ | $-CH_2C(CH_3)-CH_2-$ | Phenyl | 0.95(d, 3H), 3.9(m, 2H), 7.0–7.4(m, 5H) |
| A.199 | n-$C_3H_7$ | $-CH_2C(CH_3)-CH_2-$ | Phenyl | 0.95(d, 3H), 3.9(m, 2H), 7.0–7.4(m, 5H) |
| A.200 | $C_2H_5$ | $-CH_2CH=CH_2-$ | 3,4-$Cl_2$-phenyl | 4.65(d, 2H), 6.3(dt, 1H), 6.55(d, 1H), 7.2–7.6 (m, 3H) |
| A.201 | n-$C_3H_7$ | $-CH_2CH=CH_2-$ | 3,4-$Cl_2$-phenyl | 4.65(d, 2H), 6.3(dt, 1H), 6.55(d, 1H), 7.2–7.6 (m, 3H) |
| A.202 | $C_2H_5$ | $-CH_2C(CH_3)-CH_2-$ | 4-F-phenyl | 0.95(d, 3H), 3.9(dd, 2H), 6.8–7.2(m, 4H) |
| A.203 | n-$C_3H_7$ | $-CH_2C(CH_3)-CH_2-$ | 4-F-phenyl | 0.95(d, 3H), 3.9(dd, 2H), 6.8–7.2(m, 4H) |
| A.204 | $C_2H_5$ | $-CH_2C(CH_3)-CH_2-$ | 4-Cl-phenyl | 0.95(d, 3H), 3.9(mwithdd, 4H), 7.0–7.4(2m, 4H) |
| A.205 | n-$C_3H_7$ | $-CH_2C(CH_3)-CH_2-$ | 4-Cl-phenyl | 0.95(d, 3H), 3.9(mwithdd, 4H), 7.0–7.4(2m, 4H) |
| A.206 | $C_2H_5$ | $-CH_2CH_2C(CH_3)_2-$ | 4-F-phenyl | 1.3(s, 6H), 3.85(mwitht, 4H), 6.9 and 7.3 (2m, 4H) |
| A.207 | n-$C_3H_7$ | $-CH_2CH_2C(CH_3)_2-$ | 4-F-phenyl | 1.3(s, 6H), 3.85(mwitht, 4H), 6.9 and 7.3 (2m, 4H) |
| A.208 | $C_2H_5$ | $-CH_2CH_2C(CH_3)_2-$ | 4-Cl-phenyl | 1.35(s, 6H), 3.9(mwitht, 4H), 7.25(s, 4H) |
| A.209 | n-$C_3H_7$ | $-CH_2CH_2C(CH_3)_2-$ | 4-Cl-phenyl | 1.35(s, 6H), 3.9(mwitht, 4H), 7.25(s, 4H) |
| A.210 | $C_2H_5$ | $-(CH_2)_5-$ | 4-F-phenyl | 1.1(t, 3H), 4.05(t, 2H), 6.95 and 7.1(2m, 4H) |
| A.211 | n-$C_3H_7$ | $-(CH_2)_5-$ | 4-F-phenyl | 0.95(t, 3H), 4.05(t, 2H), 6.95 and 7.1(2m, 4H) |
| A.212 | $C_2H_5$ | $-CH_2CH=CH-$ | 3-Br-phenyl | 1.1(t, 3H), 4.65(d, 2H), 6.35(dt, 1H), 6.6(d, 1H), 7.2–7.6(m, 4H) |
| A.213 | n-$C_3H_7$ | $-CH_2CH=CH-$ | 3-Br-phenyl | 1.0(t, 3H), 4.65(d, 2H), 6.35(dt, 1H), 6.6(d, 1H), 7.1–7.5(m, 4H) |
| A.214 | $C_2H_5$ | $-CH_2CH=CH-$ | 3-Cl-phenyl | 1.1(t, 3H), 4.7(d, 2H), 6.35(dt, 1H), 6.6(d, 1H), 7.2–7.5(m, 4H) |
| A.215 | n-$C_3H_7$ | $-CH_2CH=CH-$ | 3-Cl-phenyl | 1.0(t, 3H), 4.7(d, 2H), 6.3(dt, 1H), 6.6(d, 1H), 7.2–7.5(m, 4H) |
| A.216 | $C_2H_5$ | $-CH_2CH=CH-$ | 3-F-phenyl | 66–68 |
| A.217 | n-$C_3H_7$ | $-CH_2CH=CH-$ | 3-F-phenyl | 1.0(t, 3H), 4.7(d, 2H), 6.3(dt, 1H), 6.6(d, 1H), 6.8–7.4(m, 4H) |

TABLE 4

$R^b$, $R^d$, $R^e$ = H
($R^c$ = Tetrahydropyran-4-yl)

| Example | $R^a$ | W | $R^f$ | Phys. data (NMR data in ppm) Mp. in °C. |
|---|---|---|---|---|
| A.218 | $C_2H_5$ | $-CH_2-CH=CH-$ | Phenyl | 129–130 |
| A.219 | n-$C_3H_7$ | $-CH_2-CH=CH-$ | Phenyl | 85–87 |
| A.220 | $C_2H_5$ | $-CH_2-CH=CH-$ | 4-Cl-phenyl | 130–131 |
| A.221 | n-$C_3H_7$ | $-CH_2-CH=CH-$ | 4-Cl-phenyl | 108–110 |
| A.222 | $C_2H_5$ | $-CH_2-CH=CH-$ | 4-F-phenyl | 118–120 |
| A.223 | n-$C_3H_7$ | $-CH_2-CH=CH-$ | 4-F-phenyl | 87–89 |
| A.224 | $C_2H_5$ | $-CH_2-CH=CH-$ | 2,4-$Cl_2$-phenyl | 95–97 |

TABLE 4-continued $$\text{structure with } R^c, OH, NO-W-R^4, R^a, O$$

($R^b$, $R^d$, $R^e$ = H)
($R^c$ = Tetrahydropyran-4-yl)

| Example | $R^a$ | W | $R^f$ | Phys. data (NMR data in ppm) Mp. in °C. |
|---|---|---|---|---|
| A.225 | n-$C_3H_7$ | $-CH_2-CH=CH-$ | 2,4-$Cl_2$-phenyl | 93–95 |
| A.226 | $C_2H_5$ | $-(CH_2)_3CH=CH-$ | Phenyl | 77–78 |
| A.227 | n-$C_3H_7$ | $-(CH_2)_3CH=CH-$ | Phenyl | 67–68 |
| A.228 | $C_2H_5$ | $-(CH_2)_3CH=CH-$ | 4-Cl-phenyl | 99–100 |
| A.229 | n-$C_3H_7$ | $-(CH_2)_3CH=CH-$ | 4-Cl-phenyl | 4.05(t, 2H), 6.2(dt, 1H), 6.4(d, 1H), 7.3(s, 4H) |
| A.230 | $C_2H_5$ | $-(CH_2)_3-$ | Phenyl | 4.1(t, 2H), 7.0–7.4(m, 5H) |
| A.231 | n-$C_3H_7$ | $-(CH_2)_3-$ | Phenyl | 4.1(t, 2H), 7.0–7.4(m, 5H) |
| A.232 | $C_2H_5$ | $-CH_2C(=CH_2)-CH_2-$ | Phenyl | 3.4(s, 2H), 4.4(s, 2H), 5.0 and 5.2(2s, 2H), 7.1–7.4(m, 5H) |
| A.233 | n-$C_3H_7$ | $-CH_2C(=CH_2)-CH_2-$ | Phenyl | 3.35(s, 2H), 4.4(s, 2H), 5.0 and 5.1(2s, 2H), 7.1–7.4(m, 5H) |
| A.234 | $C_2H_5$ | $-CH_2CH=CH$ | 4-Br-phenyl | 140–142 |
| A.235 | n-$C_3H_7$ | $-CH_2CH=CH$ | 4-Br-phenyl | 117–119 |
| A.236 | $C_2H_5$ | $-CH_2CH=CH$ | 4-$CH_3$-phenyl | 135–137 |
| A.237 | n-$C_3H_7$ | $-CH_2CH=CH$ | 4-$CH_3$-phenyl | 97–98 |
| A.238 | $C_2H_5$ | $-CH_2CH=CH$ | 4-$CF_3$-phenyl | 103–104 |
| A.239 | n-$C_3H_7$ | $-CH_2CH=CH$ | 4-$CF_3$-phenyl | 114–116 |
| A.240 | $C_2H_5$ | $-CH_2CH=CH$ | 4-$C_6H_5O$-phenyl | 64–66 |
| A.241 | n-$C_3H_7$ | $-CH_2CH=CH$ | 4-$C_6H_5O$-phenyl | 4.65(d, 2H), 6.2(dt, 1H), 6.65(d, 1H), 6.9–7.5(3m, 9H) |
| A.242 | $C_2H_5$ | $-CH_2CH=C(CH_3)-$ | Phenyl | 70–72 |
| A.243 | n-$C_3H_7$ | $-CH_2CH=C(CH_3)-$ | Phenyl | 2.15(s, 3H), 4.75(d, 2H), 5.95(t, 1H), 7.2–7.6(m, 5H) |
| A.244 | $C_2H_5$ | $-CH_2CH=CH-$ | 2-Cl-phenyl | 85–87 |
| A.245 | n-$C_3H_7$ | $-CH_2CH=CH-$ | 2-Cl-phenyl | 90–92 |
| A.246 | $C_2H_5$ | $-(CH_2)_3-$ | 4-F-phenyl | 65–67 |
| A.247 | n-$C_3H_7$ | $-(CH_2)_3-$ | 4-F-phenyl | 64–66 |
| A.248 | $C_2H_5$ | $-(CH_2)_3-$ | 2,4-$Cl_2$-phenyl | 4.05(t, 2H), 7.05–7.4(2m, 3H) |
| A.249 | n-$C_3H_7$ | $-(CH_2)_3-$ | 2,4-$Cl_2$-phenyl | 65–67 |
| A.250 | $C_2H_5$ | $-(CH_2)_3-$ | 4-Br-phenyl | 111–112 |
| A.251 | $C_2H_5$ | $-(CH_2)_3-$ | 2-Cl-phenyl | 4.1(t, 2H), 7.0–7.4(m, 4H) |
| A.252 | n-$C_3H_7$ | $-(CH_2)_3-$ | 2-Cl-phenyl | 4.1(t, 2H), 7.05–7.45(m, 4H) |
| A.253 | $C_2H_5$ | $-(CH_2)_3-$ | 4-Cl-phenyl | 97–99 |
| A.254 | n-$C_3H_7$ | $-(CH_2)_3-$ | 4-Cl-phenyl | 84–86 |
| A.255 | $C_2H_5$ | $-CH_2CH=CH-$ | 3,5-$Cl_2$-phenyl | 127–128 |
| A.256 | n-$C_3H_7$ | $-CH_2CH=CH-$ | 3,5-$Cl_2$-phenyl | 80–81 |
| A.257 | $C_2H_5$ | $-CH_2CH_2CH(CH_3)-$ | Phenyl | 1.25(d, 3H), 4.0(m, 2H), 7.05–7.4(m, 5H) |
| A.258 | n-$C_3H_7$ | $-CH_2CH_2CH(CH_3)-$ | Phenyl | 1.25(d, 3H), 4.0(m, 2H), 7.0–7.4(m, 5H) |
| A.259 | $C_2H_5$ | $-(CH_2)_3-$ | 3,5-$Cl_2$-phenyl | 105–107 |
| A.260 | n-$C_3H_7$ | $-(CH_2)_3-$ | 3,5-$Cl_2$-phenyl | 73–75 |
| A.261 | $C_2H_5$ | $-CH_2CH_2C(=CH_2)-$ | Phenyl | 4.15(t, 2H), 5.15(s, 1H), 5.3(s, 1H), 7.2–7.6(m, 5H) |
| A.262 | n-$C_3H_7$ | $-CH_2CH_2C(=CH_2)-$ | Phenyl | 4.15(t, 2H), 5.15(s, 1H), 5.3(s, 1H), 7.2–7.6(m, 5H) |
| A.263 | $C_2H_5$ | $-(CH_2)_5-$ | 4-Cl-phenyl | 66–67 |
| A.264 | n-$C_3H_7$ | $-(CH_2)_5-$ | 4-Cl-phenyl | 61–63 |
| A.265 | $C_2H_5$ | $-CH_2C(CH_3)-CH_2-$ | Phenyl | 0.9(d, 3H), 3.9(m, 2H), 7.0–7.4(m, 5H) |
| A.266 | n-$C_3H_7$ | $-CH_2C(CH_3)-CH_2-$ | Phenyl | 0.9(d, 3H), 3.9(m, 2H), 7.0–7.4(m, 5H) |
| A.267 | $C_2H_5$ | $-CH_2CH=CH-$ | 3,4-$Cl_2$-phenyl | 103–105 |
| A.268 | n-$C_3H_7$ | $-CH_2CH=CH-$ | 3,4-$Cl_2$-phenyl | 4.65(d, 2H), 6.3(dt, 1H), 6.55(d, 1H), 7.2–7.6(m, 3H) |
| A.269 | $C_2H_5$ | $-(CH_2)_3-$ | 3,4-$Cl_2$-phenyl | 3.95–4.1(m, 4H), 7.0–7.1 and 7.2–7.45(2m, 3H) |
| A.270 | $C_2H_5$ | $-CH_2C(CH_3)-CH_2-$ | 4-F-phenyl | 0.90(d, 3H), 3.85(dd, 2H), 6.8–7.2(m, 4H) |
| A.271 | n-$C_3H_7$ | $-CH_2C(CH_3)-CH_2-$ | 4-F-phenyl | 0.90(d, 3H), 3.85(dd, 2H), 6.8–7 (m, 4H) |
| A.272 | $C_2H_5$ | $-CH_2C(CH_3)-CH_2-$ | 4-Cl-phenyl | 0.90(d, 3H), 3.85(dd, 2H), 7.0–7.4(2m, 4H) |
| A.273 | n-$C_3H_7$ | $-CH_2C(CH_3)-CH_2-$ | 4-Cl-phenyl | 0.90(d, 3H), 3.85(dd, 2H), 7.0–7.4(2m, 4H) |
| A.274 | $C_2H_5$ | $-CH_2CH_2C(CH_3)_2-$ | 4-F-phenyl | 1.35(s, 6H), 3.85(t, 2H), 7.0 and 7.3(2m, 4H) |
| A.275 | n-$C_3H_7$ | $-CH_2CH_2C(CH_3)_2-$ | 4-F-phenyl | 1.35(s, 6H), 3.85(t, 2H), 7.0 and 7.3(2m, 4H) |
| A.276 | $C_2H_5$ | $-CH_2CH_2C(CH_3)_2-$ | 4-Cl-phenyl | 1.35(s, 6H), 3.85(t, 2H), 7.25(s, 4H) |
| A.277 | n-$C_3H_7$ | $-CH_2CH_2C(CH_3)_2-$ | 4-Cl-phenyl | 1.35(s, 6H), 3.85(t, 2H), 7.25(s, 4H) |
| A.278 | $C_2H_5$ | $-(CH_2)_6-$ | 4-Cl-phenyl | 1.15(t, 3H), 3.35(t, 2H), 7.1(d, 2H), 7.25(d, 2H) |
| A.279 | n-$C_3H_7$ | $-(CH_2)_6-$ | 4-Cl-phenyl | 0.95(t, 3H), 3.35(t, 2H), 7.1(d, 2H), 7.25(d, 2H) |
| A.280 | $C_2H_5$ | $-(CH_2)_6-$ | 4-F-phenyl | 1.1(t, 3H), 3.35(t, 2H) |
| A.281 | n-$C_3H_7$ | $-(CH_2)_6-$ | 4-F-phenyl | 0.95(t, 3H), 3.35(t, 2H) |
| A.282 | $C_2H_5$ | $-(CH_2)_5-$ | 4-F-phenyl | 1.15(t, 3H), 3.35(t, 2H), 6.95 and 7,1(2m, 4H) |
| A.283 | n-$C_3H_7$ | $-(CH_2)_5-$ | 4-F-phenyl | 0.95(t, 3H), 3.35(t, 2H), 6.95 and 7.1(2m, 4H) |
| A.284 | $C_2H_5$ | $-CH_2CH(CH_3)-CH_2CH_2CH_2-$ | 2-$CH_3$-phenyl | 2.3(s, 3H), 7.05(m, 4H) |
| A.285 | n-$C_3H_7$ | $-CH_2CH(CH_3)-CH_2CH_2CH_2-$ | 2-$CH_3$-phenyl | 2.3(s, 3H), 7.1(m, 4H) |

TABLE 4-continued $(R^b, R^d, R^e = H)$
$(R^c = \text{Tetrahydropyran-4-yl})$

| Example | $R^a$ | W | $R^f$ | Phys. data (NMR data in ppm) Mp. in °C. |
|---|---|---|---|---|
| A.286 | n-C$_3$H$_7$ | —CH$_2$CH=CH— | 3-F-phenyl | 61–62 |
| A.287 | C$_2$H$_5$ | —CH$_2$CH=CH— | 3-Br-phenyl | 103–105 |
| A.288 | n-C$_3$H$_7$ | —CH$_2$CH=CH— | 3-Br-phenyl | 80–82 |
| A.289 | C$_2$H$_5$ | —CH$_2$CH=CH— | 3-Cl-phenyl | 109–111 |
| A.290 | n-C$_3$H$_7$ | —CH$_2$CH=CH— | 3-Cl-phenyl | 89–91 |
| A.291 | C$_2$H$_5$ | —CH$_2$CH=CH— | 3-F-phenyl | 122–123 |

TABLE 5

$(R^b, R^d, R^e = H)$

| Example | $R^c$ | $R^a$ | W | $R^f$ | Phys. data (NMR data in ppm) Mp. in °C. |
|---|---|---|---|---|---|
| A.292 | 2-Ethylthiopropyl | n-C$_3$H$_7$ | —(CH$_2$)$_3$— | Phenyl | 4.05(t, 2H), 7.15–7.4(m, 5H) |
| A.293 | 2,4,6-Trimethylphenyl | C$_2$H$_5$ | —CH$_2$CH=CH— | 2,4-Cl$_2$-phenyl | 106–107 |
| A.294 | 2,4,6-Trimethylphenyl | C$_2$H$_5$ | —CH$_2$CH=CH— | 4-F-phenyl | 2.2(s, 3H), 2.35(s, 6H), 4.7(d, 2H), 6.3(dt, 1H), 6.65(d, 1H), 7.0(m, 2H), 7.4(m, 2H) |
| A.295 | Phenyl | n-C$_3$H$_7$ | —CH$_2$CH=CH— | 4-F-phenyl | 55–57 |
| A.296 | 4-(Benzoylamino)phenyl | n-C$_3$H$_7$ | —CH$_2$CH=CH— | 4-F-phenyl | 80–82 |
| A.297 | 5,6-Dihydrothiopyran-3-yl | C$_2$H$_5$ | —CH$_2$CH=CH— | 4-F-phenyl | 94–96 |
| A.298 | Cyclohexyl | n-C$_3$H$_7$ | —CH$_2$CH=CH— | 4-F-phenyl | 67–69 |
| A.299 | 3-Isopropylisoxazol-5-yl | n-C$_3$H$_7$ | —CH$_2$CH=CH— | 4-F-phenyl | 103–104 |
| A.300 | 5,6-Dihydrothiopyran-3-yl | C$_2$H$_5$ | —CH$_2$CH=CH— | 2,4-Cl$_2$-phenyl | 88–89 |
| A.301 | Cyclohex-3-enyl | n-C$_3$H$_7$ | —CH$_2$CH=CH— | 2,4-Cl$_2$-phenyl | 75–77 |
| A.302 | 3-Isopropylisoxazol-5-yl | n-C$_3$H$_7$ | —CH$_2$CH=CH— | 2,4-Cl$_2$-phenyl | 113–115 |
| A.303 | 3-Isopropylisothiazol-5-yl | C$_2$H$_5$ | —CH$_2$CH=CH— | 2,4-Cl$_2$-phenyl | 82–83 |
| A.304 | 4-Ethylphenyl | C$_2$H$_5$ | —CH$_2$CH=CH— | 2,4-Cl$_2$-phenyl | 81–82 |
| A.305 | 3-Isopropylisothiazol-5-yl | C$_2$H$_5$ | —CH$_2$CH=CH— | 4-F-phenyl | 98–101 |
| A.306 | N-Isopropylpyrrol-3-yl | n-C$_3$H$_7$ | —CH$_2$CH=CH— | 4-F-phenyl | 54–56 |
| A.307 | 3-Nitro-4-fluorphenyl | n-C$_3$H$_7$ | —CH$_2$CH=CH— | 4-Br-phenyl | 124–126 |
| A.308 | Cyclohex-3-enyl | n-C$_3$H$_7$ | —CH$_2$CH=CH— | 4-Br-phenyl | 68–71 |
| A.309 | Thien-3-yl | n-C$_3$H$_7$ | —CH$_2$CH=CH— | 4-Br-phenyl | 85–87 |
| A.310 | 4-(Prop-2-inoxy)phenyl | C$_2$H$_5$ | —CH$_2$CH=CH— | 4-Br-phenyl | 126–129 |
| A.311 | 2-Ethylthiopropyl | C$_2$H$_5$ | —CH$_2$CH=CH— | 2,4-Cl$_2$-phenyl | 4.7(d, 2H), 6.3(dt, 1H), 7.0(d, 1H), 7.2–7.6(m, 3H) |
| A.312 | 3-Isopropylisoxazol-5-yl | CH$_3$ | —CH$_2$CH=CH— | 4-Cl-phenyl | 113–115 |
| A.313 | Ethoxycarbonyl | n-C$_3$H$_7$ | —CH$_2$CH=CH— | 4-Cl-phenyl | 44–45 |
| A.314 | 4-Ethylphenyl | C$_2$H$_5$ | —CH$_2$CH=CH— | 4-Cl-phenyl | 104–106 |
| A.315 | (2,2-dimethyl-1,3-dioxan) | C$_2$H$_5$ | —CH$_2$CH=CH— | 4-Cl-phenyl | 68–70 |
| A.316 | Cyclohex-1-enyl | n-C$_3$H$_7$ | —CH$_2$CH=CH— | 4-Cl-phenyl | 63–64 |
| A.317 | 4-(Benzoylamino)phenyl | n-C$_3$H$_7$ | —CH$_2$CH=CH— | 4-Cl-phenyl | 132–134 |
| A.318 | 4-(Prop-2-inoxy)phenyl | C$_2$H$_5$ | —CH$_2$CH=CH— | 4-Cl-phenyl | 122–124 |
| A.319 | 2-Ethylthiophenyl | n-C$_3$H$_7$ | —(CH$_2$)$_6$— | 4-Cl-phenyl | 0.95(t, 3H), 4.0(t, 2H), 7.1(d, 2H), 7.25(d, 2H) |
| A.320 | 2,4,6-Trimethylphenyl | C$_2$H$_5$ | —(CH$_2$)$_6$— | 4-Cl-phenyl | 1.15(t, 3H), 2.25(s, 3H), 6.85(s, 2H) |
| A.321 | 2,4,6-Trimethylphenyl | C$_2$H$_5$ | —(CH$_2$)$_6$— | 4-F-phenyl | 1.2(t, 3H), 2.25(s, 3H), 4.05(t, 2H) |
| A.322 | 2-Ethylthiopropyl | n-C$_3$H$_7$ | —(CH$_2$)$_6$— | 4-F-phenyl | 0.95(t, 3H), 4.0(t, 2H) |

TABLE 6

$R^b, R^d, R^e = H$

| Compound no. | $R^c$ | $R^a$ | W | $R^f$ | $^1$H-NMR*) [δ ppm] | Mp. [°C.] |
|---|---|---|---|---|---|---|
| A.323 | Tetrahydrothiopyran-3-yl | n-C$_3$H$_7$ | —CH$_2$—C≡C— | Phenyl | 4.9(s, 2H); 7.2–7.6(2m, 5H) | |
| A.324 | Tetrahydrothiopyran-3-yl | n-C$_3$H$_7$ | —CH$_2$—C≡C—CH$_2$— | Phenyl | 3.6(s, 2H); 4.7(s, 2H), 7.2–7.5(m, 5H) | |
| A.325 | Tetrahydrothiopyran-3-yl | C$_2$H$_5$ | —CH$_2$—C≡C—CH$_2$— | Phenyl | 3.65(s, 2H); 4.7(s, 2H); 7.2–7.5(m, 5H) | |
| A.326 | Tetrahydropyran-3-yl | n-C$_3$H$_7$ | —CH$_2$—C≡C—CH$_2$— | Phenyl | 3.65(s, 2H); 4.7(s, 2H); 7.2–7.5(m, 5H) | |
| A.327 | 2-Ethylthiopropyl | n-C$_3$H$_7$ | —CH$_2$—C≡C— | Phenyl | 4.9(s, 2H); 7.3–7.6(m, 5H) | |
| A.328 | 2-Ethylthiopropyl | n-C$_3$H$_7$ | —CH$_2$—C≡C—CH$_2$— | Phenyl | 3.65(s, 2H); 4.7(s, 2H); 7.2–7.5(m, 5H) | |
| A.329 | Tetrahydropyran-4-yl | C$_2$H$_5$ | —CH$_2$—C≡C—CH$_2$— | Phenyl | 3.65(s, 2H); 4.7(s, 2H); 7.2–7.5(m, 5H) | |
| A.330 | Tetrahydropyran-4-yl | n-C$_3$H$_7$ | —CH$_2$—C≡C—CH$_2$— | Phenyl | 3.6(s, 2H); 4.65(s, 2H); 7.1–7.6(m, 5H) | |
| A.331 | Tetrahydropyran-4-yl | n-C$_3$H$_7$ | —(CH$_2$)$_3$—C≡C— | 4-F-phenyl | 4.25(t, 2H); 6.8–7.5(2m, 4H) | |
| A.332 | Tetrahydropyran-4-yl | C$_2$H$_5$ | —(CH$_2$)$_3$—C≡C— | 4-F-phenyl | 4.25(t, 2H); 6.8–7.5(2m, 4H) | |
| A.333 | Tetrahydrothiopyran-3-yl | C$_2$H$_5$ | —(CH$_2$)$_3$—C≡C— | 4-F-phenyl | 4.25(t, 2H); 6.8–7.5(2m, 4H) | |
| A.334 | Tetrahydrothiopyran-3-yl | n-C$_3$H$_7$ | —(CH$_2$)$_3$—C≡C— | 4-F-phenyl | 4.25(t, 2H); 6.8–7.5(2m, 4H) | |
| A.335 | Tetrahydropyran-3-yl | C$_2$H$_5$ | —(CH$_2$)$_3$—C≡C— | 4-F-phenyl | 4.25(t, 2H); 6.8–7.5(2m, 4H) | |
| A.336 | Tetrahydropyran-3-yl | n-C$_3$H$_7$ | —(CH$_2$)$_3$—C≡C— | 4-F-phenyl | 4.25(t, 2H); 6.8–7.5(2m, 4H) | |
| A.337 | Tetrahydrothiopyran-3-yl | C$_2$H$_5$ | —CH$_2$CH$_2$—C≡C— | 4-F-phenyl | 4.25(t); 6.98(dd); 7.35(dd) | 74–90 |
| A.338 | Tetrahydrothiopyran-3-yl | n-C$_3$H$_7$ | —CH$_2$CH$_2$—C≡C— | 4-F-phenyl | 4.25(t); 6.98(dd); 7.35(dd) | — |
| A.339 | Tetrahydropyran-3-yl | C$_2$H$_5$ | —CH$_2$CH$_2$—C≡C— | 4-F-phenyl | 4.25(t); 6.98(dd); 7.35(dd) | 55–61 |
| A.340 | Tetrahydropyran-3-yl | n-C$_3$H$_7$ | —CH$_2$CH$_2$—C≡C— | 4-F-phenyl | 4.25(t); 6.98(dd); 7.35(dd) | — |
| A.341 | Tetrahydropyran-4-yl | C$_2$H$_5$ | —CH$_2$CH$_2$—C≡C— | 4-F-phenyl | 4.25(t); 6.98(dd); 7.35(dd) | 83–87 |
| A.342 | Tetrahydropyran-4-yl | n-C$_3$H$_7$ | —CH$_2$CH$_2$—C≡C— | 4-F-phenyl | 4.25(t); 6.98(dd); 7.35(dd) | 98–102 |
| A.343 | 3-Isopropylisoxazol-5-yl | n-C$_3$H$_7$ | —CH$_2$CH$_2$—C≡C— | 4-F-phenyl | 4.25(t); 5.94(s); 7.0(dd); 7.37(dd) | — |
| A.344 | 4-Methylphenyl | n-C$_3$H$_7$ | —CH$_2$CH$_2$—C≡C— | 4-F-phenyl | 4.25(t); 6.98(dd); 7.15(m); 7.35(dd) | 65–69 |
| A.345 | 3,4-Dibromtetrahydro-pyran-3-yl | n-C$_3$H$_7$ | —CH$_2$CH$_2$—C≡C— | 4-F-phenyl | 4.25(t); 6.98(dd); 7.35(dd) | — |
| A.346 | Tetrahydrothiopyran-3-yl | n-C$_3$H$_7$ | —CH$_2$CH$_2$—C≡C— | 4-Cl-phenyl | 4.25(t); 7.25(d); 7.35(d) | — |
| A.347 | Tetrahydrothiopyran-3-yl | C$_2$H$_5$ | —CH$_2$CH$_2$—C≡C— | 4-Cl-phenyl | 4.25(t); 7.25(d); 7.35(d) | 82–86 |
| A.348 | Tetrahydropyran-3-yl | C$_2$H$_5$ | —CH$_2$CH$_2$—C≡C— | 4-Cl-phenyl | 4.25(t); 7.25(d); 7.35(d) | 99–101 |
| A.349 | Tetrahydropyran-3-yl | n-C$_3$H$_7$ | —CH$_2$CH$_2$—C≡C— | 4-Cl-phenyl | 4.25(t); 7.25(d); 7.35(d) | |
| A.350 | Tetrahydropyran-4-yl | C$_2$H$_5$ | —CH$_2$CH$_2$—C≡C— | 4-Cl-phenyl | 4.25(t); 7.25(d); 7.35(d) | 98–101 |
| A.351 | Tetrahydropyran-4-yl | n-C$_3$H$_7$ | —CH$_2$CH$_2$—C≡C— | 4-Cl-phenyl | 4.25(t); 7.25(d); 7.35(d) | 115–118 |
| A.352 | 3-Isopropylisoxazol-5-yl | n-C$_3$H$_7$ | —CH$_2$CH$_2$—C≡C— | 4-Cl-phenyl | 4.25(t); 5.9(s); 7.25(d); 7.35(d) | 71–74 |

TABLE 6-continued $$\text{structure with } R^c, OH, NO-W-R^4, R^a, O \quad (R^b, R^d, R^e = H)$$

| Compound no. | $R^c$ | $R^a$ | W | $R^f$ | $^1$H-NMR*) [δ ppm] | Mp. [°C.] |
|---|---|---|---|---|---|---|
| A.353 | 4-Methylphenyl | n-C$_3$H$_7$ | —CH$_2$CH$_2$—C≡C— | 4-Cl-phenyl | 4.25(t); 7.45(m); 7.28(M) | 93–6 |
| A.354 | 3,4-Dibromtetrahydropyran-3-yl | n-C$_3$H$_7$ | —CH$_2$CH$_2$—C≡C— | 4-Cl-phenyl | 4.25(t); 7.25(d); 7.25(d); | — |
| A.355 | Tetrahydrothiopyran-3-yl | C$_2$H$_5$ | —(CH$_2$)$_3$—C≡C— | 4-Cl-phenyl | 1.15(t); 4.2(t); 7.25(d); 7.35(d) | |
| A.356 | Tetrahydrothiopyran-3-yl | n-C$_3$H$_7$ | —(CH$_2$)$_3$—C≡C— | 4-Cl-phenyl | 0.98(t); 4.2(t); 7.25(d); 7.35(d) | |
| A.357 | Tetrahydropyran-3-yl | C$_2$H$_5$ | —(CH$_2$)$_3$—C≡C— | 4-Cl-phenyl | 1.15(t); 4.2(t); 7.25(d); 7.35(d) | |
| A.358 | Tetrahydropyran-3-yl | n-C$_3$H$_7$ | —(CH$_2$)$_3$—C≡C— | 4-Cl-phenyl | 0.95(t); 4.2(t); 7.25(d); 7.35(d) | |
| A.359 | Tetrahydropyran-4-yl | C$_2$H$_5$ | —(CH$_2$)$_3$—C≡C— | 4-Cl-phenyl | 1.15(t); 4.2(t); 7.25(d); 7.35(d) | |
| A.360 | Tetrahydropyran-4-yl | n-C$_3$H$_7$ | —(CH$_2$)$_3$—C≡C— | 4-Cl-phenyl | 0.98(t); 4.2(t); 7.25(d); 7.35(d) | |
| A.361 | Tetrahydrothiopyran-3-yl | C$_2$H$_5$ | —CH$_2$—CH$_2$—C≡C— | 2-Thienyl | 1.15(t); 2.75(t); 4.25(t); 7.05(m); 7.2(m) | |
| A.362 | Tetrahydrothiopyran-3-yl | n-C$_3$H$_7$ | —CH$_2$—CH$_2$—C≡C— | 2-Thienyl | 0.95(t); 2.75(t); 4.25(t); 7.05(m); 7.2(m) | |
| A.363 | Tetrahydropyran-3-yl | C$_2$H$_5$ | —CH$_2$—CH$_2$—C≡C— | 2-Thienyl | 1.15(t); 2.75(t); 4.25(t); 7.05(m); 7.2(m) | |
| A.364 | Tetrahydropyran-3-yl | n-C$_3$H$_7$ | —CH$_2$—CH$_2$—C≡C— | 2-Thienyl | 0.95(t); 2.75(t); 4.25(t); 7.05(m); 7.2(m) | |
| A.365 | Tetrahydropyran-4-yl | C$_2$H$_5$ | —CH$_2$—CH$_2$—C≡C— | 2-Thienyl | 1.15(t); 2.75(t); 4.25(t); 7.05(m); 7.2(m) | |
| A.366 | Tetrahydropyran-4-yl | n-C$_3$H$_7$ | —CH$_2$—CH$_2$—C≡C— | 2-Thienyl | 0.95(t); 2.75(t); 4.25(t); 7.05(m); 7.2(m) | |
| 3.45 | Tetrahydrothiopyran-3-yl | C$_2$H$_5$ | —CH$_2$CH=C(CH$_3$)—C≡C—**) | 4-Cl-phenyl | 1.15(t); 2.0(s); 4.8(d); 5.9(t) | |
| 3.46 | Tetrahydrothiopyran-3-yl | n-C$_3$H$_7$ | —CH$_2$CH=C(CH$_3$)—C≡C—**) | 4-Cl-phenyl | 0.95(t); 2.0(s); 4.8(d); 5.9(t) | |
| 3.47 | Tetrahydropyran-4-yl | C$_2$H$_5$ | —CH$_2$CH=C(CH$_3$)—C≡C—**) | 4-Cl-phenyl | 1.15(t); 2.0(s); 4.8(d); 5.9(t) | |
| 3.48 | Tetrahydropyran-4-yl | n-C$_3$H$_7$ | —CH$_2$CH=C(CH$_3$)—C≡C—**) | 4-Cl-phenyl | 0.95(t); 2.0(s); 4.8(d); 5.9(t) | |
| 3.49 | 2-Ethylthiopropyl | n-C$_3$H$_7$ | —CH$_2$CH=C(CH$_3$)—C≡C—**) | 4-Cl-phenyl | 0.95(t); 2.0(s); 4.8(d); 5.9(t) | |
| 3.50 | 2,4,6-Trimethylphenyl | C$_2$H$_5$ | —CH$_2$CH=C(CH$_3$)—C≡C—**) | 4-Cl-phenyl | 1.2(t); 2.0(s); 4.8(d); 5.95(t) | |
| 3.51 | Tetrahydrothiopropan-3-yl | C$_2$H$_5$ | —CH$_2$CH=C(CH$_3$)—C≡C—**) | 4-F-phenyl | 1.1(t); 2.0(s); 4.8(d); 5.9(t) | |
| 3.52 | Tetrahydrothiopropan-3-yl | n-C$_3$H$_7$ | —CH$_2$CH=C(CH$_3$)—C≡C—**) | 4-F-phenyl | 0.95(t); 2.0(s); 4.8(d); 5.9(t) | |
| A.375 | Tetrahydropyran-4-yl | n-C$_3$H$_7$ | —CH$_2$—CH=C(CH$_3$)—C≡C—**) | 4-F-phenyl | 0.95(t); 2.0(s); 4.8(d); 5.9(t) | |
| A.376 | Tetrahydropyran-4-yl | C$_2$H$_5$ | —CH$_2$—CH=C(CH$_3$)—C≡C—**) | 4-F-phenyl | 1.15(t); 2.0(s); 4.8(d); | |

TABLE 6-continued $$\text{(structure shown with } R^c, R^a, \text{NO-W-}R^4, \text{OH, =O substituents)} \quad (R^b, R^d, R^e = H)$$

| Compound no. | $R^c$ | $R^a$ | W | $R^f$ | $^1$H-NMR*) [δ ppm] | Mp. [°C.] |
|---|---|---|---|---|---|---|
| A.377 | 2-Ethylthiopropyl | n-$C_3H_7$ | $-CH_2-CH=C(CH_3)-C\equiv C-$**) | 4-F-phenyl | 5.9(t) 0.95(t); 2.0(s); 4.8(d); 5.9(t) | |

*)selected signals
**)Z-configuration at the double bond

TABLE 7

$$\text{(structure shown with } R^c, R^a, \text{NO-W-}R^f, \text{OH, =O substituents)} \quad (R^b, R^d, R^e = H)$$

| No. | $R^a$ | $R^c$ | W | $R^f$ | Phys. data NMR data in ppm Mp. in °C. |
|---|---|---|---|---|---|
| A.378 | $C_2H_5$ | Tetrahydropyran-3-yl | $-(CH_2)_2-$ | Furan-2-yl | |
| A.379 | n-$C_3H_7$ | Tetrahydropyran-3-yl | $-(CH_2)_2-$ | Furan-2-yl | |
| A.380 | $C_2H_5$ | Tetrahydropyran-4-yl | $-(CH_2)_2-$ | Furan-2-yl | |
| A.381 | n-$C_3H_7$ | Tetrahydropyran-4-yl | $-(CH_2)_2-$ | Furan-2-yl | |
| A.382 | $C_2H_5$ | Tetrahydrothiopyran-3-yl | $-(CH_2)_2-$ | Furan-2-yl | |
| A.383 | n-$C_3H_7$ | Tetrahydrothiopyran-3-yl | $-(CH_2)_2-$ | Furan-2-yl | |
| A.384 | $C_2H_5$ | Tetrahydropyran-3-yl | $-(CH_2)_2-$ | Thien-2-yl | 3.92(m, 2H), 4.33(t, 2H), 6.82(m, 1H), 6.93(m, 1H), 7.13(m, 1H) |
| A.385 | n-$C_3H_7$ | Tetrahydropyran-3-yl | $-(CH_2)_2-$ | Thien-2-yl | 3.92(m, 2H), 4.33(t, 2H), 6.82(m, 1H), 6.93(m, 1H), 7.13(m, 1H) |
| A.386 | $C_2H_5$ | Tetrahydropyran-4-yl | $-(CH_2)_2-$ | Thien-2-yl | 4.00(m, 2H), 4.33(t, 2H), 6.82(m, 1H), 6.93(m, 1H), 7.13(m, 1H) |
| A.387 | n-$C_3H_7$ | Tetrahydropyran-4-yl | $-(CH_2)_2-$ | Thien-2-yl | 4.00(m, 2H), 4.33(t, 2H), 6.82(m, 1H), 6.93(m, 1H), 7.13(m, 1H) |
| A.388 | $C_2H_5$ | Tetrahydrothiopyran-3-yl | $-(CH_2)_2-$ | Thien-2-yl | 4.30(t, 2H), 6.82(m, 1H), 6.93(m, 1H), 7.13(m, 1H) |
| A.389 | n-$C_3H_7$ | Tetrahydrothiopyran-3-yl | $-(CH_2)_2-$ | Thien-2-yl | 4.30(t, 2H), 6.82(m, 1H), 6.93(m, 1H), 7.13(m, 1H) |
| A.390 | $C_2H_5$ | Tetrahydropyran-3-yl | $-(CH_2)_2-$ | Pyrid-2-yl | 3.90(m, 2H), 4.46(t, 2H), 7.20(m, 2H), 7.67(m, 1H), 8.50(m, 1H) |
| A.391 | n-$C_3H_7$ | Tetrahydropyran-3-yl | $-(CH_2)_2-$ | Pyrid-2-yl | |
| A.392 | $C_2H_5$ | Tetrahydropyran-4-yl | $-(CH_2)_2-$ | Pyrid-2-yl | 4.00(m, 2H), 4.46(t, 2H), 7.20(m, 2H), 7.67(m, 1H), 8.50(m, 1H) |
| A.393 | n-$C_3H_7$ | Tetrahydropyran-4-yl | $-(CH_2)_2-$ | Pyrid-2-yl | |
| A.394 | $C_2H_5$ | Tetrahydrothiopyran-3-yl | $-(CH_2)_2-$ | Pyrid-2-yl | 4.46(t, 2H), 7.20(m, 2H), 7.67(m, 1H), 8.50(m, 1H) |
| A.395 | n-$C_3H_7$ | Tetrahydrothiopyran-3-yl | $-(CH_2)_2-$ | Pyrid-2-yl | |
| A.396 | $C_2H_5$ | Tetrahydropyran-3-yl | $-(CH_2)_3-$ | Furan-2-yl | 3.93(m, 2H), 4.10(t, 2H), 6.00(m, 1H), 6.26(m, 1H), 7.33(m, 1H) |
| A.397 | n-$C_3H_7$ | Tetrahydropyran-3-yl | $-(CH_2)_3-$ | Furan-2-yl | 3.93(m, 2H), 4.10(t, 2H), 6.00(m, 1H), 6.26(m, 1H), 7.33(m, 1H) |
| A.398 | $C_2H_5$ | Tetrahydropyran-4-yl | $-(CH_2)_3-$ | Furan-2-yl | 78–82 |
| A.399 | n-$C_3H_7$ | Tetrahydropyran-4-yl | $-(CH_2)_3-$ | Furan-2-yl | 48–52 |
| A.400 | $C_2H_5$ | Tetrahydrothiopyran-3-yl | $-(CH_2)_3-$ | Furan-2-yl | 54–58 |
| A.401 | n-$C_3H_7$ | Tetrahydrothiopyran-3-yl | $-(CH_2)_3-$ | Furan-2-yl | 4.10(t, 2H), 6.00(m, 1H), |

TABLE 7-continued

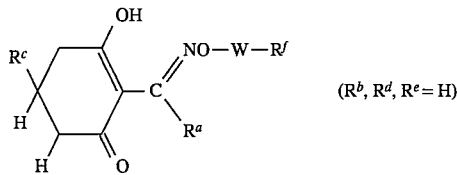

($R^b$, $R^d$, $R^e$ = H)

| No. | $R^a$ | $R^c$ | W | $R^f$ | Phys. data NMR data in ppm Mp. in °C. |
|---|---|---|---|---|---|
| A.402 | $C_2H_5$ | Tetrahydropyran-3-yl | —$(CH_2)_3$— | Thien-2-yl | 6.26(m, 1H), 7.33(m, 1H) 72–74 |
| A.403 | n-$C_3H_7$ | Tetrahydropyran-3-yl | —$(CH_2)_3$— | Thien-2-yl | 3.93(m, 2H), 4.10(t, 2H), 6.82(m, 1H), 6.93(m, 1H), 7.33(m, 1H) |
| A.404 | $C_2H_5$ | Tetrahydropyran-4-yl | —$(CH_2)_3$— | Thien-2-yl | 86–90 |
| A.405 | n-$C_3H_7$ | Tetrahydropyran-4-yl | —$(CH_2)_3$— | Thien-2-yl | 55–58 |
| A.406 | $C_2H_5$ | Tetrahydrothiopyran-3-yl | —$(CH_2)_3$— | Thien-2-yl | 4.12(t, 2H), 6.82(m, 1H), 6.93(m, 1H), 7.13(m, 1H), |
| A.407 | n-$C_3H_7$ | Tetrahydrothiopyran-3-yl | —$(CH_2)_3$— | Thien-2-yl | 4.12(t, 2H), 6.82(m, 1H), 6.93(m, 1H), 7.13(m, 1H), |
| A.408 | $C_2H_5$ | Tetrahydropyran-3-yl | —$(CH_2)_3$— | Thien-3-yl | 73–74 |
| A.409 | n-$C_3H_7$ | Tetrahydropyran-3-yl | —$(CH_2)_3$— | Thien-3-yl | 4.05(t, 2H), 6.95(m, 2H), 7.25(m, 1H) |
| A.410 | $C_2H_5$ | Tetrahydropyran-4-yl | —$(CH_2)_3$— | Thien-3-yl | 105–107 |
| A.411 | n-$C_3H_7$ | Tetrahydropyran-4-yl | —$(CH_2)_3$— | Thien-3-yl | 68–70 |
| A.412 | $C_2H_5$ | Tetrahydrothiopyran-3-yl | —$(CH_2)_3$— | Thien-3-yl | 57–59 |
| A.413 | n-$C_3H_7$ | Tetrahydrothiopyran-3-yl | —$(CH_2)_3$— | Thien-3-yl | 4.05(t, 2H), 6.95(m, 2H), 7.25(m, 1H) |
| A.414 | $C_2H_5$ | Tetrahydropyran-3-yl | —$(CH_2)_3$— | 1-$CH_3$-pyrrol-2-yl | 3.90(m, 2H), 4.12(t, 2H), 5.90(m, 1H), 6.06(m, 1H), 6.53(m, 1H) |
| A.415 | n-$C_3H_7$ | Tetrahydropyran-3-yl | —$(CH_2)_3$— | 1-$CH_3$-pyrrol-2-yl | 3.90(m, 2H), 4.12(t, 2H), 5.90(m, 1H), 6.06(m, 1H), 6.53(m, 1H) |
| A.416 | $C_2H_5$ | Tetrahydropyran-4-yl | —$(CH_2)_3$— | 1-$CH_3$-pyrrol-2-yl | 4.00(m, 2H), 4.12(t, 2H), 5.90(m, 1H), 6.06(m, 1H), 6.53(m, 1H) |
| A.417 | n-$C_3H_7$ | Tetrahydropyran-4-yl | —$(CH_2)_3$— | 1-$CH_3$-pyrrol-2-yl | 4.00(m, 2H), 4.12(t, 2H), 5.90(m, 1H), 6.06(m, 1H), 6.53(m, 1H) |
| A.418 | $C_2H_5$ | Tetrahydropyran-3-yl | —$(CH_2)_3$— | 1-$CH_3$-pyrrol-2-yl | 4.12(t, 2H), 5.90(m, 1H), 6.06(m, 1H), 6.53(m, 1H) |
| A.419 | n-$C_3H_7$ | Tetrahydropyran-3-yl | —$(CH_2)_3$— | 1-$CH_3$-pyrrol-2-yl | 4.12(t, 2H), 5.90, (m, 1H), 6.06(m, 1H), 6.53(m, 1H) |
| A.420 | $C_2H_5$ | Tetrahydropyran-3-yl | —$CH_2CH(CH_3)$—$CH_2$— | Thien-2-yl | 35 |
| A.421 | n-$C_3H_7$ | Tetrahydropyran-3-yl | —$CH_2CH(CH_3)$—$CH_2$— | Thien-2-yl | 6.85–7.20(m, 3H) |
| A.422 | $C_2H_5$ | Tetrahydropyran-4-yl | —$CH_2CH(CH_3)$—$CH_2$— | Thien-2-yl | 59–61 |
| A.423 | n-$C_3H_7$ | Tetrahydropyran-4-yl | —$CH_2CH(CH_3)$—$CH_2$— | Thien-2-yl | 6.70–7.20(m, 3H) |
| A.424 | $C_2H_5$ | Tetrahydrothiopyran-3-yl | —$CH_2CH(CH_3)$—$CH_2$— | Thien-2-yl | 6.70–7.20(m, 3H) |
| A.425 | n-$C_3H_7$ | Tetrahydrothiopyran-3-yl | —$CH_2CH(CH_3)$—$CH_2$— | Thien-2-yl | 6.70–7.20(m, 3H) |
| A.426 | $C_2H_5$ | Tetrahydropyran-3-yl | —$CH_2CH(CH_3)$—$CH_2$— | Thien-3-yl | 38–40 |
| A.427 | n-$C_3H_7$ | Tetrahydropyran-3-yl | —$CH_2CH(CH_3)$—$CH_2$— | Thien-3-yl | 6.80–7.30(m, 3H) |
| A.428 | $C_2H_5$ | Tetrahydropyran-4-yl | —$CH_2CH(CH_3)$—$CH_2$— | Thien-3-yl | 58–60 |
| A.429 | n-$C_3H_7$ | Tetrahydropyran-4-yl | —$CH_2CH(CH_3)$—$CH_2$— | Thien-3-yl | 6.80–7.40(m, 3H) |
| A.430 | $C_2H_5$ | Tetrahydrothiopyran-3-yl | —$CH_2CH(CH_3)$—$CH_2$— | Thien-3-yl | 6.90(m, 2H), 7.25(m, 1H) |
| A.431 | n-$C_3H_7$ | Tetrahydrothiopyran-3-yl | —$CH_2CH(CH_3)$—$CH_2$— | Thien-3-yl | 6.90(m, 2H), 7.30(m, 1H) |
| A.432 | $C_2H_5$ | Tetrahydropyran-3-yl | —$CH_2CH(CH_3)$—$CH_2$— | 5-$CH_3$-thien-2-yl | 48–50 |
| A.433 | n-$C_3H_7$ | Tetrahydropyran-3-yl | —$CH_2CH(CH_3)$—$CH_2$— | 5-$CH_3$-thien-2-yl | 2.40(s, 3H), 6.55(s, 2H) |
| A.434 | $C_2H_5$ | Tetrahydropyran-4-yl | —$CH_2CH(CH_3)$—$CH_2$— | 5-$CH_3$-thien-2-yl | 2.40(s, 3H), 6.55(s, 2H) |
| A.435 | n-$C_3H_7$ | Tetrahydropyran-4-yl | —$CH_2CH(CH_3)$—$CH_2$— | 5-$CH_3$-thien-2-yl | 2.40(s, 3H), 6.55(s, 2H) |
| A.436 | $C_2H_5$ | Tetrahydrothiopyran-3-yl | —$CH_2CH(CH_3)$—$CH_2$— | 5-$CH_3$-thien-2-yl | 2.45(s, 3H), 6.75(s, 2H) |
| A.437 | n-$C_3H_7$ | Tetrahydrothiopyran-3-yl | —$CH_2CH(CH_3)$—$CH_2$— | 5-$CH_3$-thien-2-yl | 56–58 |
| A.438 | $C_2H_5$ | Tetrahydropyran-3-yl | —$CH_2CH=CH$— | Furan-2-yl | 4.70(d, 2H), 6.10–6.60(m, 4H), 7.40(s, 1H) |
| A.439 | n-$C_3H_7$ | Tetrahydropyran-3-yl | —$CH_2CH=CH$— | Furan-2-yl | 4.70(d, 2H), 6.00–6.60(m, 4H), 7.40(s, 1H) |
| A.440 | $C_2H_5$ | Tetrahydropyran-4-yl | —$CH_2CH=CH$— | Furan-2-yl | 99–100 |
| A.441 | n-$C_3H_7$ | Tetrahydropyran-4-yl | —$CH_2CH=CH$— | Furan-2-yl | 4.70(d, 2H), 6.10–6.60(m, 4H), 7.40(s, 1H) |
| A.442 | $C_2H_5$ | Tetrahydrothiopyran-3-yl | —$CH_2CH=CH$— | Furan-2-yl | 4.65(d, 2H), 6.10–6.60(m, 4H), 7.40(s, 1H) |
| A.443 | n-$C_3H_7$ | Tetrahydrothiopyran-3-yl | —$CH_2CH=CH$— | Furan-2-yl | 4.70(d, 2H), 6.10–6.60(m, 4H), 7.40(s, 1H) |
| A.444 | $C_2H_5$ | Tetrahydrothiopyran-3-yl | —$CH_2CH=CH$— | 5-Cl-thien-2-yl | 4.60(d, 2H), 6.00(dt, 1H), 6.70(d, 1H), 6.80(m, 2H) |

TABLE 7-continued

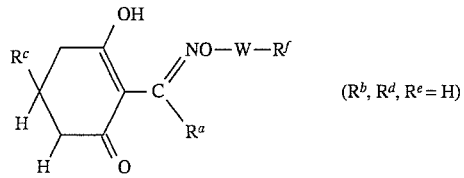

($R^b$, $R^d$, $R^e$ = H)

| No. | $R^a$ | $R^c$ | W | $R^f$ | Phys. data<br>NMR data in ppm<br>Mp. in °C. |
|---|---|---|---|---|---|
| A.445 | n-$C_3H_7$ | Tetrahydrothiopyran-3-yl | —$CH_2CH$=$CH$— | 5-Cl-thien-2-yl | 4.60(d, 2H), 6.00(dt, 1H),<br>6.70(d, 1H), 6.80(m, 2H) |
| A.446 | $C_2H_5$ | Tetrahydropyran-3-yl | —$CH_2CH$=$CH$— | Thien-2-yl | 112–114 |
| A.447 | n-$C_3H_7$ | Tetrahydropyran-3-yl | —$CH_2CH$=$CH$— | Thien-2-yl | 67–68 |
| A.448 | $C_2H_5$ | Tetrahydropyran-4-yl | —$CH_2CH$=$CH$— | Thien-2-yl | 123–125 |
| A.449 | n-$C_3H_7$ | Tetrahydropyran-4-yl | —$CH_2CH$=$CH$— | Thien-2-yl | 70–72 |
| A.450 | $C_2H_5$ | Tetrahydrothiopyran-3-yl | —$CH_2CH$=$CH$— | Thien-2-yl | 104–106 |
| A.451 | n-$C_3H_7$ | Tetrahydrothiopyran-3-yl | —$CH_2CH$=$CH$— | Thien-2-yl | 85–88 |
| A.452 | $C_2H_5$ | 2,4,6-Trimethylphenyl | —$CH_2CH$=$CH$— | Thien-2-yl | 4.65(d, 2H), 6.10–6.30(m, 1H)<br>6.70–7.20(m, 6H) |
| A.453 | $C_2H_5$ | Tetrahydropyran-3-yl | —$CH_2CH$=$CH$— | Thien-3-yl | 87–90 |
| A.454 | n-$C_3H_7$ | Tetrahydropyran-3-yl | —$CH_2CH$=$CH$— | Thien-3-yl | 3.90(m, 2H), 4.67(d, 2H),<br>6.12(dt, 1H), 6.63(d, 1H),<br>7.20(m, 3H) |
| A.455 | $C_2H_5$ | Tetrahydropyran-4-yl | —$CH_2CH$=$CH$— | Thien-3-yl | 128–135 |
| A.456 | n-$C_3H_7$ | Tetrahydropyran-4-yl | —$CH_2CH$=$CH$— | Thien-3-yl | 92–95 |
| A.457 | $C_2H_5$ | Tetrahydrothiopyran-3-yl | —$CH_2CH$=$CH$— | Thien-3-yl | 79–81 |
| A.458 | n-$C_3H_7$ | Tetrahydrothiopyran-3-yl | —$CH_2CH$=$CH$— | Thien-3-yl | 86–92 |
| A.459 | $C_2H_5$ | Tetrahydropyran-3-yl | —$CH_2CH$=$CH$— | 5-$CH_3$-thien-2-yl | 88–89 |
| A.460 | n-$C_3H_7$ | Tetrahydropyran-3-yl | —$CH_2CH$=$CH$— | 5-$CH_3$-thien-2-yl | 70–71 |
| A.461 | $C_2H_5$ | Tetrahydropyran-4-yl | —$CH_2CH$=$CH$— | 5-$CH_3$-thien-2-yl | 108–110 |
| A.462 | n-$C_3H_7$ | Tetrahydropyran-4-yl | —$CH_2CH$=$CH$— | 5-$CH_3$-thien-2-yl | 104–105 |
| A.463 | $C_2H_5$ | Tetrahydrothiopyran-3-yl | —$CH_2CH$=$CH$— | 5-$CH_3$-thien-2-yl | 111–112 |
| A.464 | n-$C_3H_7$ | Tetrahydrothiopyran-3-yl | —$CH_2CH$=$CH$— | 5-$CH_3$-thien-2-yl | 75–77 |
| A.465 | $C_2H_5$ | Tetrahydropyran-3-yl | —$CH_2CH$=$CH$— | 4-Br-thien-2-yl | 78–80 |
| A.466 | n-$C_3H_7$ | Tetrahydropyran-3-yl | —$CH_2CH$=$CH$— | 4-Br-thien-2-yl | 6.70(d, 1H), 6.95(s, 1H),<br>7.05(s, 1H) |
| A.467 | $C_2H_5$ | Tetrahydropyran-4-yl | —$CH_2CH$=$CH$— | 4-Br-thien-2-yl | 122–124 |
| A.468 | n-$C_3H_7$ | Tetrahydropyran-4-yl | —$CH_2CH$=$CH$— | 4-Br-thien-2-yl | 88–90 |
| A.469 | $C_2H_5$ | Tetrahydrothiopyran-3-yl | —$CH_2CH$=$CH$— | 4-Br-thien-2-yl | 72–74 |
| A.470 | n-$C_3H_7$ | Tetrahydrothiopyran-3-yl | —$CH_2CH$=$CH$— | 4-Br-thien-2-yl | 6.70(d, 1H), 6.90(s, 1H),<br>7.05(s, 1H) |
| A.471 | $C_2H_5$ | Tetrahydropyran-3-yl | —$CH_2CH$=$CH$— | Pyrid-3-yl | 146–148 |
| A.472 | n-$C_3H_7$ | Tetrahydropyran-3-yl | —$CH_2CH$=$CH$— | Pyrid-3-yl | 6.40(dt, 1H), 7.30, 7.75,<br>8.40–8.70(3m, 4H) |
| A.473 | $C_2H_5$ | Tetrahydropyran-4-yl | —$CH_2CH$=$CH$— | Pyrid-3-yl | 164–165 |
| A.474 | n-$C_3H_7$ | Tetrahydropyran-4-yl | —$CH_2CH$=$CH$— | Pyrid-3-yl | 73–78 |
| A.475 | $C_2H_5$ | Tetrahydrothiopyran-3-yl | —$CH_2CH$=$CH$— | Pyrid-3-yl | 6.40(dt, 1H), 7.30, 7.75,<br>8.40–8.70(3m, 4H) |
| A.476 | n-$C_3H_7$ | Tetrahydrothiopyran-3-yl | —$CH_2CH$=$CH$— | Pyrid-3-yl | 6.40(dt, 1H), 7.30, 7.75,<br>8.40–8.70(3m, 4H) |
| A.477 | $C_2H_5$ | Tetrahydropyran-3-yl | —$CH_2C(CH_3)$=$CH$— | Thien-2-yl | |
| A.478 | n-$C_3H_7$ | Tetrahydropyran-3-yl | —$CH_2C(CH_3)$=$CH$— | Thien-2-yl | |
| A.479 | $C_2H_5$ | Tetrahydropyran-4-yl | —$CH_2C(CH_3)$=$CH$— | Thien-2-yl | 97–98 |
| A.480 | n-$C_3H_7$ | Tetrahydropyran-4-yl | —$CH_2C(CH_3)$=$CH$— | Thien-2-yl | 6.65(s, 1H), 6.90–7.30(2m, 3H), |
| A.481 | $C_2H_5$ | Tetrahydrothiopyran-3-yl | —$CH_2C(CH_3)$=$CH$— | Thien-2-yl | 88–90 |
| A.482 | n-$C_3H_7$ | Tetrahydrothiopyran-3-yl | —$CH_2C(CH_3)$=$CH$— | Thien-2-yl | 6.65(s, 1H), 6.90–7.80(2m, 3H), |
| A.483 | $C_2H_5$ | Tetrahydropyran-3-yl | —$CH_2C(CH_3)$=$CH$— | Thien-3-yl | 6.50(s, 1H), 7.00–7.40(m, 3H) |
| A.484 | n-$C_3H_7$ | Tetrahydropyran-3-yl | —$CH_2C(CH_3)$=$CH$— | Thien-3-yl | 6.50(s, 1H), 7.00–7.40(m, 3H) |
| A.485 | $C_2H_5$ | Tetrahydropyran-4-yl | —$CH_2C(CH_3)$=$CH$— | Thien-3-yl | 88–90 |
| A.486 | n-$C_3H_7$ | Tetrahydropyran-4-yl | —$CH_2C(CH_3)$=$CH$— | Thien-3-yl | 6.55(s, 1H), 7.00–7.40(m, 3H), |
| A.487 | $C_2H_5$ | Tetrahydrothiopyran-3-yl | —$CH_2C(CH_3)$=$CH$— | Thien-3-yl | 6.55(s, 1H), 7.00–7.40(m, 3H) |
| A.488 | n-$C_3H_7$ | Tetrahydrothiopyran-3-yl | —$CH_2C(CH_3)$=$CH$— | Thien-3-yl | 6.50(s, 1H), 7.00–7.40(m, 3H), |
| A.489 | $C_2H_5$ | Tetrahydropyran-3-yl | —$CH_2C(CH_3)$=$CH$— | 5-$CH_3$-thien-2-yl | 108–110 |
| A.490 | n-$C_3H_7$ | Tetrahydropyran-3-yl | —$CH_2C(CH_3)$=$CH$— | 5-$CH_3$-thien-2-yl | 6.60(s, 1H), 6.65–7.00(m, 2H) |
| A.491 | $C_2H_5$ | Tetrahydropyran-4-yl | —$CH_2C(CH_3)$=$CH$— | 5-$CH_3$-thien-2-yl | 111–112 |
| A.492 | n-$C_3H_7$ | Tetrahydropyran-4-yl | —$CH_2C(CH_3)$=$CH$— | 5-$CH_3$-thien-2-yl | 6.60(s, 1H), 6.65–7.00(m, 2H), |
| A.493 | $C_2H_5$ | Tetrahydrothiopyran-3-yl | —$CH_2C(CH_3)$=$CH$— | 5-$CH_3$-thien-2-yl | 119–120 |
| A.494 | n-$C_3H_7$ | Tetrahydrothiopyran-3-yl | —$CH_2C(CH_3)$=$CH$— | 5-$CH_3$-thien-2-yl | 6.55(s, 1H), 6.60–7.00(m, 2H), |
| A.495 | $C_2H_5$ | Tetrahydropyran-3-yl | —$CH_2C(CH_3)$=$CH$— | 5-Cl-thien-2-yl | 82–85 |
| A.496 | n-$C_3H_7$ | Tetrahydropyran-3-yl | —$CH_2C(CH_3)$=$CH$— | 5-Cl-thien-2-yl | 6.70(s, 1H), 6.90(m, 2H) |
| A.497 | $C_2H_5$ | Tetrahydropyran-4-yl | —$CH_2C(CH_3)$=$CH$— | 5-Cl-thien-2-yl | 124–126 |
| A.498 | n-$C_3H_7$ | Tetrahydropyran-4-yl | —$CH_2C(CH_3)$=$CH$— | 5-Cl-thien-2-yl | 97–98 |
| A.499 | $C_2H_5$ | Tetrahydrothiopyran-3-yl | —$CH_2C(CH_3)$=$CH$— | 5-Cl-thien-2-yl | 103–105 |
| A.500 | n-$C_3H_7$ | Tetrahydrothiopyran-3-yl | —$CH_2C(CH_3)$=$CH$— | 5-Cl-thien-2-yl | 6.65(s, 1H), 6.90(m, 2H), |
| A.501 | $C_2H_5$ | Tetrahydropyran-3-yl | —$(CH_2)_4$— | Furan-2-yl | 3.93(m, 2H), 4.07(m, 2H), |

TABLE 7-continued (R$^b$, R$^d$, R$^e$ = H)

| No. | R$^a$ | R$^c$ | W | R$^f$ | Phys. data NMR data in ppm Mp. in °C. |
|---|---|---|---|---|---|
| | | | | | 6.00(m, 1H), 6.26(m, 1H), 7.30(m, 1H) |
| A.502 | n-C$_3$H$_7$ | Tetrahydropyran-3-yl | —(CH$_2$)$_4$— | Furan-2-yl | 3.93(m, 2H), 4.07(m, 2H), 6.00(m, 1H), 6.26(m, 1H), 7.30(m, 1H) |
| A.503 | C$_2$H$_5$ | Tetrahydropyran-4-yl | —(CH$_2$)$_4$— | Furan-2-yl | 3.90–4.13(m, 4H), 6.00(m, 1H), 6.26(m, 1H), 7.30(m, 1H) |
| A.504 | n-C$_3$H$_7$ | Tetrahydropyran-4-yl | —(CH$_2$)$_4$— | Furan-2-yl | 3.90–4.13(m, 4H), 6.00(m, 1H), 6.26(m, 1H), 7.30(m, 1H) |
| A.505 | C$_2$H$_5$ | Tetrahydrothiopyran-3-yl | —(CH$_2$)$_4$— | Furan-2-yl | 4.05(m, 2H), 6.00(m, 1H), 6.26(m, 1H), 7.30(m, 1H) |
| A.506 | n-C$_3$H$_7$ | Tetrahydrothiopyran-3-yl | —(CH$_2$)$_4$— | Furan-2-yl | 4.05(m, 2H), 6.00(m, 1H), 6.26(m, 1H), 7.30(m, 1H) |
| A.507 A. | C$_2$H$_5$ | Tetrahydropyran-3-yl | —(CH$_2$)$_4$— | 5-CH$_3$-furan-2-yl | 62–64 |
| A.508 | n-C$_3$H$_7$ | Tetrahydropyran-3-yl | —(CH$_2$)$_4$— | 5-CH$_3$-furan-2-yl | 3.93(m, 2H), 4.07(m, 2H), 5.87(m, 2H) |
| A.509 | C$_2$H$_5$ | Tetrahydropyran-4-yl | —(CH$_2$)$_4$— | 5-CH$_3$-furan-2-yl | 76–78 |
| A.510 | n-C$_3$H$_7$ | Tetrahydropyran-4-yl | —(CH$_2$)$_4$— | 5-CH$_3$-furan-2-yl | 3.90–4.15(m, 4H), 5.87(m, 2H) |
| A.511 | C$_2$H$_5$ | Tetrahydrothiopyran-3-yl | —(CH$_2$)$_4$— | 5-CH$_3$-furan-2-yl | 4.07(m, 2H), 5.87(m, 2H) |
| A.512 | n-C$_3$H$_7$ | Tetrahydrothiopyran-3-yl | —(CH$_2$)$_4$— | 5-CH$_3$-furan-2-yl | 4.07(m, 2H), 5.87(m, 2H) |
| A.513 | C$_2$H$_5$ | Tetrahydropyran-3-yl | —(CH$_2$)$_4$— | Thien-2-yl | 3.80–4.15(m, 4H), 6.80(dd, 1H), 6.93(dd, 1H), 7.13(dd, 1H) |
| A.514 | n-C$_3$H$_7$ | Tetrahydropyran-3-yl | —(CH$_2$)$_4$— | Thien-2-yl | 3.80–4.15(m, 4H), 6.80(dd, 1H), 6.93(dd, 1H), 7.13(dd, 1H) |
| A.515 | C$_2$H$_5$ | Tetrahydropyran-4-yl | —(CH$_2$)$_4$— | Thien-2-yl | 3.90–4.23(m, 4H), 6.80(dd, 1H), 6.93(dd, 1H), 7.13(dd, 1H) |
| A.516 | n-C$_3$H$_7$ | Tetrahydropyran-4-yl | —(CH$_2$)$_4$— | Thien-2-yl | 3.90–4.23(m, 4H), 6.80(dd, 1H), 6.93(dd, 1H), 7.13(dd, 1H) |
| A.517 | C$_2$H$_5$ | Tetrahydrothiopyran-3-yl | —(CH$_2$)$_4$— | Thien-2-yl | 4.06(m, 2H), 6.80(dd, 1H), 6.93(dd, 1H), 7.13(dd, 1H) |
| A.518 | n-C$_3$H$_7$ | Tetrahydrothiopyran-3-yl | —(CH$_2$)$_4$— | Thien-2-yl | 4.06(m, 2H), 6.80(dd, 1H), 6.93(dd, 1H), 7.13(dd, 1H) |
| A.519 | C$_2$H$_5$ | Tetrahydropyran-3-yl | —(CH$_2$)$_4$— | 5-CH$_3$-thien-2-yl | 3.85–4.13(m, 4H), 6.53(s, 2H) |
| A.520 | n-C$_3$H$_7$ | Tetrahydropyran-3-yl | —(CH$_2$)$_4$— | 5-CH$_3$-thien-2-yl | 3.80–4.13(m, 4H), 6.53(s, 2H) |
| A.521 | C$_2$H$_5$ | Tetrahydropyran-4-yl | —(CH$_2$)$_4$— | 5-CH$_3$-thien-2-yl | 3.90–4.15(m, 4H), 6.50(s, 2H) |
| A.522 | n-C$_3$H$_7$ | Tetrahydropyran-4-yl | —(CH$_2$)$_4$— | 5-CH$_3$-thien-2-yl | 3.94–4.15(m, 4H), 6.53(s, 2H) |
| A.523 | C$_2$H$_5$ | Tetrahydrothiopyran-3-yl | —(CH$_2$)$_4$— | 5-CH$_3$-thien-2-yl | 4.08(m, 2H), 6.55(s, 2H) |
| A.524 | n-C$_3$H$_7$ | Tetrahydrothiopyran-3-yl | —(CH$_2$)$_4$— | 5-CH$_3$-thien-2-yl | 4.08(m, 2H), 6.56(s, 2H) |
| A.525 | C$_2$H$_5$ | Tetrahydropyran-3-yl | —(CH$_2$)$_4$— | 5-Cl-thien-2-yl | 3.93(m, 2H), 4.10(m, 2H), 6.53(d, 1H), 6.70(d, 1H) |
| A.526 | n-C$_3$H$_7$ | Tetrahydropyran-3-yl | —(CH$_2$)$_4$— | 5-Cl-thien-2-yl | 3.93(m, 2H), 4.10(m, 2H), 6.53(d, 1H), 6.70(d, 1H) |
| A.527 | C$_2$H$_5$ | Tetrahydropyran-4-yl | —(CH$_2$)$_4$— | 5-Cl-thien-2-yl | 3.90–4.10(m, 4H), 6.53(d, 1H), 6.70(d, 1H) |
| A.528 | n-C$_3$H$_7$ | Tetrahydropyran-4-yl | —(CH$_2$)$_4$— | 5-Cl-thien-2-yl | 3.90–4.10(m, 4H), 6.53(d, 1H), 6.70(d, 1H) |
| A.529 | C$_2$H$_5$ | Tetrahydrothiopyran-3-yl | —(CH$_2$)$_4$— | 5-Cl-thien-2-yl | 4.10(m, 2H), 6.53(d, 1H), 6.70(d, 1H) |
| A.530 | n-C$_3$H$_7$ | Tetrahydrothiopyran-3-yl | —(CH$_2$)$_4$— | 5-Cl-thien-2-yl | 4.10(m, 2H), 6.53(d, 1H), 6.70(d, 1H) |
| A.531 | C$_2$H$_5$ | Tetrahydropyran-3-yl | —(CH$_2$)$_4$— | 5-C$_2$H$_5$-thien-2-yl | 3.80–4.09(m, 4H), 6.60(s, 2H) |
| A.532 | n-C$_3$H$_7$ | Tetrahydropyran-3-yl | —(CH$_2$)$_4$— | 5-C$_2$H$_5$-thien-2-yl | 3.80–4.09(m, 4H), 6.60(s, 2H) |
| A.533 | C$_2$H$_5$ | Tetrahydropyran-4-yl | —(CH$_2$)$_4$— | 5-C$_2$H$_5$-thien-2-yl | 3.93–4.09(m, 4H), 6.60(s, 2H) |
| A.534 | n-C$_3$H$_7$ | Tetrahydropyran-4-yl | —(CH$_2$)$_4$— | 5-C$_2$H$_5$-thien-2-yl | 3.93–4.09(m, 4H), 6.60(s, 2H) |
| A.535 | C$_2$H$_5$ | Tetrahydrothiopyran-3-yl | —(CH$_2$)$_4$— | 5-C$_2$H$_5$-thien-2-yl | 4.03(m, 2H), 6.60(s, 2H) |
| A.536 | n-C$_3$H$_7$ | Tetrahydrothiopyran-3-yl | —(CH$_2$)$_4$— | 5-C$_2$H$_5$-thien-2-yl | 4.03(m, 2H), 6.60(s, 2H) |
| A.537 | C$_2$H$_5$ | Tetrahydropyran-3-yl | —(CH$_2$)$_4$— | 1-CH$_3$-pyrrol-2-yl | 64–66 |
| A.538 | n-C$_3$H$_7$ | Tetrahydropyran-3-yl | —(CH$_2$)$_4$— | 1-CH$_3$-pyrrol-2-yl | 3.90(m, 2H), 4.09(t, 2H), 5.87(m, 1H), 6.03(m, 1H), 6.53(m, 1H) |
| A.539 | C$_2$H$_5$ | Tetrahydropyran-4-yl | —(CH$_2$)$_4$— | 1-CH$_3$-pyrrol-2-yl | 82–84 |
| A.540 | n-C$_3$H$_7$ | Tetrahydropyran-4-yl | —(CH$_2$)$_4$— | 1-CH$_3$-pyrrol-2-yl | 4.00(m, 22), 4.09(t, 2H), 5.87(m, 1H), 6.03(m, 1H), 6.53(m, 1H) |
| A.541 | C$_2$H$_5$ | Tetrahydrothiopyran-3-yl | —(CH$_2$)$_4$— | 1-CH$_3$-pyrrol-2-yl | 4.09(t, 2H), 5.87(m, 1H), |

TABLE 7-continued

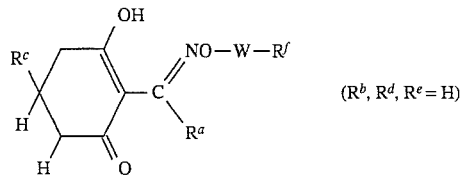

($R^b$, $R^d$, $R^e$ = H)

| No. | $R^a$ | $R^c$ | W | $R^f$ | Phys. data NMR data in ppm Mp. in °C. |
|---|---|---|---|---|---|
| A.542 | n-$C_3H_7$ | Tetrahydrothiopyran-3-yl | —$(CH_2)_4$— | 1-$CH_3$-pyrrol-2-yl | 6.03(m, 1H), 6.53(m, 1H) 4.09(t, 2H), 5.87(m, 1H), 6.03(m, 1H), 6.53(m, 1H) |
| A.543 | $C_2H_5$ | Tetrahydropyran-4-yl | —$CH_2CH_2CH=CH$— | Furan-2-yl | 4.13(t, 2H), 6.00–6.42(m, 4H), 7.33(bs, 1H) |
| A.544 | $C_2H_5$ | Tetrahydropyran-3-yl | —$CH_2CH_2CH=CH$— | Furan-3-yl | 4.13(t, 2H), 5.92(m, 1H), 6.33(d, 1H), 6.55(bs, 1H), 7.40(d, 2H) |
| A.545 | $C_2H_5$ | Tetrahydropyran-4-yl | —$CH_2CH_2CH=CH$— | Furan-3-yl | 4.13(m, 2H), 5.92(m, 1H), 6.33(d, 1H), 6.55(s, 1H), 7.40(d, 2H) |
| A.546 | $C_2H_5$ | Tetrahydrothiopyran-3-yl | —$CH_2CH_2CH=CH$— | Furan-3-yl | 4.13(t, 2H), 5.92(m, 1H), 6.33(d, 1H), 6.55(bs, 1H), 7.40(d, 2H) |
| A.547 | $C_2H_5$ | Tetrahydropyran-3-yl | —$CH_2CH_2CH=CH$— | Thien-2-yl | 4.15(t, 2H), 6.00(dt, 1H), 6.60(d, 1H), 6.90(m, 2H), 7.10(d, 1H) |
| A.548 | n-$C_3H_7$ | Tetrahydropyran-3-yl | —$CH_2CH_2CH=CH$— | Thien-2-yl | 4.10(t, 2H), 6.00(dt, 1H), 6.60(d, 1H), 6.80–7.20(m, 3H) |
| A.549 | $C_2H_5$ | Tetrahydropyran-4-yl | —$CH_2CH_2$—$CH=CH$— | Thien-2-yl | 4.15(t, 2H), 6.00(dt, 1H), 6.60(d, 1H), 6.80–7.20(m, 3H) |
| A.550 | n-$C_3H_7$ | Tetrahydropyran-4-yl | —$CH_2CH_2$—$CH=CH$— | Thien-2-yl | 4.15(t, 2H), 6.00(dt, 1H), 6.60(d, 1H), 6.80–7.20(m, 3H) |
| A.551 | $C_2H_5$ | Tetrahydrothiopyran-3-yl | —$CH_2CH_2$—$CH=CH$— | Thien-2-yl | 4.15(t, 2H), 6.00(dt, 1H), 6.60(d, 1H), 6.80–7.20(m, 3H), |
| A.552 | n-$C_3H_7$ | Tetrahydrothiopyran-3-yl | —$CH_2CH_2$—$CH=CH$— | Thien-2-yl | 4.15(t, 2H), 6.00(dt, 1H), 6.60(d, 1H), 6.80–7.30(m, 3H) |
| A.553 | $C_2H_5$ | 2,4,6-Trimethylphenyl | —$CH_2CH_2$—$CH=CH$— | Thien-2-yl | 4.20(t, 2H), 6.10(dt, 1H), 6.60(d, 1H), 6.80–7.20(m, 5H) |
| A.554 | $C_2H_5$ | Tetrahydropyran-3-yl | —$CH_2CH_2$—$CH=CH$— | 5-$CH_3$-thien-2-yl | 4.13(t, 2H), 5.87(dt, 1H), 6.37–6.73(m, 3H) |
| A.555 | n-$C_3H_7$ | Tetrahydropyran-3-yl | —$CH_2CH_2$—$CH=CH$— | 5-$CH_3$-thien-2-yl | 4.13(t, 2H), 5.87(dt, 1H), 6.37–6.73(m, 3H) |
| A.556 | $C_2H_5$ | Tetrahydropyran-4-yl | —$CH_2CH_2$—$CH=CH$— | 5-$CH_3$-thien-2-yl | 4.13(t, 2H), 5.87(dt, 1H), 6.37–6.73(m, 3H) |
| A.557 | n-$C_3H_7$ | Tetrahydropyran-4-yl | —$CH_2CH_2$—$CH=CH$— | 5-$CH_3$-thien-2-yl | 4.13(t, 2H), 5.87(dt, 1H), 6.37–6.73(m, 3H) |
| A.558 | $C_2H_5$ | Tetrahydrothiopyran-3-yl | —$CH_2CH_2$—$CH=CH$— | 5-$CH_3$-thien-2-yl | 4.13(t, 2H), 5.88(dt, 1H), 6.37–6.73(m, 3H) |
| A.559 | n-$C_3H_7$ | Tetrahydrothiopyran-3-yl | —$CH_2CH_2$—$CH=CH$— | 5-$CH_3$-thien-2-yl | 4.13(t, 2H), 5.88(dt, 1H), 6.37–6.73(m, 3H) |
| A.560 | $C_2H_5$ | Tetrahydropyran-3-yl | —$CH_2CH_2$—$CH=CH$— | 5-Cl-thien-2-yl | 4.15(t, 2H), 5.93(dt, 1H), 6.46(d, 1H), 6.63(d, 1H), 6.75(d, 1H) |
| A.561 | n-$C_3H_7$ | Tetrahydropyran-3-yl | —$CH_2CH_2$—$CH=CH$— | 5-Cl-thien-2-yl | 4.15(t, 2H), 5.93(dt, 1H), 6.46(d, 1H), 6.63(d, 1H), 6.75(d, 1H) |
| A.562 | $C_2H_5$ | Tetrahydropyran-4-yl | —$CH_2CH_2$—$CH=CH$— | 5-Cl-thien-2-yl | 4.15(t, 2H), 5.93(dt, 1H), 6.46(d, 1H), 6.63(d, 1H), 6.75(d, 1H) |
| A.563 | n-$C_3H_7$ | Tetrahydropyran-4-yl | —$CH_2CH_2$—$CH=CH$— | 5-Cl-thien-2-yl | 4.15(t, 2H), 5.93(dt, 1H), 6.46(d, 1H), 6.63(d, 1H), 6.75(d, 1H) |
| A.564 | $C_2H_5$ | Tetrahydrothiopyran-3-yl | —$CH_2CH_2$—$CH=CH$— | 5-Cl-thien-2-yl | 4.15(t, 2H), 5.93(dt, 1H), 6.46(d, 1H), 6.63(d, 1H), 6.75(d, 1H) |
| A.565 | n-$C_3H_7$ | Tetrahydrothiopyran-3-yl | —$CH_2CH_2$—$CH=CH$— | 5-Cl-thien-2-yl | 4.15(t, 2H), 5.93(dt, 1H), 6.46(d, 1H), 6.63(d, 1H), 6.75(d, 1H) |
| A.566 | $C_2H_5$ | Tetrahydropyran-3-yl | —$CH_2CH_2$—$CH=CH$— | Thien-3-yl | 4.15(t, 2H), 6.07(dt, 1H), 6.50(d, 1H), 7.00–7.32(m, 3H) |
| A.567 | n-$C_3H_7$ | Tetrahydropyran-3-yl | —$CH_2CH_2$—$CH=CH$— | Thien-3-yl | 4.15(t, 2H), 6.07(dt, 1H), 6.50(d, 1H), 7.00–7.32(m, 3H) |
| A.568 | $C_2H_5$ | Tetrahydropyran-4-yl | —$CH_2CH_2$—$CH=CH$— | Thien-3-yl | 4.20(t, 2H), 6.07(dt, 1H), 6.50(d, 1H), 7.03–7.32(m, 3H) |
| A.569 | n-$C_3H_7$ | Tetrahydropyran-4-yl | —$CH_2CH_2$—$CH=CH$— | Thien-3-yl | 4.20(t, 2H), 6.07(dt, 1H), |

TABLE 7-continued

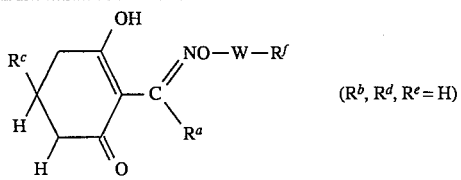

($R^b$, $R^d$, $R^e$ = H)

| No. | $R^a$ | $R^c$ | W | $R^f$ | Phys. data NMR data in ppm Mp. in °C. |
|---|---|---|---|---|---|
| A.570 | $C_2H_5$ | Tetrahydrothiopyran-3-yl | —$CH_2CH_2$—CH=CH— | Thien-3-yl | 6.50(d, 1H), 7.03–7.32(m, 3H) 4.17(t, 2H), 6.07(dt, 1H), |
| A.571 | n-$C_3H_7$ | Tetrahydrothiopyran-3-yl | —$CH_2CH_2$—CH=CH— | Thien-3-yl | 6.50(d, 1H), 7.00–7.36(m, 3H) 4.17(t, 2H), 6.07(dt, 1H), |
| A.572 | $C_2H_5$ | Tetrahydropyran-3-yl | —$CH_2CH_2$—CH=CH— | 2-Cl-thien-3-yl | 6.50(d, 1H), 7.00–7.36(m, 3H) 4.20(t, 2H), 6.10(dt, 1H), |
| A.573 | n-$C_3H_7$ | Tetrahydropyran-3-yl | —$CH_2CH_2$—CH=CH— | 2-Cl-thien-3-yl | 6.52(d, 1H), 7.05(s, 2H), 4.20(t, 2H), 6.10(dt, 1H), |
| A.574 | $C_2H_5$ | Tetrahydropyran-4-yl | —$CH_2CH_2$—CH=CH— | 2-Cl-thien-3-yl | 6.52(d, 1H), 7.05(s, 2H), 4.20(t, 2H), 6.13(dt, 1H), |
| A.575 | n-$C_3H_7$ | Tetrahydropyran-4-yl | —$CH_2CH_2$—CH=CH— | 2-Cl-thien-3-yl | 6.52(d, 1H), 7.07(s, 2H), 4.20(t, 2H), 6.13(dt, 1H), |
| A.576 | $C_2H_5$ | Tetrahydrothiopyran-3-yl | —$CH_2CH_2$—CH=CH— | 2-Cl-thien-3-yl | 6.52(d, 1H), 7.07(s, 2H), 4.20(t, 2H), 6.12(dt, 1H), |
| A.577 | n-$C_3H_7$ | Tetrahydrothiopyran-3-yl | —$CH_2CH_2$—CH=CH— | 2-Cl-thien-3-yl | 6.53(d, 1H), 7.10(s, 2H), 4.20(t, 2H), 6.12(dt, 1H), |
| A.578 | $C_2H_5$ | Tetrahydropyran-3-yl | —$CH_2CH_2$—CH=CH— | 5-Cl-thien-3-yl | 6.53(d, 1H), 7.10(s, 2H), 4.17(t, 2H), 6.00(dt, 1H), 6.33(d, 1H), 6.83(s, 1H), 7.03(s, 1H) |
| A.579 | n-$C_3H_7$ | Tetrahydropyran-3-yl | —$CH_2CH_2$—CH=CH— | 5-Cl-thien-3-yl | 4.17(t, 2H), 6.00(dt, 1H), 6.33(d, 1H), 6.83(s, 1H), 7.03(s, 1H) |
| A.580 | $C_2H_5$ | Tetrahydropyran-4-yl | —$CH_2CH_2$—CH=CH— | 5-Cl-thien-3-yl | 4.17(t, 2H), 6.00(dt, 1H), 6.33(d, 1H), 6.83(s, 1H), 7.03(s, 1H) |
| A.581 | n-$C_3H_7$ | Tetrahydropyran-4-yl | —$CH_2CH_2$—CH=CH— | 5-Cl-thien-3-yl | 4.17(t, 2H), 6.00(dt, 1H), 6.33(d, 1H), 6.83(s, 1H), 7.03(s, 1H) |
| A.582 | $C_2H_5$ | Tetrahydrothiopyran-3-yl | —$CH_2CH_2$—CH=CH— | 5-Cl-thien-3-yl | 4.20(t, 2H), 6.00(dt, 1H), 6.33(d, 1H), 6.83(s, 1H), 7.03(s, 1H) |
| A.583 | n-$C_3H_7$ | Tetrahydrothiopyran-3-yl | —$CH_2CH_2$—CH=CH— | 5-Cl-thien-3-yl | 4.20(t, 2H), 6.00(dt, 1H), 6.33(d, 1H), 6.83(s, 1H), 7.03(s, 1H) |
| A.584 | $C_2H_5$ | Tetrahydropyran-3-yl | —$CH_2CH_2CH$=$CHCH_3$— | Thien-2-yl | 3.90(m, 2H), 6.90(m, 2H), 7.10(d, 1H) |
| A.585 | n-$C_3H_7$ | Tetrahydropyran-3-yl | —$CH_2CH_2CH$=$CHCH_3$— | Thien-2-yl | 3.90(m, 2H), 6.90(m, 2H), 7.10(d, 1H) |
| A.586 | $C_2H_5$ | Tetrahydropyran-4-yl | —$CH_2CH_2CH$=$CHCH_3$— | Thien-2-yl | |
| A.587 | n-$C_3H_7$ | Tetrahydropyran-4-yl | —$CH_2CH_2CH$=$CHCH_3$— | Thien-2-yl | |
| A.588 | $C_2H_5$ | Tetrahydrothiopyran-3-yl | —$CH_2CH_2CH$=$CHCH_3$— | Thien-3-yl | 6.90(m, 2H), 7.10(d, 1H) |
| A.589 | n-$C_3H_7$ | Tetrahydrothiopyran-3-yl | —$CH_2CH_2CH$=$CHCH_3$— | Thien-3-yl | 6.90(m, 2H), 7.10(d, 1H) |
| A.590 | $C_2H_5$ | Tetrahydropyran-3-yl | —$(CH_2)_5$— | Furan-2-yl | 5.93(m, 1H), 6.27(m, 1H), 7.27(m, 1H) |
| A.591 | n-$C_3H_7$ | Tetrahydropyran-3-yl | —$(CH_2)_5$— | Furan-2-yl | 5.93(m, 1H), 6.27(m, 1H), 7.27(m, 1H) |
| A.592 | $C_2H_5$ | Tetrahydropyran-4-yl | —$(CH_2)_5$— | Furan-2-yl | 5.90(m, 1H), 6.24(m, 1H), 7.24(m, 1H) |
| A.593 | n-$C_3H_7$ | Tetrahydropyran-4-yl | —$(CH_2)_5$— | Furan-2-yl | 50–53 |
| A.594 | $C_2H_5$ | Tetrahydrothiopyran-3-yl | —$(CH_2)_5$— | Furan-2-yl | 5.93(m, 1H), 6.27(m, 1H), 7.27(m, 1H) |
| A.595 | n-$C_3H_7$ | Tetrahydrothiopyran-3-yl | —$(CH_2)_5$— | Furan-2-yl | 5.93(m, 1H), 6.27(m, 1H), 7.27(m, 1H) |
| A.596 | $C_2H_5$ | Tetrahydropyran-3-yl | —$(CH_2)_5$— | Thien-2-yl | 43–45 |
| A.597 | n-$C_3H_7$ | Tetrahydropyran-3-yl | —$(CH_2)_5$— | Thien-2-yl | 73–75 |
| A.598 | $C_2H_5$ | Tetrahydropyran-4-yl | —$(CH_2)_5$— | Thien-2-yl | 91–93 |
| A.599 | n-$C_3H_7$ | Tetrahydropyran-4-yl | —$(CH_2)_5$— | Thien-2-yl | 74–75 |
| A.600 | $C_2H_5$ | Tetrahydrothiopyran-3-yl | —$(CH_2)_5$— | Thien-2-yl | 4.07(t, 2H), 6.80(m, 1H), 6.90(m, 1H), 7.10(m, 1H) |
| A.601 | n-$C_3H_7$ | Tetrahydrothiopyran-3-yl | —$(CH_2)_5$— | Thien-2-yl | 4.07(t, 2H), 6.80(m, 1H), 6.90(m, 1H), 7.10(m, 1H) |
| A.602 | $C_2H_5$ | Tetrahydropyran-3-yl | —$(CH_2)_5$— | 1-$CH_3$-pyrrol-2-yl | 3.90(m, 2H), 4.12(t, 2H), 5.90(m, 1H), 6.06(m, 1H), 6.53(m, 1H) |
| A.603 | n-$C_3H_7$ | Tetrahydropyran-3-yl | —$(CH_2)_5$— | 1-$CH_3$-pyrrol-2-yl | 3.90(m, 2H), 4.12(t, 2H), |

TABLE 7-continued

[Structure: cyclohexenone with OH, =NO—W—R^f, R^a, R^c substituents; (R^b, R^d, R^e = H)]

| No. | R^a | R^c | W | R^f | Phys. data NMR data in ppm Mp. in °C. |
|---|---|---|---|---|---|
| A.604 | C₂H₅ | Tetrahydropyran-4-yl | —(CH₂)₅— | 1-CH₃-pyrrol-2-yl | 5.90(m, 1H), 6.06(m, 1H), 6.53(m, 1H) 4.00(m, 2H), 4.12(t, 2H), 5.90(m, 1H), 6.06(m, 1H), 6.53(m, 1H) |
| A.605 | n-C₃H₇ | Tetrahydropyran-4-yl | —(CH₂)₅— | 1-CH₃-pyrrol-2-yl | 4.00(m, 2H), 4.12(t, 2H), 5.90(m, 1H), 6.06(m, 1H), 6.53(m, 1H) |
| A.606 | C₂H₅ | Tetrahydrothiopyran-3-yl | —(CH₂)₅— | 1-CH₃-pyrrol-2-yl | 4.12(t, 2H), 5.90(m, 1H), 6.06(m, 1H), 6.53(m, 1H) |
| A.607 | n-C₃H₇ | Tetrahydrothiopyran-3-yl | —(CH₂)₅— | 1-CH₃-pyrrol-2-yl | 4.12(t, 2H), 5.90(m, 1H), 6.06(m, 1H), 6.53(m, 1H) |
| A.608 | C₂H₅ | Tetrahydropyran-3-yl | —(CH₂)₆— | Furan-2-yl | 5.90(m, 1H), 6.27(m, 1H), 7.27(m, 1H) |
| A.609 | n-C₃H₇ | Tetrahydropyran-3-yl | —(CH₂)₆— | Furan-2-yl | 5.90(m, 1H), 6.27(m, 1H), 7.27(m, 1H) |
| A.610 | C₂H₅ | Tetrahydropyran-4-yl | —(CH₂)₆— | Furan-2-yl | 5.93(m, 1H), 6.27(m, 1H), 7.27(m, 1H) |
| A.611 | n-C₃H₇ | Tetrahydropyran-4-yl | —(CH₂)₆— | Furan-2-yl | 5.93(m, 1H), 6.27(m, 1H), 7.27(m, 1H) |
| A.612 | C₂H₅ | Tetrahydrothiopyran-3-yl | —(CH₂)₆— | Furan-2-yl | 5.93(m, 1H), 6.27(m, 1H), 7.27(m, 1H) |
| A.613 | n-C₃H₇ | Tetrahydrothiopyran-3-yl | —(CH₂)₆— | Furan-2-yl | 5.93(m, 1H), 6.27(m, 1H), 7.27(m, 1H) |
| A.614 | C₂H₅ | Tetrahydropyran-3-yl | —(CH₂)₆— | Thien-2-yl | 6.77(m, 1H), 6.90(m, 1H), 7.10(m, 1H) |
| A.615 | n-C₃H₇ | Tetrahydropyran-3-yl | —(CH₂)₆— | Thien-2-yl | 6.77(m, 1H), 6.90(m, 1H), 7.10(m, 1H) |
| A.616 | C₂H₅ | Tetrahydropyran-4-yl | —(CH₂)₆— | Thien-2-yl | 50–52 |
| A.617 | n-C₃H₇ | Tetrahydropyran-4-yl | —(CH₂)₆— | Thien-2-yl | 6.80(m, 1H), 6.90(m, 1H), 7.10(m, 1H) |
| A.618 | C₂H₅ | Tetrahydrothiopyran-3-yl | —(CH₂)₆— | Thien-2-yl | 6.80(m, 1H), 6.90(m, 1H), 7.10(m, 1H) |
| A.619 | n-C₃H₇ | Tetrahydrothiopyran-3-yl | —(CH₂)₆— | Thien-2-yl | 6.80(m, 1H), 6.90(m, 1H), 7.10(m, 1H) |
| A.620 | C₂H₅ | Tetrahydropyran-3-yl | —(CH₂)₆— | 1-CH₃-pyrrol-2-yl | 5.90(m, 1H), 6.06(m, 1H), 6.53(m, 1H) |
| A.621 | n-C₃H₇ | Tetrahydropyran-3-yl | —(CH₂)₆— | 1-CH₃-pyrrol-2-yl | 5.90(m, 1H), 6.06(m, 1H), 6.53(m, 1H) |
| A.622 | C₂H₅ | Tetrahydropyran-4-yl | —(CH₂)₆— | 1-CH₃-pyrrol-2-yl | 5.87(m, 1H), 6.06(m, 1H), 6.53(m, 1H) |
| A.623 | n-C₃H₇ | Tetrahydropyran-4-yl | —(CH₂)₆— | 1-CH₃-pyrrol-2-yl | 5.87(m, 1H), 6.06(m, 1H), 6.53(m, 1H) |
| A.624 | C₂H₅ | Tetrahydrothiopyran-3-yl | —(CH₂)₆— | 1-CH₃-pyrrol-2-yl | 5.90(m, 1H), 6.06(m, 1H), 6.50(m, 1H) |
| A.625 | n-C₃H₇ | Tetrahydrothiopyran-3-yl | —(CH₂)₆— | 1-CH₃-pyrrol-2-yl | 5.90(m, 1H), 6.06(m, 1H), 6.50(m, 1H) |
| A.626 | C₂H₅ | Tetrahydropyran-3-yl | —CH₂CH₂—O— | Phenyl | 42–45 |
| A.627 | n-C₃H₇ | Tetrahydropyran-3-yl | —CH₂CH₂—O— | Phenyl | 3.90(m, 2H), 4.20(t, 2H), 4.40(m, 2H), (m, 3H), 7.13–7.37(m, 2H) |
| A.628 | C₂H₅ | Tetrahydropyran-4-yl | —CH₂CH₂—O— | Phenyl | 106–107 |
| A.629 | n-C₃H₇ | Tetrahydropyran-4-yl | —CH₂CH₂—O— | Phenyl | 72–73 |
| A.630 | C₂H₅ | Tetrahydrothiopyran-3-yl | —CH₂CH₂—O— | Phenyl | 52–55 |
| A.631 | n-C₃H₇ | Tetrahydrothiopyran-3-yl | —CH₂CH₂—O— | Phenyl | 92 |
| A.632 | C₂H₅ | Tetrahydropyran-3-yl | —CH₂CH₂—O— | 2-F-phenyl | 76–78 |
| A.633 | n-C₃H₇ | Tetrahydropyran-3-yl | —CH₂CH₂—O— | 2-F-phenyl | 72–77 |
| A.634 | C₂H₅ | Tetrahydropyran-4-yl | —CH₂CH₂—O— | 2-F-phenyl | 121–125 |
| A.635 | n-C₃H₇ | Tetrahydropyran-4-yl | —CH₂CH₂—O— | 2-F-phenyl | 103–107 |
| A.636 | C₂H₅ | Tetrahydrothiopyran-3-yl | —CH₂CH₂—O— | 2-F-phenyl | 82–86 |
| A.637 | n-C₃H₇ | Tetrahydrothiopyran-3-yl | —CH₂CH₂—O— | 2-F-phenyl | 81–85 |
| A.638 | C₂H₅ | Tetrahydropyran-3-yl | —CH₂CH₂—O— | 3-F-phenyl | 62–68 |
| A.639 | n-C₃H₇ | Tetrahydropyran-3-yl | —CH₂CH₂—O— | 3-F-phenyl | 3.90(m, 2H), 4.20(t, 2H), 4.40(m, 2H), 7.25(m, 1H) |
| A.640 | C₂H₅ | Tetrahydropyran-4-yl | —CH₂CH₂—O— | 3-F-phenyl | 103–109 |
| A.641 | n-C₃H₇ | Tetrahydropyran-4-yl | —CH₂CH₂—O— | 3-F-phenyl | 73–79 |

TABLE 7-continued

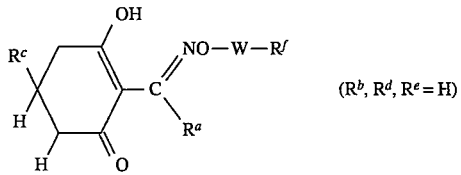

($R^b$, $R^d$, $R^e$ = H)

| No. | $R^a$ | $R^c$ | W | $R^f$ | Phys. data<br>NMR data in ppm<br>Mp. in °C. |
|---|---|---|---|---|---|
| A.642 | $C_2H_5$ | Tetrahydrothiopyran-3-yl | —$CH_2CH_2$—O— | 3-F-phenyl | 4.20(t, 2H), 4.40(m, 2H),<br>6.70(m, 3H), 7.25(m, 1H) |
| A.643 | n-$C_3H_7$ | Tetrahydrothiopyran-3-yl | —$CH_2CH_2$—O— | 3-F-phenyl | |
| A.644 | $C_2H_5$ | Tetrahydropyran-3-yl | —$CH_2CH_2$—O— | 4-F-phenyl | 64–67 |
| A.645 | n-$C_3H_7$ | Tetrahydropyran-3-yl | —$CH_2CH_2$—O— | 4-F-phenyl | 70–72 |
| A.646 | $C_2H_5$ | Tetrahydropyran-4-yl | —$CH_2CH_2$—O— | 4-F-phenyl | 101–103 |
| A.647 | n-$C_3H_7$ | Tetrahydropyran-4-yl | —$CH_2CH_2$—O— | 4-F-phenyl | 107–109 |
| A.648 | $C_2H_5$ | Tetrahydrothiopyran-3-yl | —$CH_2CH_2$—O— | 4-F-phenyl | 105–108 |
| A.649 | n-$C_3H_7$ | Tetrahydrothiopyran-3-yl | —$CH_2CH_2$—O— | 4-F-phenyl | 82–84 |
| A.650 | $C_2H_5$ | Tetrahydropyran-3-yl | —$CH_2CH_2$—O— | 2-Cl-phenyl | 74–80 |
| A.651 | n-$C_3H_7$ | Tetrahydropyran-3-yl | —$CH_2CH_2$—O— | 2-Cl-phenyl | 67–71 |
| A.652 | $C_2H_5$ | Tetrahydropyran-4-yl | —$CH_2CH_2$—O— | 2-Cl-phenyl | 4.00(m, 2H), 4.27(t, 2H),<br>4.47(m, 2H), 7.20(t, 1H),<br>7.37(d, 1H) |
| A.653 | n-$C_3H_7$ | Tetrahydropyran-4-yl | —$CH_2CH_2$—O— | 2-Cl-phenyl | 68–72 |
| A.654 | $C_2H_5$ | Tetrahydrothiopyran-3-yl | —$CH_2CH_2$—O— | 2-Cl-phenyl | 74–78 |
| A.655 | n-$C_3H_7$ | Tetrahydrothiopyran-3-yl | —$CH_2CH_2$—O— | 2-Cl-phenyl | 72–78 |
| A.656 | $C_2H_5$ | Tetrahydropyran-3-yl | —$CH_2CH_2$—O— | 3-Cl-phenyl | |
| A.657 | n-$C_3H_7$ | Tetrahydropyran-3-yl | —$CH_2CH_2$—O— | 3-Cl-phenyl | |
| A.658 | $C_2H_5$ | Tetrahydropyran-4-yl | —$CH_2CH_2$—O— | 3-Cl-phenyl | |
| A.659 | n-$C_3H_7$ | Tetrahydropyran-4-yl | —$CH_2CH_2$—O— | 3-Cl-phenyl | |
| A.660 | $C_2H_5$ | Tetrahydrothiopyran-3-yl | —$CH_2CH_2$—O— | 3-Cl-phenyl | |
| A.661 | n-$C_3H_7$ | Tetrahydrothiopyran-3-yl | —$CH_2CH_2$—O— | 3-Cl-phenyl | |
| A.662 | $C_2H_5$ | Tetrahydropyran-3-yl | —$CH_2CH_2$—O— | 4-Cl-phenyl | 3.93(m, 2H), 4.20(t, 2H),<br>4.43(m, 2H), 6.90(m, 2H),<br>7.25(m, 2H) |
| A.663 | n-$C_3H_7$ | Tetrahydropyran-3-yl | —$CH_2CH_2$—O— | 4-Cl-phenyl | 3.93(m, 2H), 4.20(t, 2H),<br>4.43(m, 2H), 6.90(m, 2H),<br>7.25(m, 2H) |
| A.664 | $C_2H_5$ | Tetrahydropyran-4-yl | —$CH_2CH_2$—O— | 4-Cl-phenyl | 116–118 |
| A.665 | n-$C_3H_7$ | Tetrahydropyran-4-yl | —$CH_2CH_2$—O— | 4-Cl-phenyl | 104–106 |
| A.666 | $C_2H_5$ | Tetrahydrothiopyran-3-yl | —$CH_2CH_2$—O— | 4-Cl-phenyl | 74–77 |
| A.667 | n-$C_3H_7$ | Tetrahydrothiopyran-3-yl | —$CH_2CH_2$—O— | 4-Cl-phenyl | 86–88 |
| A.668 | $C_2H_5$ | Tetrahydropyran-3-yl | —$CH_2CH_2$—O— | 2-$CF_3$-phenyl | |
| A.669 | n-$C_3H_7$ | Tetrahydropyran-3-yl | —$CH_2CH_2$—O— | 2-$CF_3$-phenyl | |
| A.670 | $C_2H_5$ | Tetrahydropyran-4-yl | —$CH_2CH_2$—O— | 2-$CF_3$-phenyl | |
| A.671 | n-$C_3H_7$ | Tetrahydropyran-4-yl | —$CH_2CH_2$—O— | 2-$CF_3$-phenyl | |
| A.672 | $C_2H_5$ | Tetrahydrothiopyran-3-yl | —$CH_2CH_2$—O— | 2-$CF_3$-phenyl | |
| A.673 | n-$C_3H_7$ | Tetrahydrothiopyran-3-yl | —$CH_2CH_2$—O— | 2-$CF_3$-phenyl | |
| A.674 | $C_2H_5$ | Tetrahydropyran-3-yl | —$CH_2CH_2$—O— | 3-$CF_3$-phenyl | |
| A.675 | n-$C_3H_7$ | Tetrahydropyran-3-yl | —$CH_2CH_2$—O— | 3-$CF_3$-phenyl | |
| A.676 | $C_2H_5$ | Tetrahydropyran-4-yl | —$CH_2CH_2$—O— | 3-$CF_3$-phenyl | |
| A.677 | n-$C_3H_7$ | Tetrahydropyran-4-yl | —$CH_2CH_2$—O— | 3-$CF_3$-phenyl | |
| A.678 | $C_2H_5$ | Tetrahydrothiopyran-3-yl | —$CH_2CH_2$—O— | 3-$CF_3$-phenyl | |
| A.679 | n-$C_3H_7$ | Tetrahydrothiopyran-3-yl | —$CH_2CH_2$—O— | 3-$CF_3$-phenyl | |
| A.680 | $C_2H_5$ | Tetrahydropyran-3-yl | —$CH_2CH_2$—O— | 4-$CF_3$-phenyl | 72–77 |
| A.681 | n-$C_3H_7$ | Tetrahydropyran-3-yl | —$CH_2CH_2$—O— | 4-$CF_3$-phenyl | 3.90(m, 2H), 4.27(t, 2H),<br>4.47(m, 2H), 7.00(d, 2H),<br>7.55(d, 2H) |
| A.682 | $C_2H_5$ | Tetrahydropyran-4-yl | —$CH_2CH_2$—O— | 4-$CF_3$-phenyl | |
| A.683 | n-$C_3H_7$ | Tetrahydropyran-4-yl | —$CH_2CH_2$—O— | 4-$CF_3$-phenyl | 90–94 |
| A.684 | $C_2H_5$ | Tetrahydrothiopyran-3-yl | —$CH_2CH_2$—O— | 4-$CF_3$-phenyl | 73–79 |
| A.685 | n-$C_3H_7$ | Tetrahydrothiopyran-3-yl | —$CH_2CH_2$—O— | 4-$CF_3$-phenyl | 4.27(t, 2H), 4.47(m, 2H),<br>7.00(d, 2H), 7.55(d, 2H) |
| A.686 | $C_2H_5$ | Tetrahydropyran-3-yl | —$CH_2CH_2$—O— | 2,4-$Cl_2$-phenyl | 73–75 |
| A.687 | n-$C_3H_7$ | Tetrahydropyran-3-yl | —$CH_2CH_2$—O— | 2,4-$Cl_2$-phenyl | 69–73 |
| A.688 | $C_2H_5$ | Tetrahydropyran-4-yl | —$CH_2CH_2$—O— | 2,4-$Cl_2$-phenyl | 4.00(m, 2H), 4.25(t, 2H),<br>4.45(t, 2H), 6.87(d, 1H),<br>7.17(d, 1H), 7.37(d, 1H) |
| A.689 | n-$C_3H_7$ | Tetrahydropyran-4-yl | —$CH_2CH_2$—O— | 2,4-$Cl_2$-phenyl | 4.00(m, 2H), 4.25(t, 2H),<br>4.45(t, 2H), 6.87(d, 1H),<br>7.17(d, 1H), 7.37(d, 1H) |
| A.690 | $C_2H_5$ | Tetrahydrothiopyran-3-yl | —$CH_2CH_2$—O— | 2,4-$Cl_2$-phenyl | 4.25(t, 2H), 4.45(t, 2H),<br>6.87(d, 1H), 7.17(d, 1H),<br>7.37(d, 1H) |
| A.691 | n-$C_3H_7$ | Tetrahydrothiopyran-3-yl | —$CH_2CH_2$—O— | 2,4-$Cl_2$-phenyl | 4.25(t, 2H), 4.45(t, 2H), |

TABLE 7-continued $$\text{structure with } R^c, R^a, \text{OH, NO—W—R}^f, \text{with } (R^b, R^d, R^e = H)$$

| No. | $R^a$ | $R^c$ | W | $R^f$ | Phys. data NMR data in ppm Mp. in °C. |
|---|---|---|---|---|---|
| | | | | | 6.87(d, 1H), 7.17(d, 1H), 7.37(d, 1H) |
| A.692 | $C_2H_5$ | Tetrahydropyran-3-yl | —$CH_2CH_2$—O— | 2,4,6-$Cl_3$-phenyl | 90–93 |
| A.693 | n-$C_3H_7$ | Tetrahydropyran-3-yl | —$CH_2CH_2$—O— | 2,4,6-$Cl_3$-phenyl | 83–87 |
| A.694 | $C_2H_5$ | Tetrahydropyran-4-yl | —$CH_2CH_2$—O— | 2,4,6-$Cl_3$-phenyl | 79–82 |
| A.695 | n-$C_3H_7$ | Tetrahydropyran-4-yl | —$CH_2CH_2$—O— | 2,4,6-$Cl_3$-phenyl | 4.00(m, 2H), 4.27(t, 2H), 4.45(m, 2H), 7.32(s, 2H) |
| A.696 | $C_2H_5$ | Tetrahydrothiopyran-3-yl | —$CH_2CH_2$—O— | 2,4,6-$Cl_3$-phenyl | 105–108 |
| A.697 | n-$C_3H_7$ | Tetrahydrothiopyran-3-yl | —$CH_2CH_2$—O— | 2,4,6-$Cl_3$-phenyl | 4.27(t, 2H), 4.45(m, 2H), 7.82(s, 2H) |
| A.698 | $C_2H_5$ | Tetrahydropyran-3-yl | —$CH_2CH_2$—O— | 4-$NO_2$-phenyl | 3.90(m, 2H), 4.32(m, 2H), 4.50(m, 2H), 7.00(d, 2H), 8.20(d, 2H) |
| A.699 | n-$C_3H_7$ | Tetrahydropyran-3-yl | —$CH_2CH_2$—O— | 4-$NO_2$-phenyl | 3.90(m, 2H), 4.32(m, 2H), 4.50(m, 2H), 7.00(d, 2H), 8.20(d, 2H) |
| A.700 | $C_2H_5$ | Tetrahydropyran-4-yl | —$CH_2CH_2$—O— | 4-$NO_2$-phenyl | 126–129 |
| A.701 | n-$C_3H_7$ | Tetrahydropyran-4-yl | —$CH_2CH_2$—O— | 4-$NO_2$-phenyl | 138–141 |
| A.702 | $C_2H_5$ | Tetrahydrothiopyran-3-yl | —$CH_2CH_2$—O— | 4-$NO_2$-phenyl | 4.32(m, 2H), 4.50(m, 2H), 7.00(d, 2H), 8.20(d, 2H) |
| A.703 | n-$C_3H_7$ | Tetrahydrothiopyran-3-yl | —$CH_2CH_2$—O— | 4-$NO_2$-phenyl | 4.32(m, 2H), 4.50(m, 2H), 7.00(d, 2H), 8.20(d, 2H) |
| A.704 | $C_2H_5$ | Tetrahydropyran-3-yl | —$CH_2CH(CH_3)$—O— | Phenyl | |
| A.705 | n-$C_3H_7$ | Tetrahydropyran-3-yl | —$CH_2CH(CH_3)$—O— | Phenyl | |
| A.706 | $C_2H_5$ | Tetrahydropyran-4-yl | —$CH_2CH(CH_3)$—O— | Phenyl | |
| A.707 | n-$C_3H_7$ | Tetrahydropyran-4-yl | —$CH_2CH(CH_3)$—O— | Phenyl | |
| A.708 | $C_2H_5$ | Tetrahydrothiopyran-3-yl | —$CH_2CH(CH_3)$—O— | Phenyl | |
| A.709 | n-$C_3H_7$ | Tetrahydrothiopyran-3-yl | —$CH_2CH(CH_3)$—O— | Phenyl | |
| A.710 | $C_2H_5$ | Tetrahydropyran-3-yl | —$CH_2CH(CH_3)$—O— | 4-F-phenyl | |
| A.711 | n-$C_3H_7$ | Tetrahydropyran-3-yl | —$CH_2CH(CH_3)$—O— | 4-F-phenyl | |
| A.712 | $C_2H_5$ | Tetrahydropyran-4-yl | —$CH_2CH(CH_3)$—O— | 4-F-phenyl | |
| A.713 | n-$C_3H_7$ | Tetrahydropyran-4-yl | —$CH_2CH(CH_3)$—O— | 4-F-phenyl | |
| A.714 | $C_2H_5$ | Tetrahydrothiopyran-3-yl | —$CH_2CH(CH_3)$—O— | 4-F-phenyl | |
| A.715 | n-$C_3H_7$ | Tetrahydrothiopyran-3-yl | —$CH_2CH(CH_3)$—O— | 4-F-phenyl | |
| A.716 | $C_2H_5$ | Tetrahydropyran-3-yl | —$CH_2CH(CH_3)$—O— | 4-Cl-phenyl | |
| A.717 | n-$C_3H_7$ | Tetrahydropyran-3-yl | —$CH_2CH(CH_3)$—O— | 4-Cl-phenyl | |
| A.718 | $C_2H_5$ | Tetrahydropyran-4-yl | —$CH_2CH(CH_3)$—O— | 4-Cl-phenyl | 1.35(m, 3H), 4.05–4.30(m, 2H) 4.60(m, 1H), 6.80–7.40(m, 4H) |
| A.719 | n-$C_3H_7$ | Tetrahydropyran-4-yl | —$CH_2CH(CH_3)$—O— | 4-Cl-phenyl | 1.35(m, 3H), 4.05–4.30(m, 2H) 4.60(m, 1H), 6.80–7.40(m, 4H) |
| A.720 | $C_2H_5$ | Tetrahydrothiopyran-3-yl | —$CH_2CH(CH_3)$—O— | 4-Cl-phenyl | 1.35(m, 3H), 4.05–4.25(m, 2H) 4.60(m, 1H), 6.80–7.40(m, 4H) |
| A.721 | n-$C_3H_7$ | Tetrahydrothiopyran-3-yl | —$CH_2CH(CH_3)$—O— | 4-Cl-phenyl | 1.35(m, 3H), 4.05–4.30(m, 2H) 4.60(m, 1H), 6.80–7.40(m, 4H) |
| A.722 | $C_2H_5$ | Tetrahydropyran-3-yl | —$CH_2CH_2$—S— | Phenyl | 3.90(m, 2H), 4.23(t, 2H), 7.17–7.43(m, 5H) |
| A.723 | n-$C_3H_7$ | Tetrahydropyran-3-yl | —$CH_2CH_2$—S— | Phenyl | 65 |
| A.724 | $C_2H_5$ | Tetrahydropyran-4-yl | —$CH_2CH_2$—S— | Phenyl | 3.97(m, 2H), 4.23(t, 2H), 7.17–7.43(m, 5H) |
| A.725 | n-$C_3H_7$ | Tetrahydropyran-4-yl | —$CH_2CH_2$—S— | Phenyl | 3.97(m, 2H), 4.23(t, 2H), 7.17–7.43(m, 5H) |
| A.726 | $C_2H_5$ | Tetrahydrothiopyran-3-yl | —$CH_2CH_2$—S— | Phenyl | 4.23(t, 2H), 7.17–7.43(m, 5H) |
| A.727 | n-$C_3H_7$ | Tetrahydrothiopyran-3-yl | —$CH_2CH_2$—S— | Phenyl | 4.23(t, 2H), 7.17–7.43(m, 5H) |
| A.728 | $C_2H_5$ | Tetrahydropyran-3-yl | —$CH_2CH_2$—S— | 4-F-phenyl | 3.90(m, 2H), 4.17(t, 2H), 7.00(m, 2H), 7.40(m, 2H) |
| A.729 | n-$C_3H_7$ | Tetrahydropyran-3-yl | —$CH_2CH_2$—S— | 4-F-phenyl | 3.90(m, 2H), 4.17(t, 2H), 7.00(m, 2H), 7.40(m, 2H) |
| A.730 | $C_2H_5$ | Tetrahydropyran-4-yl | —$CH_2CH_2$—S— | 4-F-phenyl | 4.00(m, 2H), 4.17(t, 2H), 7.00(m, 2H), 7.40(m, 2H) |
| A.731 | n-$C_3H_7$ | Tetrahydropyran-4-yl | —$CH_2CH_2$—S— | 4-F-phenyl | 4.00(m, 2H), 4.17(t, 2H), 7.00(m, 2H), 7.40(m, 2H) |
| A.732 | $C_2H_5$ | Tetrahydrothiopyran-3-yl | —$CH_2CH_2$—S— | 4-F-phenyl | 4.17(t, 2H), 7.00(m, 2H), 7.40(m, 2H), |
| A.733 | n-$C_3H_7$ | Tetrahydrothiopyran-3-yl | —$CH_2CH_2$—S— | 4-F-phenyl | 4.17(t, 2H), 7.00(m, 2H), 7.40(m, 2H), |
| A.734 | $C_2H_5$ | Tetrahydropyran-3-yl | —$CH_2CH_2$—S— | 4-Cl-phenyl | 71–75 |

TABLE 7-continued

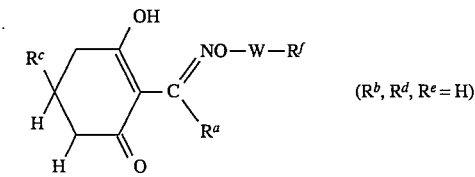

(R$^b$, R$^d$, R$^e$ = H)

| No. | R$^a$ | R$^c$ | W | R$^f$ | Phys. data NMR data in ppm Mp. in °C. |
|---|---|---|---|---|---|
| A.735 | n-C$_3$H$_7$ | Tetrahydropyran-3-yl | —CH$_2$CH$_2$—S— | 4-Cl-phenyl | 63–65 |
| A.736 | C$_2$H$_5$ | Tetrahydropyran-4-yl | —CH$_2$CH$_2$—S— | 4-Cl-phenyl | 4.00(m, 2H), 4.20(t, 2H), 7.30(m, 4H) |
| A.737 | n-C$_3$H$_7$ | Tetrahydropyran-4-yl | —CH$_2$CH$_2$—S— | 4-Cl-phenyl | 4.00(m, 2H), 4.20(t, 2H), 7.30(m, 4H) |
| A.738 | C$_2$H$_5$ | Tetrahydrothiopyran-3-yl | —CH$_2$CH$_2$—S— | 4-Cl-phenyl | 4.20(t, 2H), 7.30(m, 4H) |
| A.739 | n-C$_3$H$_7$ | Tetrahydrothiopyran-3-yl | —CH$_2$CH$_2$—S— | 4-Cl-phenyl | 4.20(t, 2H), 7.30(m, 4H) |
| A.740 | C$_2$H$_5$ | Tetrahydropyran-3-yl | —CH$_2$CH$_2$—S— | 2-Cl-phenyl | 3.90(m, 2H), 4.25(t, 2H), 7.10–7.50(m, 4H) |
| A.741 | n-C$_3$H$_7$ | Tetrahydropyran-3-yl | —CH$_2$CH$_2$—S— | 2-Cl-phenyl | 3.90(m, 2H), 4.25(t, 2H), 7.10–7.50(m, 4H) |
| A.742 | C$_2$H$_5$ | Tetrahydropyran-4-yl | —CH$_2$CH$_2$—S— | 2-Cl-phenyl | 4.00(m, 2H), 4.25(t, 2H), 7.10–7.50(m, 4H) |
| A.743 | n-C$_3$H$_7$ | Tetrahydropyran-4-yl | —CH$_2$CH$_2$—S— | 2-Cl-phenyl | 4.00(m, 2H), 4.25(t, 2H), 7.10–7.50(m, 4H) |
| A.744 | C$_2$H$_5$ | Tetrahydrothiopyran-3-yl | —CH$_2$CH$_2$—S— | 2-Cl-phenyl | 4.25(t, 2H) 7.10–7.50(m, 4H) |
| A.745 | n-C$_3$H$_7$ | Tetrahydrothiopyran-3-yl | —CH$_2$CH$_2$—S— | 2-Cl-phenyl | 4.25(t, 2H) 7.10–7.50(m, 4H) |
| A.746 | C$_2$H$_5$ | Tetrahydropyran-3-yl | —CH$_2$CH$_2$—S— | 2,6-Cl$_2$-phenyl | 3.90(m, 2H) 4.20(t, 2H), 7.20(t, 1H), 7.40(d, 2H) |
| A.747 | n-C$_3$H$_7$ | Tetrahydropyran-3-yl | —CH$_2$CH$_2$—S— | 2,6-Cl$_2$-phenyl | 3.90(m, 2H) 4.20(t, 2H), 7.20(t, 1H), 7.40(d, 2H) |
| A.748 | C$_2$H$_5$ | Tetrahydropyran-4-yl | —CH$_2$CH$_2$—S— | 2,6-Cl$_2$-phenyl | 61–64 |
| A.749 | n-C$_3$H$_7$ | Tetrahydropyran-4-yl | —CH$_2$CH$_2$—S— | 2,6-Cl$_2$-phenyl | 4.00(m, 2H) 4.20(t, 2H), 7.20(t, 1H), 7.40(d, 2H) |
| A.750 | C$_2$H$_5$ | Tetrahydrothiopyran-3-yl | —CH$_2$CH$_2$—S— | 2,6-Cl$_2$-phenyl | 4.20(t, 2H) 7.20(t, 2H), 7.40(d, 2H) |
| A.751 | n-C$_3$H$_7$ | Tetrahydrothiopyran-3-yl | —CH$_2$CH$_2$—S— | 2,6-Cl$_2$-phenyl | 4.20(t, 2H) 7.20(t, 2H), 7.40(d, 2H) |
| A.752 | C$_2$H$_5$ | Tetrahydropyran-3-yl | —(CH$_2$)$_3$—O— | Phenyl | 3.90(m, 2H), 4.03(t, 2H), 4.23(t, 2H), 6.90(m, 3H), 7.27(m, 2H) |
| A.753 | n-C$_3$H$_7$ | Tetrahydropyran-3-yl | —(CH$_2$)$_3$—O— | Phenyl | 3.90(m, 2H), 4.03(t, 2H), 4.23(t, 2H), 6.90(m, 3H), 7.27(m, 2H) |
| A.754 | C$_2$H$_5$ | Tetrahydropyran-4-yl | —(CH$_2$)$_3$—O— | Phenyl | 3.97(m, 2H), 4.03(t, 2H), 4.23(t, 2H), 6.90(m, 3H), 7.27(m, 2H) |
| A.755 | n-C$_3$H$_7$ | Tetrahydropyran-4-yl | —(CH$_2$)$_3$—O— | Phenyl | 3.97(m, 2H), 4.03(t, 2H), 4.23(t, 2H), 6.90(m, 3H), 7.27(m, 2H) |
| A.756 | C$_2$H$_5$ | Tetrahydrothiopyran-3-yl | —(CH$_2$)$_3$—O— | Phenyl | 4.03(t, 2H), 4.23(t, 2H), 6.90(m, 3H), 7.27(m, 2H) |
| A.757 | n-C$_3$H$_7$ | Tetrahydrothiopyran-3-yl | —(CH$_2$)$_3$—O— | Phenyl | 4.03(t, 2H), 4.23(t, 2H), 6.90(m, 3H), 7.27(m, 2H) |
| A.758 | C$_2$H$_5$ | Tetrahydropyran-3-yl | —(CH$_2$)$_3$—O— | 2-F-phenyl | 3.90(m, 2H), 4.10(t, 2H), 4.27(t, 2H), 6.80–7.15(m, 4H) |
| A.759 | n-C$_3$H$_7$ | Tetrahydropyran-3-yl | —(CH$_2$)$_3$—O— | 2-F-phenyl | 3.90(m, 2H), 4.10(t, 2H), 4.27(t, 2H), 6.80–7.15(m, 4H) |
| A.760 | C$_2$H$_5$ | Tetrahydropyran-4-yl | —(CH$_2$)$_3$—O— | 2-F-phenyl | 4.00(m, 2H), 4.10(t, 2H), 4.27(t, 2H), 6.80–7.15(m, 4H) |
| A.761 | n-C$_3$H$_7$ | Tetrahydropyran-4-yl | —(CH$_2$)$_3$—O— | 2-F-phenyl | 76–80 |
| A.762 | C$_2$H$_5$ | Tetrahydrothiopyran-3-yl | —(CH$_2$)$_3$—O— | 2-F-phenyl | 4.10(t, 2H), 4.27(t, 2H), 6.80–7.15(m, 4H), |
| A.763 | n-C$_3$H$_7$ | Tetrahydrothiopyran-3-yl | —(CH$_2$)$_3$—O— | 2-F-phenyl | 4.10(t, 2H), 4.27(t, 2H), 6.80–7.15(m, 4H), |
| A.764 | C$_2$H$_5$ | Tetrahydropyran-3-yl | —(CH$_2$)$_3$—O— | 3-F-phenyl | 3.90(m, 2H), 4.05(t, 2H), 4.27(t, 2H), 6.67(m, 3H), 7.23(m, 1H) |
| A.765 | n-C$_3$H$_7$ | Tetrahydropyran-3-yl | —(CH$_2$)$_3$—O— | 3-F-phenyl | 3.90(m, 2H), 4.05(t, 2H), 4.27(t, 2H), 6.67(m, 3H), 7.23(m, 1H) |
| A.766 | C$_2$H$_5$ | Tetrahydropyran-4-yl | —(CH$_2$)$_3$—O— | 3-F-phenyl | 3.90–4.10(m, 4H), 4.27(t, 2H) 6.67(m, 3H), 7.23(m, 1H) |
| A.767 | n-C$_3$H$_7$ | Tetrahydropyran-4-yl | —(CH$_2$)$_3$—O— | 3-F-phenyl | 3.90–4.10(m, 4H), 4.27(t, 2H) 6.67(m, 3H), 7.23(m, 1H) |
| A.768 | C$_2$H$_5$ | Tetrahydrothiopyran-3-yl | —(CH$_2$)$_3$—O— | 3-F-phenyl | 4.05(t, 2H), 4.27(t, 2H), |

TABLE 7-continued

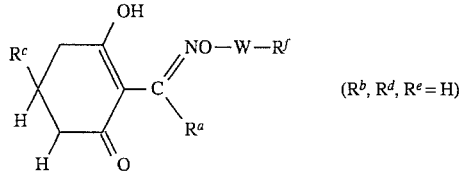

($R^b$, $R^d$, $R^e$ = H)

| No. | $R^a$ | $R^c$ | W | $R^f$ | Phys. data NMR data in ppm Mp. in °C. |
|---|---|---|---|---|---|
| A.769 | n-$C_3H_7$ | Tetrahydrothiopyran-3-yl | —$(CH_2)_3$—O— | 3-F-phenyl | 6.67(m, 3H), 7.23(m, 1H) 4.05(t, 2H), 4.27(t, 2H), 6.67(m, 3H), 7.23(m, 1H) |
| A.770 | $C_2H_5$ | Tetrahydropyran-3-yl | —$(CH_2)_3$—O— | 4-F-phenyl | 3.90(m, 2H), 4.03(t, 2H), 4.27(t, 2H), 6.90(m, 2H), 7.00(m, 2H) |
| A.771 | n-$C_3H_7$ | Tetrahydropyran-3-yl | —$(CH_2)_3$—O— | 4-F-phenyl | 3.90(m, 2H), 4.03(t, 2H), 4.27(t, 2H), 6.90(m, 2H), 7.00(m, 2H) |
| A.772 | $C_2H_5$ | Tetrahydropyran-4-yl | —$(CH_2)_3$—O— | 4-F-phenyl | 3.90–4.06(m, 4H), 4.23(t, 2H) 6.90(m, 2H), 7.00(m, 2H) |
| A.773 | n-$C_3H_7$ | Tetrahydropyran-4-yl | —$(CH_2)_3$—O— | 4-F-phenyl | 3.90–4.06(m, 4H), 4.28(t, 2H) 6.90(m, 2H), 7.00(m, 2H) |
| A.774 | $C_2H_5$ | Tetrahydrothiopyran-3-yl | —$(CH_2)_3$—O— | 4-F-phenyl | 4.03(t, 2H), 4.27(t, 2H), 6.90(m, 2H), 7.00(m, 2H) |
| A.775 | n-$C_3H_7$ | Tetrahydrothiopyran-3-yl | —$(CH_2)_3$—O— | 4-F-phenyl | 4.03(t, 2H), 4.27(t, 2H), 6.90(m, 2H), 7.00(m, 2H) |
| A.776 | $C_2H_5$ | Tetrahydropyran-3-yl | —$(CH_2)_3$—O— | 2-Cl-phenyl | |
| A.777 | n-$C_3H_7$ | Tetrahydropyran-3-yl | —$(CH_2)_3$—O— | 2-Cl-phenyl | |
| A.778 | $C_2H_5$ | Tetrahydropyran-4-yl | —$(CH_2)_3$—O— | 2-Cl-phenyl | |
| A.779 | n-$C_3H_7$ | Tetrahydropyran-4-yl | —$(CH_2)_3$—O— | 2-Cl-phenyl | |
| A.780 | $C_2H_5$ | Tetrahydrothiopyran-3-yl | —$(CH_2)_3$—O— | 2-Cl-phenyl | |
| A.781 | n-$C_3H_7$ | Tetrahydrothiopyran-3-yl | —$(CH_2)_3$—O— | 2-Cl-phenyl | |
| A.782 | $C_2H_5$ | Tetrahydropyran-3-yl | —$(CH_2)_3$—O— | 3-Cl-phenyl | 3.90(m, 2H), 4.06(t, 2H), 4.27(t, 2H), 6.77(m, 1H), 6.90(m, 2H), 7.17(m, 1H) |
| A.783 | n-$C_3H_7$ | Tetrahydropyran-3-yl | —$(CH_2)_3$—O— | 3-Cl-phenyl | 3.90(m, 2H), 4.06(t, 2H), 4.27(t, 2H), 6.77(m, 1H), 6.90(m, 2H), 7.17(m, 1H) |
| A.784 | $C_2H_5$ | Tetrahydropyran-4-yl | —$(CH_2)_3$—O— | 3-Cl-phenyl | 3.90–4.10(m, 4H), 4.27(t, 2H) 6.77(m, 1H), 6.90(m, 2H), 7.17(m, 1H) |
| A.785 | n-$C_3H_7$ | Tetrahydropyran-4-yl | —$(CH_2)_3$—O— | 3-Cl-phenyl | 3.90–4.10(m, 4H), 4.27(t, 2H) 6.77(m, 1H), 6.90(m, 2H), 7.17(m, 1H) |
| A.786 | $C_2H_5$ | Tetrahydrothiopyran-3-yl | —$(CH_2)_3$—O— | 3-Cl-phenyl | 4.06(t, 2H), 4.27(t, 2H), 6.77(m, 1H), 6.90(m, 2H), 7.17(m, 1H) |
| A.787 | n-$C_3H_7$ | Tetrahydrothiopyran-3-yl | —$(CH_2)_3$—O— | 3-Cl-phenyl | 4.06(t, 2H), 4.27(t, 2H), 6.77(m, 1H), 6.90(m, 2H), 7.17(m, 1H) |
| A.788 | $C_2H_5$ | Tetrahydropyran-3-yl | —$(CH_2)_3$—O— | 4-Cl-phenyl | 3.90(m, 2H), 4.03(t, 2H), 4.23(t, 2H), 6.80(m, 2H), 7.20(m, 2H) |
| A.789 | n-$C_3H_7$ | Tetrahydropyran-3-yl | —$(CH_2)_3$—O— | 4-Cl-phenyl | 3.90(m, 2H), 4.03(t, 2H), 4.23(t, 2H), 6.80(m, 2H), 7.20(m, 2H) |
| A.790 | $C_2H_5$ | Tetrahydropyran-4-yl | —$(CH_2)_3$—O— | 4-Cl-phenyl | 3.90–4.09(m, 4H), 4.23(t, 2H) 6.80(m, 2H), 7.20(m, 2H) |
| A.791 | n-$C_3H_7$ | Tetrahydropyran-4-yl | —$(CH_2)_3$—O— | 4-Cl-phenyl | 3.90–4.09(m, 4H), 4.23(t, 2H) 6.80(m, 2H), 7.20(m, 2H) |
| A.792 | $C_2H_5$ | Tetrahydrothiopyran-3-yl | —$(CH_2)_3$—O— | 4-Cl-phenyl | 4.03(t, 2H), 4.23(t, 2H), 6.80(m, 2H), 7.20(m, 2H) |
| A.793 | n-$C_3H_7$ | Tetrahydrothiopyran-3-yl | —$(CH_2)_3$—O— | 4-Cl-phenyl | 4.03(t, 2H), 4.23(t, 2H), 6.80(m, 2H), 7.20(m, 2H) |
| A.794 | $C_2H_5$ | Tetrahydropyran-3-yl | —$(CH_2)_3$—O— | 4-$NO_2$-phenyl | 3.90(m, 2H), 4.20(t, 2H), 4.28(t, 2H), 6.93(d, 2H), 8.20(d, H) |
| A.795 | n-$C_3H_7$ | Tetrahydropyran-3-yl | —$(CH_2)_3$—O— | 4-$NO_2$-phenyl | 3.90(m, 2H), 4.20(t, 2H), 4.28(t, 2H), 6.93(d, 2H), 8.20(d, 2H) |
| A.796 | $C_2H_5$ | Tetrahydropyran-4-yl | —$(CH_2)_3$—O— | 4-$NO_2$-phenyl | 4.00(m, 2H), 4.20(t, 2H), 4.28(t, 2H), 6.93(d, 2H), 8.20(d, 2H) |
| A.797 | n-$C_3H_7$ | Tetrahydropyran-4-yl | —$(CH_2)_3$—O— | 4-$NO_2$-phenyl | 4.00(m, 2H), 4.20(t, 2H), 4.28(t, 2H), 6.93(d, 2H), |

TABLE 7-continued $$\text{(structure shown with } R^c, OH, NO-W-R^f, C, R^a, O \text{ substituents)} \quad (R^b, R^d, R^e = H)$$

| No. | $R^a$ | $R^c$ | W | $R^f$ | Phys. data NMR data in ppm Mp. in °C. |
|---|---|---|---|---|---|
| A.798 | $C_2H_5$ | Tetrahydrothiopyran-3-yl | $-(CH_2)_3-O-$ | 4-$NO_2$-phenyl | 8.20(d, 2H) 4.20(t, 2H), 4.28(t, 2H), 6.93(d, 2H), 8.20(d, 2H) |
| A.799 | n-$C_3H_7$ | Tetrahydrothiopyran-3-yl | $-(CH_2)_3-O-$ | 4-$NO_2$-phenyl | 4.20(t, 2H), 4.28(t, 2H), 6.93(d, 2H), 8.20(d, 2H) |
| A.800 | $C_2H_5$ | Tetrahydropyran-3-yl | $-(CH_2)_3-O-$ | 4-Br-phenyl | 3.90(m, 2H), 4.00(t, 2H), 4.27(t, 2H), 6.80(d, 2H), 7.37(d, 2H) |
| A.801 | n-$C_3H_7$ | Tetrahydropyran-3-yl | $-(CH_2)_3-O-$ | 4-Br-phenyl | 3.90(m, 2H), 4.00(t, 2H), 4.27(t, 2H), 6.80(d, 2H), 7.37(d, 2H) |
| A.802 | $C_2H_5$ | Tetrahydropyran-4-yl | $-(CH_2)_3-O-$ | 4-Br-phenyl | 3.90–4.10(m, 4H), 4.27(t, 2H), 6.80(d, 2H), 7.37(d, 2H) |
| A.803 | n-$C_3H_7$ | Tetrahydropyran-4-yl | $-(CH_2)_3-O-$ | 4-Br-phenyl | 3.90–4.10(m, 4H), 4.27(t, 2H), 6.80(d, 2H), 7.37(d, 2H) |
| A.804 | $C_2H_5$ | Tetrahydrothiopyran-4-yl | $-(CH_2)_3-O-$ | 4-Br-phenyl | 4.00(t, 2H), 4.27(t, 2H), 6.80(d, 2H), 7.37(d, 2H) |
| A.805 | n-$C_3H_7$ | Tetrahydrothiopyran-4-yl | $-(CH_2)_3-O-$ | 4-Br-phenyl | 4.00(t, 2H), 4.27(t, 2H), 6.80(d, 2H), 7.37(d, 2H) |
| A.806 | $C_2H_5$ | Tetrahydropyran-3-yl | $-(CH_2)_3-S-$ | Phenyl | 3.90(m, 2H), 4.17(t, 2H), 7.10–7.40(m, 5H) |
| A.807 | n-$C_3H_7$ | Tetrahydropyran-3-yl | $-(CH_2)_3-S-$ | Phenyl | 3.90(m, 2H), 4.17(t, 2H), 7.10–7.40(m, 5H) |
| A.808 | $C_2H_5$ | Tetrahydropyran-4-yl | $-(CH_2)_3-S-$ | Phenyl | 4.00(m, 2H), 4.17(t, 2H), 7.10–7.40(m, 5H) |
| A.809 | n-$C_3H_7$ | Tetrahydropyran-4-yl | $-(CH_2)_3-S-$ | Phenyl | 4.00(m, 2H), 4.17(t, 2H), 7.10–7.40(m, 5H) |
| A.810 | $C_2H_5$ | Tetrahydrothiopyran-3-yl | $-(CH_2)_3-S-$ | Phenyl | 4.17(t, 2H), 7.10–7.40(m, 5H) |
| A.811 | n-$C_3H_7$ | Tetrahydrothiopyran-3-yl | $-(CH_2)_3-S-$ | Phenyl | 4.17(t, 2H), 7.10–7.40(m, 5H) |
| A.812 | $C_2H_5$ | Tetrahydropyran-3-yl | $-(CH_2)_3-S-$ | 4-F-phenyl | 3.90(m, 2H), 4.17(t, 2H), 7.00(t, 2H), 7.33(m, 2H) |
| A.813 | n-$C_3H_7$ | Tetrahydropyran-3-yl | $-(CH_2)_3-S-$ | 4-F-phenyl | 3.90(m, 2H), 4.17(t, 2H), 7.00(t, 2H), 7.33(m, 2H) |
| A.814 | $C_2H_5$ | Tetrahydropyran-4-yl | $-(CH_2)_3-S-$ | 4-F-phenyl | 4.00(m, 2H), 4.17(t, 2H), 7.00(t, 2H), 7.33(m, 2H) |
| A.815 | n-$C_3H_7$ | Tetrahydropyran-4-yl | $-(CH_2)_3-S-$ | 4-F-phenyl | 4.00(m, 2H), 4.17(t, 2H), 7.00(t, 2H), 7.33(m, 2H) |
| A.816 | $C_2H_5$ | Tetrahydrothiopyran-3-yl | $-(CH_2)_3-S-$ | 4-F-phenyl | 4.17(t, 2H), 7.00(t, 2H), 7.33(m, 2H) |
| A.817 | n-$C_3H_7$ | Tetrahydrothiopyran-3-yl | $-(CH_2)_3-S-$ | 4-F-phenyl | 4.17(t, 2H), 7.00(t, 2H), 7.33(m, 2H) |
| A.818 | $C_2H_5$ | Tetrahydropyran-3-yl | $-(CH_2)_3-S-$ | 4-Cl-phenyl | 3.90(m, 2H), 4.17(t, 2H), 7.27(s, 4H) |
| A.819 | n-$C_3H_7$ | Tetrahydropyran-3-yl | $-(CH_2)_3-S-$ | 4-Cl-phenyl | 3.90(m, 2H), 4.17(t, 2H), 7.27(s, 4H) |
| A.820 | $C_2H_5$ | Tetrahydropyran-4-yl | $-(CH_2)_3-S-$ | 4-Cl-phenyl | 4.00(m, 2H), 4.17(t, 2H), 7.27(s, 4H) |
| A.821 | n-$C_3H_7$ | Tetrahydropyran-4-yl | $-(CH_2)_3-S-$ | 4-Cl-phenyl | 4.00(m, 2H), 4.17(t, 2H), 7.27(s, 4H) |
| A.822 | $C_2H_5$ | Tetrahydrothiopyran-3-yl | $-(CH_2)_3-S-$ | 4-Cl-phenyl | 4.17(t, 2H), 7.27(s, 4H) |
| A.823 | n-$C_3H_7$ | Tetrahydrothiopyran-3-yl | $-(CH_2)_3-S-$ | 4-Cl-phenyl | 4.17(t, 2H), 7.27(s, 4H) |
| A.824 | $C_2H_5$ | Tetrahydropyran-3-yl | $-(CH_2)_3-S-$ | 2-Cl-phenyl | 3.90(m, 2H), 4.20(t, 2H), 7.07–7.40(m, 4H) |
| A.825 | n-$C_3H_7$ | Tetrahydropyran-3-yl | $-(CH_2)_3-S-$ | 2-Cl-phenyl | 3.90(m, 2H), 4.20(t, 2H), 7.07–7.40(m, 4H) |
| A.826 | $C_2H_5$ | Tetrahydropyran-4-yl | $-(CH_2)_3-S-$ | 2-Cl-phenyl | 4.00(m, 2H), 4.20(t, 2H), 7.07–7.40(m, 4H) |
| A.827 | n-$C_3H_7$ | Tetrahydropyran-4-yl | $-(CH_2)_3-S-$ | 2-Cl-phenyl | 4.00(m, 2H), 4.20(t, 2H), 7.07–7.40(m, 4H) |
| A.828 | $C_2H_5$ | Tetrahydrothiopyran-3-yl | $-(CH_2)_3-S-$ | 2-Cl-phenyl | 4.20(t, 2H), 7.07–7.40(m, 4H) |
| A.829 | n-$C_3H_7$ | Tetrahydrothiopyran-3-yl | $-(CH_2)_3-S-$ | 2-Cl-phenyl | 4.20(t, 2H), 7.07–7.40(m, 4H) |
| A.830 | $C_2H_5$ | Tetrahydropyran-3-yl | $-(CH_2)_3-S-$ | 3-Cl-phenyl | 3.90(m, 2H), 4.20(t, 2H), 7.17(m, 3H), 7.30(m, 1H) |
| A.831 | n-$C_3H_7$ | Tetrahydropyran-3-yl | $-(CH_2)_3-S-$ | 3-Cl-phenyl | 3.90(m, 2H), 4.20(t, 2H), 7.17(m, 3H), 7.30(m, 1H) |
| A.832 | $C_2H_5$ | Tetrahydropyran-4-yl | $-(CH_2)_3-S-$ | 3-Cl-phenyl | 4.00(m, 2H), 4.20(t, 2H), |

TABLE 7-continued

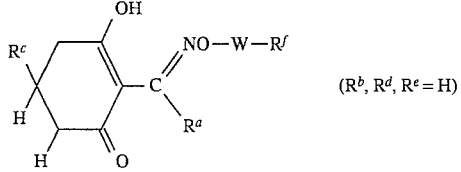

($R^b$, $R^d$, $R^e$ = H)

| No. | $R^a$ | $R^c$ | W | $R^f$ | Phys. data NMR data in ppm Mp. in °C. |
|---|---|---|---|---|---|
| A.833 | n-$C_3H_7$ | Tetrahydropyran-4-yl | —$(CH_2)_3$—S— | 3-Cl-phenyl | 7.17(m, 3H), 7.30(m, 1H) 4.00(m, 2H), 4.20(t, 2H), 7.17(m, 3H), 7.30(m, 1H) |
| A.834 | $C_2H_5$ | Tetrahydrothiopyran-3-yl | —$(CH_2)_3$—S— | 3-Cl-phenyl | 4.20(t, 2H), 7.17(m, 3H), 7.30(m, 1H) |
| A.835 | n-$C_3H_7$ | Tetrahydrothiopyran-3-yl | —$(CH_2)_3$—S— | 3-Cl-phenyl | 4.20(t, 2H), 7.17(m, 3H), 7.30(m, 1H) |
| A.836 | $C_2H_5$ | Tetrahydropyran-3-yl | —$(CH_2)_3$—S— | 2,5-$Cl_2$-phenyl | 3.90(m, 2H), 4.20(t, 2H), 7.07(dd, 1H), 7.20(d, 1H) 7.30(d, 1H) |
| A.837 | n-$C_3H_7$ | Tetrahydropyran-3-yl | —$(CH_2)_3$—S— | 2,5-$Cl_2$-phenyl | 3.90(m, 2H), 4.20(t, 2H), 7.07(dd, 1H), 7.20(d, 1H) 7.30(d, 1H) |
| A.838 | $C_2H_5$ | Tetrahydropyran-4-yl | —$(CH_2)_3$—S— | 2,5-$Cl_2$-phenyl | 4.00(m, 2H), 4.20(t, 2H), 7.07(dd, 1H), 7.20(d, 1H) 7.30(d, 1H) |
| A.839 | n-$C_3H_7$ | Tetrahydropyran-4-yl | —$(CH_2)_3$—S— | 2,5-$Cl_2$-phenyl | 4.00(m, 2H), 4.20(t, 2H), 7.07(dd, 1H), 7.20(d, 1H) 7.30(d, 1H) |
| A.840 | $C_2H_5$ | Tetrahydrothiopyran-3-yl | —$(CH_2)_3$—S— | 2,5-$Cl_2$-phenyl | 4.20(t, 2H), 7.07(dd, 1H), 7.20(d, 1H), 7.30(d, 1H) |
| A.841 | n-$C_3H_7$ | Tetrahydrothiopyran-3-yl | —$(CH_2)_3$—S— | 2,5-$Cl_2$-phenyl | 4.20(t, 2H), 7.07(dd, 1H), 7.20(d, 1H), 7.30(d, 1H) |
| A.842 | $C_2H_5$ | Tetrahydropyran-3-yl | —$(CH_2)_3$—S— | 2,6-$Cl_2$-phenyl | 3.90(m, 2H), 4.20(t, 2H), 7.20(t, 1H), 7.40(d, 2H) |
| A.843 | n-$C_3H_7$ | Tetrahydropyran-3-yl | —$(CH_2)_3$—S— | 2,6-$Cl_2$-phenyl | 3.90(m, 2H), 4.20(t, 2H), 7.20(t, 1H), 7.40(d, 2H) |
| A.844 | $C_2H_5$ | Tetrahydropyran-4-yl | —$(CH_2)_3$—S— | 2,6-$Cl_2$-phenyl | 4.00(m, 2H), 4.20(t, 2H), 7.20(t, 1H), 7.40(d, 2H) |
| A.845 | n-$C_3H_7$ | Tetrahydropyran-4-yl | —$(CH_2)_3$—S— | 2,6-$Cl_2$-phenyl | 4.00(m, 2H), 4.20(t, 2H), 7.20(t, 1H), 7.40(d, 2H) |
| A.846 | $C_2H_5$ | Tetrahydrothiopyran-3-yl | —$(CH_2)_3$—S— | 2,6-$Cl_2$-phenyl | 4.20(t, 2H), 7.20(t, 1H), 7.40(d, 2H) |
| A.847 | n-$C_3H_7$ | Tetrahydrothiopyran-3-yl | —$(CH_2)_3$—S— | 2,6-$Cl_2$-phenyl | 4.20(t, 2H), 7.20(t, 1H), 7.40(d, 2H) |
| A.848 | $C_2H_5$ | Tetrahydropyran-3-yl | —$CH_2CH_2OCH_2$— | Phenyl | 3.90(m, 2H), 4.25(t, 2H), 4.58(s, 2H), 7.38(s, 5H) |
| A.849 | n-$C_3H_7$ | Tetrahydropyran-3-yl | —$CH_2CH_2OCH_2$— | Phenyl | 3.90(m, 2H), 4.25(t, 2H), 4.58(s, 2H), 7.38(s, 5H) |
| A.850 | $C_2H_5$ | Tetrahydropyran-4-yl | —$CH_2CH_2OCH_2$— | Phenyl | 4.03(m, 2H), 4.33(m, 2H), 4.60(s, 2H), 7.40(s, 5H) |
| A.851 | n-$C_3H_7$ | Tetrahydropyran-4-yl | —$CH_2CH_2OCH_2$— | Phenyl | 4.03(m, 2H), 4.33(m, 2H), 4.60(s, 2H), 7.40(s, 5H) |
| A.852 | $C_2H_5$ | Tetrahydrothiopyran-3-yl | —$CH_2CH_2OCH_2$— | Phenyl | 4.27(m, 2H), 4.57(s, 2H), 7.35(s, 5H) |
| A.853 | n-$C_3H_7$ | Tetrahydrothiopyran-3-yl | —$CH_2CH_2OCH_2$— | Phenyl | 4.27(m, 2H), 4.57(s, 2H), 7.35(s, 5H) |
| A.854 | $C_2H_5$ | Tetrahydropyran-3-yl | —$CH_2CH_2OCH_2$— | 2-F-phenyl | 3.93(m, 2H), 4.27(m, 2H), 4.67(s, 2H), 6.93–7.50(m, 4H) |
| A.855 | n-$C_3H_7$ | Tetrahydropyran-3-yl | —$CH_2CH_2OCH_2$— | 2-F-phenyl | 3.93(m, 2H), 4.27(m, 2H), 4.67(s, 2H), 6.93–7.50(m, 4H) |
| A.856 | $C_2H_5$ | Tetrahydropyran-4-yl | —$CH_2CH_2OCH_2$— | 2-F-phenyl | 4.03(m, 2H), 4.27(m, 2H), 4.63(s, 2H), 6.97–7.50(m, 4H) |
| A.857 | n-$C_3H_7$ | Tetrahydropyran-4-yl | —$CH_2CH_2OCH_2$— | 2-F-phenyl | 4.03(m, 2H), 4.27(m, 2H), 4.63(s, 2H), 6.97–7.50(m, 4H) |
| A.858 | $C_2H_5$ | Tetrahydrothiopyran-3-yl | —$CH_2CH_2OCH_2$— | 2-F-phenyl | 4.27(m, 2H), 4.67(s, 2H), 6.97–7.50(m, 4H) |
| A.859 | n-$C_3H_7$ | Tetrahydrothiopyran-3-yl | —$CH_2CH_2OCH_2$— | 2-F-phenyl | 4.27(m, 2H), 4.67(s, 2H), 6.97–7.50(m, 4H) |
| A.860 | $C_2H_5$ | Tetrahydropyran-3-yl | —$CH_2CH_2OCH_2$— | 3-F-phenyl | 3.93(m, 2H), 4.27(m, 2H), 4.57(s, 2H), 6.90–7.15(m, 3H) 7.23–7.40(m, 1H) |
| A.861 | n-$C_3H_7$ | Tetrahydropyran-3-yl | —$CH_2CH_2OCH_2$— | 3-F-phenyl | 3.93(m, 2H), 4.27(m, 2H), 4.57(s, 2H), 6.90–7.15(m, 3H) 7.23–7.40(m, 1H) |
| A.862 | $C_2H_5$ | Tetrahydropyran-4-yl | —$CH_2CH_2OCH_2$— | 3-F-phenyl | 4.03(m, 2H), 4.25(m, 2H), |

TABLE 7-continued $(R^b, R^d, R^e = H)$

| No. | $R^a$ | $R^c$ | W | $R^f$ | Phys. data<br>NMR data in ppm<br>Mp. in °C. |
|---|---|---|---|---|---|
| | | | | | 4.60(s, 2H), 6.90–7.18(m, 3H)<br>7.26–7.40(m, 1H) |
| A.863 | n-C$_3$H$_7$ | Tetrahydropyran-4-yl | —CH$_2$CH$_2$OCH$_2$— | 3-F-phenyl | 4.03(m, 2H), 4.25(m, 2H),<br>4.60(s, 2H), 6.90–7.18(m, 3H)<br>7.26–7.40(m, 1H) |
| A.864 | C$_2$H$_5$ | Tetrahydrothiopyran-3-yl | —CH$_2$CH$_2$OCH$_2$— | 3-F-phenyl | 4.27(m, 2H), 4.60(s, 2H),<br>6.90–7.15(m, 3H),<br>7.23–7.40(m, 1H) |
| A.865 | n-C$_3$H$_7$ | Tetrahydrothiopyran-3-yl | —CH$_2$CH$_2$OCH$_2$— | 3-F-phenyl | 4.27(m, 2H), 4.60(s, 2H),<br>6.90–7.15(m, 3H),<br>7.23–7.40(m, 1H) |
| A.866 | C$_2$H$_5$ | Tetrahydropyran-3-yl | —CH$_2$CH$_2$OCH$_2$— | 4-F-phenyl | 3.93(m, 2H), 4.23(m, 2H),<br>4.53(s, 2H), 7.00(m, 2H),<br>7.30(m, 2H) |
| A.867 | n-C$_3$H$_7$ | Tetrahydropyran-3-yl | —CH$_2$CH$_2$OCH$_2$— | 4-F-phenyl | 3.93(m, 2H), 4.23(m, 2H),<br>4.53(s, 2H), 7.00(m, 2H),<br>7.30(m, 2H) |
| A.868 | C$_2$H$_5$ | Tetrahydropyran-4-yl | —CH$_2$CH$_2$OCH$_2$— | 4-F-phenyl | 92 |
| A.869 | n-C$_3$H$_7$ | Tetrahydropyran-4-yl | —CH$_2$CH$_2$OCH$_2$— | 4-F-phenyl | 4.00(m, 2H), 4.23(m, 2H),<br>4.53(s, 2H), 7.03(m, 2H),<br>7.30(m, 2H) |
| A.870 | C$_2$H$_5$ | Tetrahydrothiopyran-3-yl | —CH$_2$CH$_2$OCH$_2$— | 4-F-phenyl | 4.27(m, 2H), 4.53(s, 2H),<br>7.03(m, 2H), 7.30(m, 2H) |
| A.871 | n-C$_3$H$_7$ | Tetrahydrothiopyran-3-yl | —CH$_2$CH$_2$OCH$_2$— | 4-F-phenyl | 4.27(m, 2H), 4.53(s, 2H),<br>7.03(m, 2H), 7.30(m, 2H) |
| A.872 | C$_2$H$_5$ | Tetrahydropyran-3-yl | —CH$_2$CH$_2$OCH$_2$— | 2-Cl-phenyl | |
| A.873 | n-C$_3$H$_7$ | Tetrahydropyran-3-yl | —CH$_2$CH$_2$OCH$_2$— | 2-Cl-phenyl | |
| A.874 | C$_2$H$_5$ | Tetrahydropyran-4-yl | —CH$_2$CH$_2$OCH$_2$— | 2-Cl-phenyl | |
| A.875 | n-C$_3$H$_7$ | Tetrahydropyran-4-yl | —CH$_2$CH$_2$OCH$_2$— | 2-Cl-phenyl | |
| A.876 | C$_2$H$_5$ | Tetrahydrothiopyran-3-yl | —CH$_2$CH$_2$OCH$_2$— | 2-Cl-phenyl | |
| A.877 | n-C$_3$H$_7$ | Tetrahydrothiopyran-3-yl | —CH$_2$CH$_2$OCH$_2$— | 2-Cl-phenyl | |
| A.878 | C$_2$H$_5$ | Tetrahydropyran-3-yl | —CH$_2$CH$_2$OCH$_2$— | 3-Cl-phenyl | |
| A.879 | n-C$_3$H$_7$ | Tetrahydropyran-3-yl | —CH$_2$CH$_2$OCH$_2$— | 3-Cl-phenyl | |
| A.880 | C$_2$H$_5$ | Tetrahydropyran-4-yl | —CH$_2$CH$_2$OCH$_2$— | 3-Cl-phenyl | |
| A.881 | n-C$_3$H$_7$ | Tetrahydropyran-4-yl | —CH$_2$CH$_2$OCH$_2$— | 3-Cl-phenyl | |
| A.882 | C$_2$H$_5$ | Tetrahydrothiopyran-3-yl | —CH$_2$CH$_2$OCH$_2$— | 3-Cl-phenyl | |
| A.883 | n-C$_3$H$_7$ | Tetrahydrothiopyran-3-yl | —CH$_2$CH$_2$OCH$_2$— | 3-Cl-phenyl | |
| A.884 | C$_2$H$_5$ | Tetrahydropyran-3-yl | —CH$_2$CH$_2$OCH$_2$— | 4-Cl-phenyl | 3.93(m, 2H), 4.27(m, 2H),<br>4.53(s, 2H), 7.28(m, 4H) |
| A.885 | n-C$_3$H$_7$ | Tetrahydropyran-3-yl | —CH$_2$CH$_2$OCH$_2$— | 4-Cl-phenyl | 3.93(m, 2H), 4.27(m, 2H),<br>4.53(s, 2H), 7.28(m, 4H) |
| A.886 | C$_2$H$_5$ | Tetrahydropyran-4-yl | —CH$_2$CH$_2$OCH$_2$— | 4-Cl-phenyl | 67–72 |
| A.887 | n-C$_3$H$_7$ | Tetrahydropyran-4-yl | —CH$_2$CH$_2$OCH$_2$— | 4-Cl-phenyl | 4.00(m, 2H), 4.23(m, 2H),<br>4.53(s, 2H), 7.28(m, 4H) |
| A.888 | C$_2$H$_5$ | Tetrahydrothiopyran-3-yl | —CH$_2$CH$_2$OCH$_2$— | 4-Cl-phenyl | 4.27(m, 2H), 4.53(s, 2H),<br>7.28(m, 4H) |
| A.889 | n-C$_3$H$_7$ | Tetrahydrothiopyran-3-yl | —CH$_2$CH$_2$OCH$_2$— | 4-Cl-phenyl | 4.27(m, 2H), 4.53(s, 2H),<br>7.28(m, 4H) |
| A.890 | C$_2$H$_5$ | Tetrahydropyran-3-yl | —CH$_2$CH$_2$OCH$_2$— | 2-CH$_3$-phenyl | 3.93(m, 2H), 4.23(m, 2H),<br>4.57(s, 2H), 7.09–7.33(m, 4H) |
| A.891 | n-C$_3$H$_7$ | Tetrahydropyran-3-yl | —CH$_2$CH$_2$OCH$_2$— | 2-CH$_3$-phenyl | 3.93(m, 2H), 4.23(m, 2H),<br>4.57(s, 2H), 7.09–7.33(m, 4H) |
| A.892 | C$_2$H$_5$ | Tetrahydropyran-4-yl | —CH$_2$CH$_2$OCH$_2$— | 2-CH$_3$-phenyl | 4.00(m, 2H), 4.23(m, 2H),<br>4.57(s, 2H), 7.09–7.33(m, 4H) |
| A.893 | n-C$_3$H$_7$ | Tetrahydropyran-4-yl | —CH$_2$CH$_2$OCH$_2$— | 2-CH$_3$-phenyl | 4.00(m, 2H), 4.23(m, 2H),<br>4.57(s, 2H), 7.09–7.33(m, 4H) |
| A.894 | C$_2$H$_5$ | Tetrahydrothiopyran-3-yl | —CH$_2$CH$_2$OCH$_2$— | 2-CH$_3$-phenyl | 4.23(m, 2H), 4.57(s, 2H),<br>7.09–7.33(m, 4H) |
| A.895 | n-C$_3$H$_7$ | Tetrahydrothiopyran-3-yl | —CH$_2$CH$_2$OCH$_2$— | 2-CH$_3$-phenyl | 4.23(m, 2H), 4.57(s, 2H),<br>7.09–7.33(m, 4H) |
| A.896 | C$_2$H$_5$ | Tetrahydropyran-3-yl | —CH$_2$CH$_2$OCH$_2$— | 3-CH$_3$-phenyl | 3.93(m, 2H), 4.25(m, 2H),<br>4.57(s, 2H), 7.00–7.32(m, 4H) |
| A.897 | n-C$_3$H$_7$ | Tetrahydropyran-3-yl | —CH$_2$CH$_2$OCH$_2$— | 3-CH$_3$-phenyl | 3.93(m, 2H), 4.25(m, 2H),<br>4.57(s, 2H), 7.00–7.32(m, 4H) |
| A.898 | C$_2$H$_5$ | Tetrahydropyran-4-yl | —CH$_2$CH$_2$OCH$_2$— | 3-CH$_3$-phenyl | 4.00(m, 2H), 4.27(m, 2H),<br>4.57(s, 2H), 7.00–7.32(m, 4H) |

TABLE 7-continued $$\text{(structure shown with } R^b, R^d, R^e = H\text{)}$$

| No. | $R^a$ | $R^c$ | W | $R^f$ | Phys. data NMR data in ppm Mp. in °C. |
|---|---|---|---|---|---|
| A.899 | n-$C_3H_7$ | Tetrahydropyran-4-yl | —$CH_2CH_2OCH_2$— | 3-$CH_3$-phenyl | 4.00(m, 2H), 4.27(m, 2H), 4.57(s, 2H), 7.00–7.32(m, 4H) |
| A.900 | $C_2H_5$ | Tetrahydrothiopyran-3-yl | —$CH_2CH_2OCH_2$— | 3-$CH_3$-phenyl | 4.27(m, 2H), 4.60(s, 2H), 7.00–7.32(m, 4H) |
| A.901 | n-$C_3H_7$ | Tetrahydrothiopyran-3-yl | —$CH_2CH_2OCH_2$— | 3-$CH_3$-phenyl | 4.27(m, 2H), 4.60(s, 2H), 7.00–7.32(m, 4H) |
| A.902 | $C_2H_5$ | Tetrahydropyran-3-yl | —$CH_2CH_2OCH_2$— | 4-$CH_3$-phenyl | 3.93(m, 2H), 4.20(m, 2H), 4.53(s, 2H), 7.07–7.30(m, 4H) |
| A.903 | n-$C_3H_7$ | Tetrahydropyran-3-yl | —$CH_2CH_2OCH_2$— | 4-$CH_3$-phenyl | 3.93(m, 2H), 4.20(m, 2H), 4.53(s, 2H), 7.07–7.30(m, 4H) |
| A.904 | $C_2H_5$ | Tetrahydropyran-4-yl | —$CH_2CH_2OCH_2$— | 4-$CH_3$-phenyl | 4.00(m, 2H), 4.23(m, 2H), 4.57(s, 2H), 7.03–7.27(m, 4H) |
| A.905 | n-$C_3H_7$ | Tetrahydropyran-4-yl | —$CH_2CH_2OCH_2$— | 4-$CH_3$-phenyl | 4.00(m, 2H), 4.23(m, 2H), 4.57(s, 2H), 7.03–7.27(m, 4H) |
| A.906 | $C_2H_5$ | Tetrahydrothiopyran-3-yl | —$CH_2CH_2OCH_2$— | 4-$CH_3$-phenyl | 4.23(m, 2H), 4.57(s, 2H), 7.07–7.30(m, 4H) |
| A.907 | n-$C_3H_7$ | Tetrahydrothiopyran-3-yl | —$CH_2CH_2OCH_2$— | 4-$CH_3$-phenyl | 4.28(m, 2H), 4.57(s, 2H), 7.07–7.30(m, 4H) |
| A.908 | $C_2H_5$ | Tetrahydropyran-3-yl | —$CH_2CH_2OCH_2$— | 4-tert.-$C_4H_9$ | 3.93(m, 2H), 4.23(m, 2H), 4.53(s, 2H), 7.20–7.40(m, 4H) |
| A.909 | n-$C_3H_7$ | Tetrahydropyran-3-yl | —$CH_2CH_2OCH_2$— | 4-tert.-$C_4H_9$ | 3.93(m, 2H), 4.23(m, 2H), 4.53(s, 2H), 7.20–7.40(m, 4H) |
| A.910 | $C_2H_5$ | Tetrahydropyran-4-yl | —$CH_2CH_2OCH_2$— | 4-tert.-$C_4H_9$ | 4.00(m, 2H), 4.23(m, 2H), 4.53(s, 2H), 7.20–7.40(m, 4H) |
| A.911 | n-$C_3H_7$ | Tetrahydropyran-4-yl | —$CH_2CH_2OCH_2$— | 4-tert.-$C_4H_9$ | 4.00(m, 2H), 4.23(m, 2H), 4.53(s, 2H), 7.20–7.40(m, 4H) |
| A.912 | $C_2H_5$ | Tetrahydrothiopyran-3-yl | —$CH_2CH_2OCH_2$— | 4-tert.-$C_4H_9$ | 4.23(m, 2H), 4.53(s, 2H), 7.20–7.40(m, 4H) |
| A.913 | n-$C_3H_7$ | Tetrahydrothiopyran-3-yl | —$CH_2CH_2OCH_2$— | 4-tert.-$C_4H_9$ | 4.23(m, 2H), 4.53(s, 2H), 7.20–7.40(m, 4H) |
| A.914 | $C_2H_5$ | Tetrahydropyran-3-yl | —$CH_2CH_2SCH_2$— | Phenyl | 3.73(s, 2H), 3.90(m, 2H), 4.17(t, 2H), 7.28(s, 5H) |
| A.915 | n-$C_3H_7$ | Tetrahydropyran-3-yl | —$CH_2CH_2SCH_2$— | Phenyl | 3.73(s, 2H), 3.90(m, 2H), 4.17(t, 2H), 7.28(s, 5H) |
| A.916 | $C_2H_5$ | Tetrahydropyran-4-yl | —$CH_2CH_2SCH_2$— | Phenyl | 3.77(s, 2H), 4.00(m, 2H), 4.13(t, 2H), 7.28(s, 5H) |
| A.917 | n-$C_3H_7$ | Tetrahydropyran-4-yl | —$CH_2CH_2SCH_2$— | Phenyl | 3.77(s, 2H), 4.00(m, 2H), 4.13(t, 2H), 7.28(s, 5H) |
| A.918 | $C_2H_5$ | Tetrahydrothiopyran-3-yl | —$CH_2CH_2SCH_2$— | Phenyl | 3.80(s, 2H), 4.13(t, 2H), 7.28(s, 5H) |
| A.919 | n-$C_3H_7$ | Tetrahydrothiopyran-3-yl | —$CH_2CH_2SCH_2$— | Phenyl | 3.80(s, 2H), 4.13(t, 2H), 7.28(s, 5H) |
| A.920 | $C_2H_5$ | Tetrahydropyran-3-yl | —$CH_2CH_2SCH_2$— | 4-F-phenyl | 3.72(s, 2H), 3.90(m, 2H), 4.13(t, 2H), 7.00(m, 2H), 7.30(m, 2H) |
| A.921 | n-$C_3H_7$ | Tetrahydropyran-3-yl | —$CH_2CH_2SCH_2$— | 4-F-phenyl | 3.72(s, 2H), 3.90(m, 2H), 4.13(t, 2H), 7.00(m, 2H), 7.30(m, 2H) |
| A.922 | $C_2H_5$ | Tetrahydropyran-4-yl | —$CH_2CH_2SCH_2$— | 4-F-phenyl | 63–65 |
| A.923 | n-$C_3H_7$ | Tetrahydropyran-4-yl | —$CH_2CH_2SCH_2$— | 4-F-phenyl | 3.73(s, 2H), 4.00(m, 2H), 4.13(t, 2H), 7.00(m, 2H), 7.30(m, 2H) |
| A.924 | $C_2H_5$ | Tetrahydrothiopyran-3-yl | —$CH_2CH_2SCH_2$— | 4-F-phenyl | 3.75(s, 2H), 4.13(t, 2H), 7.00(m, 2H), 7.30(m, 2H) |
| A.925 | n-$C_3H_7$ | Tetrahydrothiopyran-3-yl | —$CH_2CH_2SCH_2$— | 4-F-phenyl | 3.75(s, 2H), 4.13(t, 2H), 7.00(m, 2H), 7.30(m, 2H) |
| A.926 | $C_2H_5$ | Tetrahydropyran-3-yl | —$CH_2CH_2SCH_2$— | 4-Cl-phenyl | 3.77(s, 2H), 3.93(m, 2H), 4.13(t, 2H), 7.30(s, 4H) |
| A.927 | n-$C_3H_7$ | Tetrahydropyran-3-yl | —$CH_2CH_2SCH_2$— | 4-Cl-phenyl | 3.77(s, 2H), 3.93(m, 2H), 4.13(t, 2H), 7.30(s, 4H) |
| A.928 | $C_2H_5$ | Tetrahydropyran-4-yl | —$CH_2CH_2SCH_2$— | 4-Cl-phenyl | 3.73(s, 2H), 4.00(m, 2H), 4.17(t, 2H), 7.30(s, 4H) |
| A.929 | n-$C_3H_7$ | Tetrahydropyran-4-yl | —$CH_2CH_2SCH_2$— | 4-Cl-phenyl | 3.73(s, 2H), 4.00(m, 2H), 4.17(t, 2H), 7.30(s, 4H) |
| A.930 | $C_2H_5$ | Tetrahydrothiopyran-3-yl | —$CH_2CH_2SCH_2$— | 4-Cl-phenyl | 3.73(s, 2H), 4.13(m, 2H), 7.30(s, 4H) |

TABLE 7-continued $(R^b, R^d, R^e = H)$

| No. | $R^a$ | $R^c$ | W | $R^f$ | Phys. data NMR data in ppm Mp. in °C. |
|---|---|---|---|---|---|
| A.931 | n-C$_3$H$_7$ | Tetrahydrothiopyran-3-yl | —CH$_2$CH$_2$SCH$_2$— | 4-Cl-phenyl | 3.73(s, 2H), 4.13(m, 2H), 7.30(s, 4H) |
| A.932 | C$_2$H$_5$ | Tetrahydropyran-3-yl | —(CH$_2$)$_4$—O— | Phenyl | 3.70–4.20(m, 6H), 6.90(m, 3H) 7.30(m, 2H) |
| A.933 | n-C$_3$H$_7$ | Tetrahydropyran-3-yl | —(CH$_2$)$_4$—O— | Phenyl | 3.70–4.20(m, 6H), 6.90(m, 3H) 7.30(m, 2H) |
| A.934 | C$_2$H$_5$ | Tetrahydropyran-4-yl | —(CH$_2$)$_4$—O— | Phenyl | 3.83–4.23(m, 6H), 6.90(m, 3H) 7.30(m, 2H) |
| A.935 | n-C$_3$H$_7$ | Tetrahydropyran-4-yl | —(CH$_2$)$_4$—O— | Phenyl | 3.83–4.23(m, 6H), 6.90(m, 3H) 7.30(m, 2H) |
| A.936 | C$_2$H$_5$ | Tetrahydrothiopyran-3-yl | —(CH$_2$)$_4$—O— | Phenyl | 4.00(bs, 2H), 4.13(bs, 2H), 6.90(m, 3H) 7.30(m, 2H) |
| A.937 | n-C$_3$H$_7$ | Tetrahydrothiopyran-3-yl | —(CH$_2$)$_4$—O— | Phenyl | 4.00(bs, 2H), 4.13(bs, 2H), 6.90(m, 3H) 7.30(m, 2H) |
| A.938 | C$_2$H$_5$ | Tetrahydropyran-3-yl | —(CH$_2$)$_4$—O— | 2-F-phenyl | 3.93(m, 2H), 4.00–4.20(m, 4H) 6.80–7.15(m, 4H) |
| A.939 | n-C$_3$H$_7$ | Tetrahydropyran-3-yl | —(CH$_2$)$_4$—O— | 2-F-phenyl | 3.93(m, 2H), 4.00–4.20(m, 4H) 6.80–7.15(m, 4H) |
| A.940 | C$_2$H$_5$ | Tetrahydropyran-4-yl | —(CH$_2$)$_4$—O— | 2-F-phenyl | 68–72 |
| A.941 | n-C$_3$H$_7$ | Tetrahydropyran-4-yl | —(CH$_2$)$_4$—O— | 2-F-phenyl | 3.90–4.20(m, 6H), 6.80–7.15 (m, 4H) |
| A.942 | C$_2$H$_5$ | Tetrahydrothiopyran-3-yl | —(CH$_2$)$_4$—O— | 2-F-phenyl | 4.00–4.20(m, 4H), 6.80–7.15 (m, 4H) |
| A.943 | n-C$_3$H$_7$ | Tetrahydrothiopyran-3-yl | —(CH$_2$)$_4$—O— | 2-F-phenyl | 4.00–4.20(m, 4H), 6.80–7.15 (m, 4H) |
| A.944 | C$_2$H$_5$ | Tetrahydropyran-3-yl | —(CH$_2$)$_4$—O— | 3-F-phenyl | |
| A.945 | n-C$_3$H$_7$ | Tetrahydropyran-3-yl | —(CH$_2$)$_4$—O— | 3-F-phenyl | |
| A.946 | C$_2$H$_5$ | Tetrahydropyran-4-yl | —(CH$_2$)$_4$—O— | 3-F-phenyl | |
| A.947 | n-C$_3$H$_7$ | Tetrahydropyran-4-yl | —(CH$_2$)$_4$—O— | 3-F-phenyl | |
| A.948 | C$_2$H$_5$ | Tetrahydrothiopyran-3-yl | —(CH$_2$)$_4$—O— | 3-F-phenyl | |
| A.949 | n-C$_3$H$_7$ | Tetrahydrothiopyran-3-yl | —(CH$_2$)$_4$—O— | 3-F-phenyl | |
| A.950 | C$_2$H$_5$ | Tetrahydropyran-3-yl | —(CH$_2$)$_4$—O— | 4-F-phenyl | 3.80–4.20(m, 6H), 6.75–7.05 (m, 4H) |
| A.951 | n-C$_3$H$_7$ | Tetrahydropyran-3-yl | —(CH$_2$)$_4$—O— | 4-F-phenyl | 3.80–4.20(m, 6H), 6.75–7.05 (m, 4H) |
| A.952 | C$_2$H$_5$ | Tetrahydropyran-4-yl | —(CH$_2$)$_4$—O— | 4-F-phenyl | 3.90–4.20(m, 6H), 6.75–7.05 (m, 4H) |
| A.953 | n-C$_3$H$_7$ | Tetrahydropyran-4-yl | —(CH$_2$)$_4$—O— | 4-F-phenyl | 3.90–4.20(m, 6H), 6.75–7.05 (m, 4H) |
| A.954 | C$_2$H$_5$ | Tetrahydrothiopyran-3-yl | —(CH$_2$)$_4$—O— | 4-F-phenyl | 3.90–4.20(m, 4H), 6.75–7.05 (m, 4H) |
| A.955 | n-C$_3$H$_7$ | Tetrahydrothiopyran-3-yl | —(CH$_2$)$_4$—O— | 4-F-phenyl | 3.90–4.20(m, 4H), 6.75–7.05 (m, 4H) |
| A.956 | C$_2$H$_5$ | Tetrahydropyran-3-yl | —(CH$_2$)$_4$—O— | 4-Cl-phenyl | 3.80–4.20(m, 6H), 6.80(m, 2H) 7.20(m, 2H) |
| A.957 | n-C$_3$H$_7$ | Tetrahydropyran-3-yl | —(CH$_2$)$_4$—O— | 4-Cl-phenyl | 3.80–4.20(m, 6H), 6.80(m, 2H) 7.20(m, 2H) |
| A.958 | C$_2$H$_5$ | Tetrahydropyran-4-yl | —(CH$_2$)$_4$—O— | 4-Cl-phenyl | 3.90–4.20(m, 6H), 6.80(m, 2H) 7.20(m, 2H) |
| A.959 | n-C$_3$H$_7$ | Tetrahydropyran-4-yl | —(CH$_2$)$_4$—O— | 4-Cl-phenyl | 3.90–4.20(m, 6H), 6.80(m, 2H) 7.20(m, 2H) |
| A.960 | C$_2$H$_5$ | Tetrahydrothiopyran-3-yl | —(CH$_2$)$_4$—O— | 4-Cl-phenyl | 3.90–4.20(m, 4H), 6.80(m, 2H) 7.20(m, 2H) |
| A.961 | n-C$_3$H$_7$ | Tetrahydrothiopyran-3-yl | —(CH$_2$)$_4$—O— | 4-Cl-phenyl | 3.90–4.20(m, 4H), 6.80(m, 2H) 7.20(m, 2H) |
| A.962 | C$_2$H$_5$ | Tetrahydropyran-3-yl | —(CH$_2$)$_4$—O— | 2,6-Cl$_2$-phenyl | 3.93(m, 2H), 4.00–4.25(m, 4H) 7.00(t, 1H), 7.30(d, 2H) |
| A.963 | n-C$_3$H$_7$ | Tetrahydropyran-3-yl | —(CH$_2$)$_4$—O— | 2,6-Cl$_2$-phenyl | 3.93(m, 2H), 4.00–4.25(m, 4H) 7.00(t, 1H), 7.30(d, 2H) |
| A.964 | C$_2$H$_5$ | Tetrahydropyran-4-yl | —(CH$_2$)$_4$—O— | 2,6-Cl$_2$-phenyl | 3.90–4.25(m, 6H), 7.00(t, 1H) 7.30(d, 2H) |
| A.965 | n-C$_3$H$_7$ | Tetrahydropyran-4-yl | —(CH$_2$)$_4$—O— | 2,6-Cl$_2$-phenyl | 3.90–4.25(m, 6H), 7.00(t, 1H) 7.30(d, 2H) |
| A.966 | C$_2$H$_5$ | Tetrahydrothiopyran-3-yl | —(CH$_2$)$_4$—O— | 2,6-Cl$_2$-phenyl | 4.00–4.20(m, 4H), 7.00(t, 1H) 7.30(d, 2H) |
| A.967 | n-C$_3$H$_7$ | Tetrahydrothiopyran-3-yl | —(CH$_2$)$_4$—O— | 2,6-Cl$_2$-phenyl | 4.00–4.20(m, 4H), 7.00(t, 1H) |

TABLE 7-continued (structure shown with Rc, Ra, OH, NO—W—Rf, and C=O groups; Rb, Rd, Re = H)

| No. | Ra | Rc | W | Rf | Phys. data NMR data in ppm Mp. in °C |
|---|---|---|---|---|---|
| A.968 | C₂H₅ | Tetrahydropyran-3-yl | —CH₂CH₂OCH₂CH₂— | Phenyl | 7.30(d, 2H) 3.90(m, 2H), 4.20(m, 2H), 7.25(m, 5H) |
| A.969 | n-C₃H₇ | Tetrahydropyran-3-yl | —CH₂CH₂OCH₂CH₂— | Phenyl | 3.90(m, 2H), 4.20(m, 2H), 7.25(m, 5H) |
| A.970 | C₂H₅ | Tetrahydropyran-4-yl | —CH₂CH₂OCH₂CH₂— | Phenyl | |
| A.971 | n-C₃H₇ | Tetrahydropyran-4-yl | —CH₂CH₂OCH₂CH₂— | Phenyl | |
| A.972 | C₂H₅ | Tetrahydrothiopyran-3-yl | —CH₂CH₂OCH₂CH₂— | Phenyl | 4.20(m, 2H), 7.25(m, 5H) |
| A.973 | n-C₃H₇ | Tetrahydrothiopyran-3-yl | —CH₂CH₂OCH₂CH₂— | Phenyl | 4.20(m, 2H), 7.25(m, 5H) |
| A.974 | C₂H₅ | Tetrahydropyran-3-yl | —CH₂CH₂OCH₂CH₂— | 4-F-phenyl | 3.90(m, 2H), 4.17(m, 2H), 6.93(m, 2H), 7.13(m, 2H) |
| A.975 | n-C₃H₇ | Tetrahydropyran-3-yl | —CH₂CH₂OCH₂CH₂— | 4-F-phenyl | 3.90(m, 2H), 4.17(m, 2H), 6.93(m, 2H), 7.13(m, 2H) |
| A.976 | C₂H₅ | Tetrahydropyran-4-yl | —CH₂CH₂OCH₂CH₂— | 4-F-phenyl | |
| A.977 | n-C₃H₇ | Tetrahydropyran-4-yl | —CH₂CH₂OCH₂CH₂— | 4-F-phenyl | |
| A.978 | C₂H₅ | Tetrahydrothiopyran-3-yl | —CH₂CH₂OCH₂CH₂— | 4-F-phenyl | 4.17(m, 2H), 6.93(m, 2H), 7.13(m, 2H) |
| A.979 | n-C₃H₇ | Tetrahydrothiopyran-3-yl | —CH₂CH₂OCH₂CH₂— | 4-F-phenyl | 4.17(m, 2H), 6.93(m, 2H), 7.13(m, 2H) |
| A.980 | C₂H₅ | Tetrahydropyran-3-yl | —CH₂CH₂OCH₂CH₂— | 4-Cl-phenyl | 3.90(m, 2H), 4.17(m, 2H), 7.13(m, 4H) |
| A.981 | n-C₃H₇ | Tetrahydropyran-3-yl | —CH₂CH₂OCH₂CH₂— | 4-Cl-phenyl | 3.90(m, 2H), 4.17(m, 2H), 7.13(m, 4H) |
| A.982 | C₂H₅ | Tetrahydropyran-4-yl | —CH₂CH₂OCH₂CH₂— | 4-Cl-phenyl | |
| A.983 | n-C₃H₇ | Tetrahydropyran-4-yl | —CH₂CH₂OCH₂CH₂— | 4-Cl-phenyl | |
| A.984 | C₂H₅ | Tetrahydrothiopyran-3-yl | —CH₂CH₂OCH₂CH₂— | 4-Cl-phenyl | 4.17(m, 2H), 7.13(m, 4H) |
| A.985 | n-C₃H₇ | Tetrahydrothiopyran-3-yl | —CH₂CH₂OCH₂CH₂— | 4-Cl-phenyl | 4.17(m, 2H), 7.13(m, 4H) |
| A.986 | C₂H₅ | Tetrahydropyran-3-yl | —(CH₂)₅—O— | Phenyl | 3.80–4.17(m, 6H), 6.90(m, 3H) 7.27(m, 2H) |
| A.987 | n-C₃H₇ | Tetrahydropyran-3-yl | —(CH₂)₅—O— | Phenyl | 3.80–4.17(m, 6H), 6.90(m, 3H) 7.27(m, 2H) |
| A.988 | C₂H₅ | Tetrahydropyran-4-yl | —(CH₂)₅—O— | Phenyl | 3.90–4.17(m, 6H), 6.90(m, 3H) 7.27(m, 2H) |
| A.989 | n-C₃H₇ | Tetrahydropyran-4-yl | —(CH₂)₅—O— | Phenyl | 3.90–4.17(m, 6H), 6.90(m, 3H) 7.27(m, 2H) |
| A.990 | C₂H₅ | Tetrahydrothiopyran-3-yl | —(CH₂)₅—O— | Phenyl | 3.97(t, 2H), 4.07(t, 2H), 6.90(m, 3H), 7.27(m, 2H) |
| A.991 | n-C₃H₇ | Tetrahydrothiopyran-3-yl | —(CH₂)₅—O— | Phenyl | 3.97(t, 2H), 4.07(t, 2H), 6.90(m, 3H), 7.27(m, 2H) |
| A.992 | C₂H₅ | Tetrahydropyran-3-yl | —(CH₂)₅—O— | 4-F-phenyl | 3.90(m, 4H), 4.03(t, 2H), 6.70–7.03(m, 4H) |
| A.993 | n-C₃H₇ | Tetrahydropyran-3-yl | —(CH₂)₅—O— | 4-F-phenyl | 3.90(m, 4H), 4.03(t, 2H), 6.70–7.03(m, 4H) |
| A.994 | C₂H₅ | Tetrahydropyran-4-yl | —(CH₂)₅—O— | 4-F-phenyl | 3.83–4.13(m, 6H), 6.70–7.03 (m, 4H) |
| A.995 | n-C₃H₇ | Tetrahydropyran-4-yl | —(CH₂)₅—O— | 4-F-phenyl | 3.83–4.13(m, 6H), 6.70–7.03 (m, 4H) |
| A.996 | C₂H₅ | Tetrahydrothiopyran-3-yl | —(CH₂)₅—O— | 4-F-phenyl | 3.90(t, 2H), 4.03(t, 2H) 6.70–7.03(m, 4H) |
| A.997 | n-C₃H₇ | Tetrahydrothiopyran-3-yl | —(CH₂)₅—O— | 4-F-phenyl | 3.90(t, 2H), 4.03(t, 2H) 6.70–7.03(m, 4H) |
| A.998 | C₂H₅ | Tetrahydropyran-3-yl | —(CH₂)₅—O— | 4-Cl-phenyl | 3.80–4.10(m, 6H), 6.80(d, 2H) 7.20(d, 2H) |
| A.999 | n-C₃H₇ | Tetrahydropyran-3-yl | —(CH₂)₅—O— | 4-Cl-phenyl | 3.80–4.10(m, 6H), 6.80(d, 2H) 7.20(d, 2H) |
| A.1000 | C₂H₅ | Tetrahydropyran-4-yl | —(CH₂)₅—O— | 4-Cl-phenyl | 3.87–4.10(m, 6H), 6.80(d, 2H) 7.20(d, 2H) |
| A.1001 | n-C₃H₇ | Tetrahydropyran-4-yl | —(CH₂)₅—O— | 4-Cl-phenyl | 3.87–4.10(m, 6H), 6.80(d, 2H) 7.20(d, 2H) |
| A.1002 | C₂H₅ | Tetrahydrothiopyran-3-yl | —(CH₂)₅—O— | 4-Cl-phenyl | 54–61 |
| A.1003 | n-C₃H₇ | Tetrahydrothiopyran-3-yl | —(CH₂)₅—O— | 4-Cl-phenyl | 3.90(t, 2H), 4.07(t, 2H), 6.80(d, 2H), 7.20(d, 2H) |

The herbicidal active ingredients from the group consisting of the 2-(4-hetaryloxy)- or 2-(4-aryloxy)-phenoxyacetic acid derivatives of the formula III

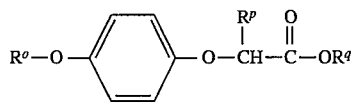

where $R^o$ is phenyl, pyridyl, benzoxazyl, benzothiazyl or benzopyrazinyl, where these aromatic ring systems may furthermore carry one or two radicals selected from the group consisting of:

nitro, halogen, such as fluorine, chlorine, bromine and iodine, especially fluorine and chlorine, straight-chain or branched $C_1$-$C_4$-alkyl, such as methyl, ethyl, n-propyl, isopropyl, n-butyl and tert-butyl, partially or completely halogenated $C_1$-$C_4$-alkyl, in particular $C_1$-$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably trifluoromethyl, partially or completely halogenated $C_1$-$C_4$-alkoxy, in particular $C_1$-$C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, preferably trifluoromethoxy;

$R^p$ is hydrogen or methyl, preferably methyl, $R^q$ is hydrogen or straight-chain or branched $C_1$-$C_4$-alkyl as stated above, in particular methyl, ethyl, n-propyl and n-butyl, $C_3$-$C_4$-alkenyl, such as prop-1-en-1-yl, prop-2-en-1-yl, but-2-en-1-yl, but-3-en-1-yl, 1-methylprop-2-en-1-yl or 2-methylprop-2-en-1-yl, in particular prop-2-en-1-yl, $C_3$- or $C_4$-alkynyl, such as prop-1-yn-1-yl, prop-2-yn-1-yl, but-2-yn-1-yl, but-3-yn-1-yl, 1-methylprop-2-yn-1-yl, 2-methyl-prop-2-yn-1-yl, in particular prop-2-yn-1-yl, $C_1$-$C_4$-alkoxy-$C_1$-$C_4$-alkyl, such as methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, methoxyethyl, ethoxyethyl, n-propoxyethyl, (1-methylethoxy)ethyl, n-butoxyethyl, (1-methylpropoxy)ethyl, (2-methylpropoxy)ethyl, (1,1-dimethylethoxy)ethyl, 3-methoxypropyl, 2-methoxypropyl and 2-ethoxypropyl, preferably methoxymethyl and ethoxyethyl, $C_3$- or $C_4$-alkylideneiminoxy-$C_2$- or $C_3$-alkyl, in particular 2-propylideneiminoxyethyl, tetrahydrofuranylmethyl, isoxazolidine or one equivalent of a plant-tolerated cation, for example an alkali metal cation, such as sodium or potassium, one equivalent of an alkaline earth metal cation, such as calcium, magnesium or barium, manganese, copper, zinc or iron cations, ammonium cations having, if desired, from one to three substituents selected from the group consisting of 3 $C_1$-$C_4$-alkyl radicals, 3-hydroxy-$C_1$-$C_4$-alkyl radicals and one phenyl or benzyl radical, such as tetraalkyl- or benzyltrialkylammonium cations, phosphonium cations, sulfonium cations, such as trialkylsulfonium cations, or sulfoxonium cations, are known from the literature (cf. for example DE-A 22 23 894, DE-A 24 33 067, DE-A 25 76 251, DE-A 30 04 770, BE-A 868 875 and BE-A 858 618).

The 2-(4-hetaryloxy)- and 2-(4-aryloxy)-phenoxyacetic acid derivatives III may contain one or more centers of asymmetry. They act as racemates, as obtained in most preparation processes, but if desired, can also be separated into the pure isomers by the conventional methods, for example over an optically active adsorbent.

The racemates and pure isomers serve for controlling undesirable plants from the family consisting of the Gramineae. However, the toleration of these substances by crops varies from commercially acceptable to non-tolerated, depending on the substituents and the application rate.

Specific examples of herbicides 2-(4-hetaryloxy)- and 2-(4-aryloxy)-phenoxyacetic acid derivatives of the formula III whose toleration by plants can be improved by substituted 3-aminobenzo[b]thiophenes I are shown in Table 9 below:

TABLE 9

$$R^o-\text{C}_6\text{H}_4-O-CH(R^p)-C(=O)-O-R^q \quad \text{III}$$

| No. | $R^o$ | $R^p$ | $R^q$ | Reference |
|---|---|---|---|---|
| B.01 | 2,4-dichlorophenyl | $CH_3$ | $-CH_3$ | DE-A 22 23 894 |
| B.02 | 5-trifluoromethyl-pyridin-2-yl | $CH_3$ | $-n$-$C_4H_9$ | BE-A 868 875 |
| B.03 | 5-trifluoromethyl-pyridin-2-yl | $CH_3$ | $-CH_2CH_2OCH_2H_5$ | US-A 4 753 673 |

TABLE 9-continued $$R^o-O-\underset{\text{(phenyl)}}{\bigcirc}-O-CH-\overset{R^p}{\underset{|}{C}}-\overset{O}{\underset{||}{C}}-O-R^q \quad \text{III}$$

| No. | R⁰ | Rᵖ | Rᵍ | Reference |
|---|---|---|---|---|
| B.04 | (N-isopropylidene-amino-phenyl with Cl) | CH₃ | —C₂H₅ | BE-A 858 618 |
| B.05 | (3-Cl, 5-CF₃ pyridinyl) | CH₃ | —CH₃ | BE-A 868 875 |
| B.06 | (3-F, 5-Cl pyridinyl) | CH₃ | —CH₂—C≡CH | EP-A 248 968 |
| B.07 | (3,5-diCl pyridinyl) | CH₃ | (N-oxazolidinyl) | DE-A 32 46 847 |
| B.08 | (6-Cl quinoxalinyl) | CH₃ | —C₂H₅ | DE-A 30 04 770 |
| B.09 | (6-Cl quinoxalinyl) | CH₃ | —CH₂CH₂—ON=C(CH₃)₂ | EP 54 715 |
| B.10 | (6-Cl quinoxalinyl) | CH₃ | —CH₂-(tetrahydrofuranyl) | EP-A 323 727 |

The herbicidal active ingredients and the antidote compounds can be applied together or separately, after emergence, to the leaves and shoots of the crops and undesirable grasses. However, the herbicidal and antidote active ingredients are preferably applied simultaneously to the field. In the separate application of antidote and herbicidal active ingredient, the antidote is preferably applied first.

The antidote and the herbicidal active ingredient may be formulated together or separately any may then be in suspendable, emulsifiable or soluble form for the preparation of sprays.

Antidote effects are also achieved by treating the seeds of the crops or the seedlings with the antidote prior to sowing or prior to planting out. The herbicidal active ingredient is then applied alone in the conventional manner.

In the case of seed treatment, in general from 0.1 to 10 g, preferably from 1 to 2 g, of active ingredient are required per kilogram of seed.

In the case of the application of the antidote by seed swelling or in the case of seedling treatment, it is preferable to use solutions which contain the antagonistic active ingredient in a concentration of from 1 to 10,000 ppm, in particular from 100 to 10,000 ppm.

Different amounts of antidote compound I and herbicidal compound II or III are usually required in the various crops, the ratios being variable in wide ranges. They are dependent on the structure of the cyclohexenone derivatives II or of the hetaryloxy- and aryloxyphenoxyacetic acid derivatives III, on the substituted 3-aminobenzo[b]thiophenes I and on the particular crop to which the compounds are applied. Suitable ratios of herbicidal active ingredient to substituted 3-aminobenzo[b]thiophene I acting as an antidote are from 1:10 to 1:0.01, preferably from 1:4 to 1:0.1.

The novel agents or, in the case of separate application, the herbicidal active ingredient or the antidote is or are applied, for example, in the form of directly sprayable solutions, powders, suspensions, or including concentrated aqueous, oily or other suspensions, dispersions, emulsions, oil dispersions, pastes, dusts, broadcasting agents or granules by spraying, nebulizing, dusting, broadcasting or pouring. The application form depends entirely on the particular intended use.

Mineral oil fractions of medium to high boiling point such as kerosine and diesel oil, as well as coke oils and oils and fats of vegetable or animal origin, aliphatic, cyclic or aromatic hydrocarbons, for example methanol, ethanol, isopropanol, butanol, chloroform, carbon tetrachloride, cyclohexanol, cyclohexanone, chlorobenzene, toluene, xylenes, paraffin, tetrahydronaphthalene, alkylated naphthalenes or derivatives thereof or isophorone, and strongly polar solvents, such as dimethylformamide, dimethyl sulfoxide, N-methylpyrrolidone and preferably water, are suitable for the preparation of directly sprayable solutions, emulsions, pastes and oil dispersions.

Aqueous application forms can be prepared from emulsion concentrates, pastes, wettable powders or oil dispersions by adding water. For the preparation of emulsions, pastes or oil dispersions, herbicidal active ingredient and/or antidote, as such or dissolved in an oil or solvent, can be homogenized with water by means of wetting agents, adherents, dispersants or emulsifiers. However, it is also possible to prepare concentrates which consist of herbicidal active ingredient and/or antidote, wetting agents, adherents, dispersants or emulsifiers and, if desired, solvents or oil which are suitable for dilution with water.

Suitable surfactant salts are alkali metal, alkaline earth metal and ammonium salts of ligninsulfonic acid, naphthalenesulfonic acid, phenolsulfonic acid, alkylarylsulfonates, alkylsulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, octadecanols, salts of sulfated fatty alcohol glycol ethers, condensates of sulfated naphthalene and naphthalene derivatives with formaldehyde, condensates of naphthalene or naphthalenesulfonic acids with phenol and formaldehyde, polyoxyethylene octylphenol ethers, ethoxylated isooctylphenol, octylphenol or nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusts can be prepared by mixing or milling the herbicidal active ingredient and/or antidote together with a solid carrier.

Granules, for example coated, impregnated and homogenized granules, can be prepared by binding the active ingredients to solid carriers. Solid carriers are, for example, mineral earths, such as silica gel, silicas, silicates, talc, kaolin, attaclay, limestone, chalk, talc, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flours, bark meal, wood meal and nutshell meal, cellulosic powder and other solid carriers.

The formulations contain from 0.02 to 95, preferably from 0.5 to 90,% by weight of herbicidal active ingredient and antidote. The application rates of the herbicidal active ingredient are from 0.05 to 5 kg/ha.

In addition to the antagonistic substituted 3-aminobenzo[b]thiophenes I and herbicide selected from the group consisting of the cyclohexenones II or the hetaryloxy- or aryloxyphenoxyacetic acids III, the herbicides may contain further herbicidal or growth-regulating active ingredients having a different chemical structure, the antagonistic effect of the 3-aminobenzo[b]thiophenes being retained.

PREPARATION EXAMPLES
(3-aminobenzo[b]thiophenes I and I')

Example 5

3,5-Diamino-4-cyano-2-acylbenzo[b]thiophene

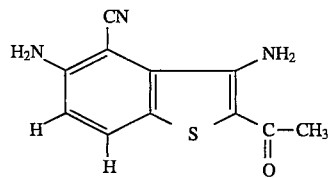

0.1 mol of sodium methylate (as a 30% strength by weight solution in methanol) is added to a solution of 0.1 mol of 5-amino-4-cyanobenzoisothiazole in 300 ml of methoxypropanol. Stirring is carried out for 1 hour at 100° C., followed by cooling to 50° C. After the addition of 0.1 mol of chloroacetone and a further 0.1 mol of sodium methylate (as a 30% strength by weight solution in methanol), the mixture was heated at 100° C. for a further 2.5 hours and then stirred into 3000 ml of water. The precipitate formed was separated off, washed with water and dried. Yield: 80%; mp.: >250° C.

If another carbonyl compound is used instead of chloroacetone, further 3,5-diamino-4-cyano-2-benzo[b]thiophene derivatives are obtained in the same manner, starting from 5-amino-4-cyanobenzoisothiazole. Corresponding carbonyl compounds and the novel compounds I' obtained therefrom are shown in Table 10 by way of example:

TABLE 10

Novel 3-aminobenzo[b]thiophenes

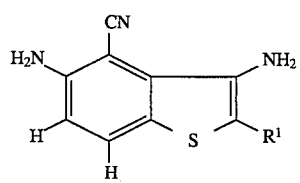

| No. | Carbonyl compound | R¹ | Yield | mp. (°C.) |
|---|---|---|---|---|
| 1 | 2-chloroacetamide | —CONH$_2$ | 80% | >250 |

TABLE 10-continued

Novel 3-aminobenzo[b]thiophenes

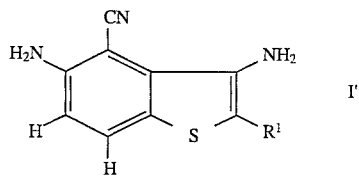

| No. | Carbonyl compound | $R^1$ | Yield | mp. (°C.) |
|---|---|---|---|---|
| 2 | methyl chloroacetate | $-COOCH_3$ | 99% | 198–200 |
| 3 | hept-2-yl chloroacetate | $-COOCH(CH_3)-(CH_2)_4-CH_3$ | 75% | 81–83 |
| 4 | tert-butyl bromoacetate | $-COO-C(CH_3)_3$ | 80% | 112–115 |
| 5 | ethyl acetochloroacetate | $-CO-CH_2COOC_2H_5$ | 19% | >250 |
| 6 | ethyl bromopyruvate | $-CO-COOC_2H_5$ | 36% | 148–150 |
| 7 | benzyl bromoacetate | $-COOCH_2-C_6H_5$ | 85% | 240–245 |
| 8 | bromoacetophenone | $-CO-C_6H_5$ | 96% | 177–179 |
| 9 | propenyl chloroacetate | $-COOCH_2-CH=CH_2$ | 68% | 228–230 |
| 10 | butyl chloroacetate | $-COO(CH_2)_3-CH_3$ | 78% | 217–218 |
| 11 | Sodium chloroacetate | $-COOH$ | 67% | 172–174 |
| 12 | Chloroacetone | $-CO-CH_3$ | 71% | 192–194 |

EXAMPLES OF THE BIOLOGICAL ACTION

The effect of various typical novel herbicides or combinations of agents consisting of herbicide and antidote compound on the growth of desirable and undesirable plants in comparison with the herbicidal active ingredient alone is demonstrated by the following biological examples from greenhouse experiments:

In greenhouse experiments, plastic flower pots having a capacity of about 300 cm³ and containing loamy sand with about 3.0% by weight of humus as a substrate served as culture vessels. The seeds of the test plants were sown shallowly and separately according to species and were moistened. Thereafter, the vessels were covered with transparent plastic covers until the seeds had uniformly germinated and the plants had begun to grow.

| List of test plants | |
|---|---|
| Botanical name | Common name |
| Triticum sativum | winter wheat |
| Triticum sativum | spring wheat |
| Zea mays | corn |
| Setaria viridis | green foxtail |

For the post-emergence treatment, the test plants were first grown to a height of growth of from 3 to 20 cm depending on the form of growth, and only then treated. The herbicides were suspended or emulsified in water as distributing agent and sprayed by means of finely distributing nozzles.

The cyclohexenone derivatives II served as example herbicides

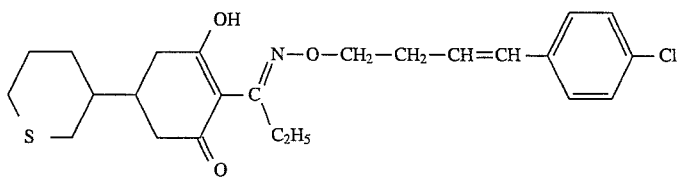

No. A.052

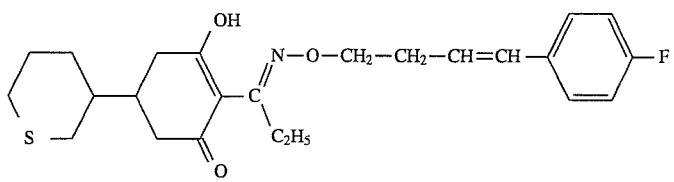

No. A.053

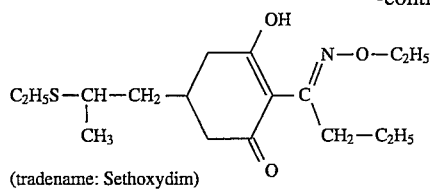

(tradename: Sethoxydim)

For the post-emergence treatment, all antidote compounds were prepared in a mixture consisting of 80% by weight of cyclohexenone as a diluent and 20% by weight of surfactant (Emulphor® EL; ethoxylated castor oil) with 10% by weight of active ingredient.

For comparison, the herbicidal active ingredient was formulated as 10–20% strength by weight emulsion concentrate and used in the spray liquor in each case with the addition of the amount of solvent system to which the antidote compound was applied at the application rates stated in the Tables. The solution was prepared by mixing the active ingredient into a solution of 93% by weight of xylene and 7% by weight of Lutensol® AP-8 (nonionic surfactant based on alkylphenol polyethylene glycol ethers).

After application of the particular active ingredient mixture, the test plants were cultivated in a greenhouse, heat-loving species at about 18° to 30° C. and those of more temperate climates at about 10° to 25° C.

The test period extended over 3 to 5 weeks. During this time, the plants were tended, their reactions to the active ingredient treatments being recorded.

The damage caused by the chemical agents was rated on a scale from 0 to 100% in comparison with the untreated control plants. 0 means no damage and 100 means complete destruction of the plants.

The improvement in the toleration of herbicidal cyclohexenone derivatives II for crops from the Gramineae family (grasses) such as wheat and corn, due to the 3-aminobenzo[b]thiophenes I is shown in Tables 11 to 15 below:

No. A.001

TABLE 11

Improvement in the toleration of herbicide No. A.052 by wheat and corn as a result of admixing an antidote example compound for use in post-emergence application; greenhouse experiment

| Antidote | Application rate [kg/ha a.s.] | | Test plants and damage [%] | | |
|---|---|---|---|---|---|
| | | | Crops | | Undesirable plant |
| No. | Antidote | Herbicide | Winter wheat | Corn | Green foxtail |
| — | — | 0.25 | 85 | 80 | 100 |
| 02 | 0.25 | 0.25 | 25 | 0 | 100 |
| 03 | 0.25 | 0.25 | 35 | 0 | 100 |
| 12 | 0.25 | 0.25 | 70 | 65 | 95 |
| — | — | 0.125 | 80 | 70 | 100 |
| 02 | 0.125 | 0.125 | 25 | 0 | 90 |
| 03 | 0.125 | 0.125 | 10 | 0 | 100 |
| 12 | 0.125 | 0.125 | 60 | 40 | 90 |
| — | — | 0.06 | 60 | 40 | 98 |
| 02 | 0.06 | 0.06 | 25 | 0 | 95 |
| 03 | 0.06 | 0.06 | 10 | 0 | 85 |
| 12 | 0.06 | 0.06 | 40 | 40 | 98 |
| — | — | 0.03 | 30 | 10 | 60 |
| 02 | 0.03 | 0.03 | 20 | 0 | 75 |
| 03 | 0.03 | 0.03 | 10 | 0 | 65 |
| 12 | 0.03 | 0.03 | 15 | 10 | 60 |

TABLE 12

Improvement in the toleration of herbicide No. A.052 by corn as a result of admixing an antidote example compound for use in post-emergence application; greenhouse experiment

| Antidote | Application rate [kg/ha a.s.] | | Test plants and damage [%] | |
|---|---|---|---|---|
| | | | Crop | Undesirable plant |
| No. | Antidote | Herbicide | Corn | Green foxtail |
| — | — | 0.25 | 80 | 100 |
| 08 | 0.25 | 0.25 | 20 | 100 |
| — | — | 0.125 | 75 | 100 |
| 08 | 0.125 | 0.125 | 20 | 95 |
| — | — | 0.06 | 60 | 98 |
| 08 | 0.06 | 0.06 | 5 | 75 |
| 11 | 0.06 | 0.06 | 30 | 95 |
| — | — | 0.03 | 10 | 60 |
| 08 | 0.03 | 0.03 | 0 | 50 |
| 11 | 0.03 | 0.03 | 20 | 75 |

TABLE 13

Improvement in the toleration of herbicide No. A.052 by wheat and corn as a result of admixing an antidote example compound for use in post-emergence application; greenhouse experiment

| Antidote | Application rate [kg/ha a.s.] | | Test plants and damage [%] | | |
|---|---|---|---|---|---|
| | | | Crops | | Undesirable plant |
| No. | Antidote | Herbicide | Winter wheat | Corn | Green foxtail |
| — | — | 0.125 | 85 | 90 | 90 |
| 09 | 0.125 | 0.125 | 75 | 20 | 90 |
| 10 | 0.125 | 0.125 | 65 | 15 | 85 |
| — | — | 0.06 | 70 | 80 | 80 |
| 09 | 0.06 | 0.06 | 55 | 10 | 85 |
| 10 | 0.06 | 0.06 | 25 | 10 | 85 |

TABLE 14

Improvement in the toleration of herbicide No. A.053 by wheat and corn as a result of admixing an antidote example compound for use in post-emergence application; greenhouse experiment

| Antidote | Application rate [kg/ha a.s.] | | Test plants and damage [%] | | |
|---|---|---|---|---|---|
| | | | Crops | | Undesirable plant |
| No. | Antidote | Herbicide | Summer wheat | Corn | Green foxtail |
| — | — | 0.06 | 80 | 80 | 90 |
| 02 | 0.06 | 0.06 | 15 | 50 | 95 |
| 03 | 0.06 | 0.06 | 0 | 25 | 98 |
| 04 | 0.06 | 0.06 | 15 | 70 | 90 |
| 09 | 0.06 | 0.06 | 15 | 25 | 95 |
| 10 | 0.06 | 0.06 | 0 | 40 | 95 |

TABLE 14-continued

Improvement in the toleration of herbicide No. A.053 by wheat and corn as a result of admixing an antidote example compound for use in post-emergence application; greenhouse experiment

| Antidote No. | Application rate [kg/ha a.s.] | | Test plants and damage [%] | | |
|---|---|---|---|---|---|
| | | | Crops Summer | | Undesirable plant |
| | Antidote | Herbicide | wheat | Corn | Green foxtail |
| — | — | 0.03 | 70 | 80 | 90 |
| 02 | 0.03 | 0.03 | 10 | 35 | 90 |
| 03 | 0.03 | 0.03 | 0 | 25 | 80 |
| 04 | 0.03 | 0.03 | 15 | 60 | 90 |
| 09 | 0.03 | 0.03 | 10 | 20 | 90 |
| 10 | 0.03 | 0.03 | 0 | 40 | 85 |
| — | — | 0.015 | 25 | 80 | 90 |
| 02 | 0.015 | 0.015 | 10 | 25 | 85 |
| 03 | 0.015 | 0.015 | 0 | 15 | 70 |
| 04 | 0.015 | 0.015 | 10 | 25 | 90 |
| 09 | 0.015 | 0.015 | 10 | 10 | 70 |
| 10 | 0.015 | 0.015 | 0 | 30 | 70 |

TABLE 15

Improvement in the toleration of herbicide No. A.001 by wheat and corn as a result of admixing an antidote example compound for use in post-emergence application; greenhouse experiment

| Antidote No. | Application rate [kg/ha a.s.] | | Test plants and damage [%] | | |
|---|---|---|---|---|---|
| | | | Crops Summer | | Undesirable plant |
| | Antidote | Herbicide | wheat | Corn | Green foxtail |
| — | — | 0.06 | 90 | 90 | 90 |
| 09 | 0.06 | 0.06 | 0 | 60 | 90 |
| 10 | 0.06 | 0.06 | 10 | 65 | 85 |
| — | — | 0.03 | 75 | 75 | 90 |
| 09 | 0.03 | 0.03 | 0 | 60 | 75 |
| 10 | 0.03 | 0.03 | 0 | 55 | 65 |

We claim:

1. A herbicide containing one or more antagonistic 3-aminobenzo[b]-thiophenes of the formula I'

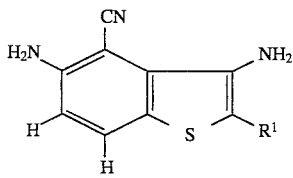

where $R^1$ is —COX or —COOX,

X is hydrogen, halogen, amino which may be unsubstituted or may carry from one to three substituents selected from the group consisting of $C_1$–$C_4$-alkyl, hydroxy-$C_1$–$C_4$-alkyl, phenyl and benzyl substituents, $C_1$–$C_{10}$-alkyl, $C_2$–$C_8$-alkenyl, $C_3$–$C_{10}$-cycloalkyl or $C_3$–$C_{10}$-cycloalkenyl, where the four last-mentioned groups may be unsubstituted or partially or completely halogenated and the four last-mentioned groups may furthermore contain one or two further carboxyl or carbonyl groups, a 5-membered or 6-membered aromatic heterocyclic structure having one oxygen and one sulfur atom or having from one to three hetero atoms selected from the group consisting of three nitrogen atoms and one oxygen or sulfur atom, where three hetero atoms may not be adjacent to one another simultaneously, phenyl or naphthyl, where these groups may carry from one to three substituents selected from the group consisting of halogen, —COY and —COOY, and the phenyl and naphthyl groups may additionally carry a number of halogen atoms corresponding to the number of substitutable carbon atoms present, and Y is $C_1$–$C_6$-alkyl, $C_3$–$C_6$-cycloalkyl or phenyl and one or more herbically active ingredients which are deterimental to crops selected from A) the group consisting of the cyclohexenone derivatives of the formula II

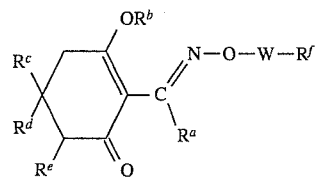

where $R^a$ is $C_1$–$C_6$-alkyl, $R^b$ is hydrogen, the equivalent of an agriculturally useful cation, $C_2$–$C_8$-alkylcarbonyloxy, $C_1$–$C_{10}$-alkylsulfonyl, $C_1$–$C_{10}$-alkylphosphonyl or benzoyl, benzenesulfonyl or benzenephosphonyl, where the three last-mentioned groups may furthermore each carry from one to five halogen atoms;

$R^c$ is hydrogen, cyano, formyl, $C_1$–$C_6$-alkyl, $C_1$–$C_4$-alkoxy-$C_1$–$C_6$-alkyl or $C_1$–$C_4$-alkylthio-$C_1$–$C_6$-alkyl, phenoxy-$C_1$–$C_6$-alkyl, phenylthio-$C_1$–$C_6$-alkyl, pyridyloxy-$C_1$–$C_6$-alkyl or pyridylthio-$C_1$–$C_6$-alkyl, where the phenyl and pyridyl rings may each furthermore carry from one to three radicals selected from the group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^3R^h$, where $R^g$ is hydrogen, $C_1$–$C_4$-alkyl, $C_3$–$C_6$-alkenyl, $C_3$–$C_6$-alkynyl, $C_1$–$C_6$-acyl or benzoyl which may carry from one to three radicals selected from the group consisting of nitro, cyano, halogen, $C_1$–$C_4$-alkyl, partially or completely halogenated $C_1$–$C_4$-alkyl, $C_1$–$C_4$-alkoxy and $C_1$–$C_4$-alkylthio and $R^h$ is hydrogen, $C_1$–$C_4$-alkyl, $C_3$–$C_6$-alkenyl or $C_3$–$C_6$-alkynyl; $C_3$–$C_7$-cycloalkyl or $C_5$–$C_7$-cycloalkenyl, where these groups may furthermore carry from one to three radicals selected from the group consisting of hydroxyl, halogen, $C_1$–$C_4$-alkyl, partially or completely halogenated $C_1$–$C_4$-alkyl, $C_1$–$C_4$-alkoxy, $C_1$–$C_4$-alkylthio, benzylthio, $C_1$–$C_4$-alkylsulfonyl, $C_1$–$C_4$-alkylsulfenyl and $C_1$–$C_4$-alkylsulfinyl, a 5-membered saturated heterocyclic structure which contains one or two oxygen or sulfur atoms or one oxygen and one sulfur atom as hetero atoms and which may furthermore carry from one to three radicals selected from the group consisting of $C_1$–$C_4$-alkyl, partially or completely halogenated $C_1$–$C_4$-alkyl, $C_1$–$C_4$-alkoxy and $C_1$–$C_4$-alkylthio, a 6-membered or 7-membered saturated heterocyclic structure or a mono- or diunsaturated heterocyclic structure which contains one or two oxygen or sulfur atoms or one oxygen and one sulfur atom as hetero atoms and which may furthermore carry from one to three radicals selected from the group consisting of hydroxyl, halogen, $C_1$–$C_4$-alkyl, partially or completely halogenated $C_1$–$C_4$-alkyl, $C_1$–$C_4$-alkoxy and $C_1$–$C_4$-alkylthio, a 5-membered heteroaromatic structure containing from one to three hetero atoms selected from the group consisting of one or two nitrogen atoms and one oxygen or sulfur atom, where the heteroaromatic structure may furthermore carry from one to three radicals selected from the group consisting of cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_2$–$C_6$-alkenyl, $C_2$–$C_6$-alkenyloxy, $C_3$–$C_6$-alkynyloxy and $C_1$–$C_4$-alkoxy-$C_1$–$C_4$-alkyl, phenyl or pyridyl, each of which may furthermore carry from one to three radicals selected from the group consisting of nitro, cyano, formyl, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^gR^h$, where $R^g$ and $R^h$ have the abovementioned meanings;

$R^d$ is hydrogen or hydroxyl or, when $R^c$ is $C_1$–$C_6$-alkyl, $R^d$ is $C_1$–$C_6$-alkyl;

$R^e$ is hydrogen, halogen, cyano, a $C_1$–$C_4$-alkoxycarbonyl or a $C_1$–$C_4$-alkylketoxime group;

W is a $C_1$–$C_6$-alkylene, $C_3$–$C_6$-alkenylene or $C_3$–$C_6$-alkynylene chain, each of which may furthermore carry from one to three radicals selected from the group consisting of three $C_1$–$C_3$-alkyl substituents, three halogen atoms and one methylene substituent;

a $C_3$–$C_6$-alkylene or $C_4$–$C_6$-alkenylene chain, both of which may furthermore carry from one to three $C_1$–$C_3$-alkyl radicals, where in each case one methylene group of the chains may be replaced by an oxygen or sulfur atom, a sulfoxyl or sulfonyl group or a group —$N(R^i)$—, where $R^i$ is hydrogen, $C_1$–$C_4$-alkyl, $C_3$–$C_6$-alkenyl or $C_3$–$C_6$-alkynyl;

$R^f$ is hydrogen; vinyl;

a group —CH=CH—Z, where Z is cyano, halogen, $C_1$–$C_4$-alkyl, partially or completely halogenated $C_1$–$C_4$-alkyl, $C_3$–$C_6$-cycloalkyl, which, if desired, in turn may carry from one to three substituents selected from the group consisting of hydroxyl, halogen, $C_1$–$C_4$-alkyl, partially or completely halogenated $C_1$–$C_4$-alkyl and $C_1$–$C_4$-alkoxy;

carboxy, $C_1$–$C_8$-alkoxycarbonyl, benzyloxycarbonyl, phenyl, thienyl or pyridyl, where these three aromatic radicals may be unsubstituted or may each furthermore carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio and $C_3$–$C_6$-cycloalkyl, where the cycloalkyl substituent may be unsubstituted or in turn may furthermore carry from one to three radicals selected from the group consisting of halogen, $C_1$–$C_4$-alkyl, partially or completely halogenated $C_1$–$C_4$-alkyl and $C_1$–$C_4$-alkoxy;

ethynyl which may carry one of the following radicals: $C_1$–$C_4$-alkyl, $C_3$–$C_6$-cycloalkyl, which, if desired, may furthermore carry from one to three substituents selected from the group consisting of hydroxyl, halogen, $C_1$–$C_4$-alkyl, partially or completely halogenated $C_1$–$C_4$-alkyl and $C_1$–$C_4$-alkoxy, or phenyl, thienyl or pyridyl, where these aromatic radicals may be unsubstituted or may each furthermore carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy and $C_1$–$C_4$-alkylthio;

phenyl, halophenyl, dihalophenyl, a 5-membered heteroaromatic group having from one to three hetero atoms, selected from the group consisting of from one to three nitrogen atoms and one oxygen or sulfur atom, or a 6-membered heteroaromatic group having from one to four nitrogen atoms, all of which may not be adjacent to one another at the same time, where the phenyl and hetaryl groups may, if desired, furthermore carry from one to three radicals selected from the group consisting of nitro, $C_1$–$C_4$-alkoxy, $C_1$–$C_4$-alkylthio, partially or completely halogenated $C_1$–$C_4$-alkoxy, radicals Z and —$NR^kR^l$, where $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl which, if desired, may furthermore carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy and $C_1$–$C_4$-alkylthio.

2. A herbicide as claimed in claim 1, containing one or more antagonistic 3-aminobenzo[b]thiophenes I and one or more herbicides II in a ratio of from 1:10 to 10:1.

3. A method for selectively controlling undesirable plant growth on cultivated areas, wherein an antagonistic amount of one or more 3-aminobenzo[b]thiophene I and A) a herbicidal amount of one or more cyclohexenone derivatives of the formula II as claimed in claim 1 are applied, simultaneously or in succession, before, during or after sowing of the crops or before or during emergence of the crops.

4. A method for selectively inhibiting undesirable plant growth on cultivated areas, wherein the leaves of the crops and of the undesirable plants are treated with a herbicide as claimed in claim 1 by the post-emergence method, where the active ingredient components of the herbicide may be applied simultaneously or in succession.

5. A method for selectively inhibiting undesirable plant growth on cultivated areas, wherein the leaves of the crops and of the undesirable plants are treated with a herbicide as claimed in claim 1 by the post-emergence method, where the active ingredient components of the herbicide may be applied simultaneously or in succession.

6. A method for selectively inhibiting undesirable plant growth on cultivated areas, wherein the leaves of the crops and of the undesirable plants are treated with a herbicide as claimed in claim 2 by the post-emergence method, where the active ingredient components of the herbicide may be applied simultaneously or in succession.

7. A method for preventing damage to crops by

A) a herbicidally effective amount of cyclohexenone derivatives of the formula II, wherein the seed of the crops is treated with antagonistic amounts of 3-aminobenzo[b]thiophenes of the formula I as claimed in claim 1.

8. A method as claimed in claim 3, wherein the crop is barley, wheat, corn, sorghum or rice.

* * * * *

UNITED STATES PATENT AND TRADEMARK OFFICE
CERTIFICATE OF CORRECTION

PATENT NO.: 5,491,123

DATED: February 13, 1996

INVENTOR(S): HAGEN et al.

It is certified that error appears in the above-identified patent and that said Letters Patent is hereby corrected as shown below:

Column 94, claim 1, line 45, "$NR^3R^h$" should be --$NR^gR^h$--.

Column 95, claim 1, line 57, "carboxy" should be --carboxyl--.

Column 96, claim 1, line 31, "$R^1$" should be --$R^t$--.

Signed and Sealed this

Seventh Day of May, 1996

Attest:

BRUCE LEHMAN

Attesting Officer

Commissioner of Patents and Trademarks